US011160856B2

(12) United States Patent
McConnell et al.

(10) Patent No.: US 11,160,856 B2
(45) Date of Patent: Nov. 2, 2021

(54) **VACCINE AGAINST *ACINETOBACTER BAUMANNII* BASED ON CELLULAR COMPONENTS DEFICIENT IN LIPOPOLYSACCHARIDE**

(71) Applicants: VAXDYN S.L, Seville (ES); FUNDACIÓN PÚBLICA ANDALUZA PARA LA GESTIÓN DE LA INVESTIGACIÓN EN SALUD DE SEVILLA, Seville (ES); SERVICIO ANDALUZ DE SALUD, Seville (ES)

(72) Inventors: Michael James McConnell, Seville (ES); Meritxell García Quintanilla, Seville (ES); Marina Pulido Toledano, Seville (ES); María Pilar Pérez Romero, Seville (ES); Jerónimo Pachón Díaz, Seville (ES); Juan José Infante Viñolo, Seville (ES)

(73) Assignees: Vaxdyn S.L., Seville (ES); Fundación Pública Andaluza para la Gestión de la Investigación en Salud De Sevilla, Seville (ES); Servicio Andaluz de Salud, Seville (ES)

( * ) Notice: Subject to any disclaimer, the term of this patent is extended or adjusted under 35 U.S.C. 154(b) by 106 days.

(21) Appl. No.: 15/878,491

(22) Filed: Jan. 24, 2018

(65) Prior Publication Data
US 2018/0256700 A1      Sep. 13, 2018

Related U.S. Application Data

(62) Division of application No. 15/308,899, filed as application No. PCT/EP2015/059870 on May 5, 2015, now abandoned.

(30) Foreign Application Priority Data

May 5, 2014    (EP) ..................................... 14382164

(51) Int. Cl.
| | |
|---|---|
| A61K 39/104 | (2006.01) |
| A61K 35/74 | (2015.01) |
| C07K 14/21 | (2006.01) |
| C12N 9/10 | (2006.01) |
| C12N 9/78 | (2006.01) |
| C07K 16/12 | (2006.01) |
| A61K 39/00 | (2006.01) |

(52) U.S. Cl.
CPC ............ *A61K 39/104* (2013.01); *A61K 35/74* (2013.01); *C07K 14/212* (2013.01); *C07K 16/1203* (2013.01); *C12N 9/1025* (2013.01); *C12N 9/1048* (2013.01); *C12N 9/78* (2013.01); *A61K 2039/505* (2013.01); *A61K 2039/521* (2013.01); *A61K 2039/575* (2013.01); *C07K 2319/00* (2013.01)

(58) Field of Classification Search
None
See application file for complete search history.

(56) References Cited

U.S. PATENT DOCUMENTS

2017/0065700 A1    3/2017 McConnell et al.

FOREIGN PATENT DOCUMENTS

| CN | 101575587 A | 11/2009 |
|---|---|---|
| ES | 2366735 A1 | 10/2011 |
| WO | WO 2013/040478 A2 | 3/2013 |
| WO | WO 2014/048976 A1 | 4/2014 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Van der Ley et al. (Journal of Endotoxin Research vol. 9, No. 2, pp. 124-128).*
McConnell et al. (Vaccine vol. 29 p. 1-5).*
Baumann, Isolation of Acinetobacter from soil and water. J Bacteriol. Jul. 1968;96(1):39-42.
Beceiro et al., Biological cost of different mechanisms of colistin resistance and their impact on virulence in Acinetobacter baumannii. Antimicrob Agents Chemother. 2014;58(1):518-26. doi: 10.1128/AAC.01597-13.
Bentancor et al., Evaluation of the trimeric autotransporter Ata as a vaccine candidate against Acinetobacter baumannii infections. Infect Immun. Oct. 2012;80(10):3381-8. doi: 10.1128/IAI.06096-11.
Bentancor et al., Poly-N-acetyl-β-(1-6)-glucosamine is a target for protective immunity against Acinetobacter baumannii infections. Infect Immun. Feb. 2012;80(2):651-6. doi:10.1128/IAI.05653-11.
Bishop et al., Immunization of mice with Vibrio cholerae outer-membrane vesicles protects against hyperinfectious challenge and blocks transmission. J Infect Dis. Feb. 1, 2012;205(3):412-21. doi: 10.1093/infdis/jir756.
García-Quintanilla et al., Immunization with lipopolysaccharide-deficient whole cells provides protective immunity in an experimental mouse model of Acinetobacter baumannii infection. PLoS One. Dec. 8, 2014;9(12):e114410. doi: 10.1371/journal.pone.0114410.
Goel et al., Monoclonal antibodies against the iron regulated outer membrane Proteins of Acinetobacter baumannii are bactericidal. BMC Microbiol. 2001;1:16.
Keenan et al., Differences in immunogenicity and protection in mice and guinea pigs following intranasal immunization with Helicobacter pylori outer membrane antigens. FEMS Immunol Med Microbiol. May 25, 2003;36(3): 199-205.

(Continued)

Primary Examiner — Robert A Zeman
(74) Attorney, Agent, or Firm — Wolf, Greenfield & Sacks, P.C.

(57) ABSTRACT

The invention refers to a composition comprising inactivated cells deficient in LPS from the genus *Acinetobacter* and/or outer membrane vesicles form the same and their use for the manufacture of a medicament, preferably a vaccine, for the prevention of diseases produced by organisms of the genus *Acinetobacter*.

2 Claims, 11 Drawing Sheets

Figure 1A:
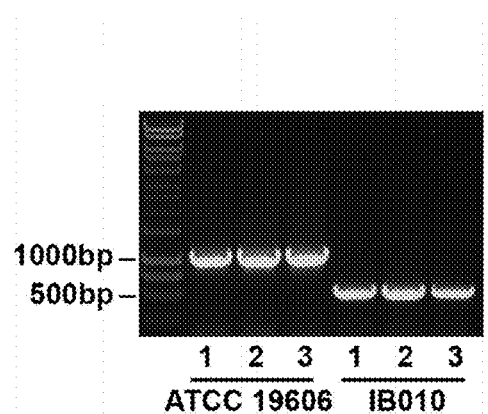

Specification includes a Sequence Listing.

(56) References Cited

OTHER PUBLICATIONS

Kesty et al., Enterotoxigenic *Escherichia coli* vesicles target toxin delivery into mammalian cells. EMBO J. Nov. 24, 2004;23(23):4538-49.

Kuehn et al., Bacterial outer membrane vesicles and the host-pathogen interaction. Genes Dev. Nov. 15, 2005;19(22):2645-55.

Kulp et al., Biological functions and biogenesis of secreted bacterial outer membrane vesicles. Annu Rev Microbiol. 2010;64:163-84. doi:10.1146/annurev.micro.091208.073413.

Luo et al., Active and passive immunization protects against lethal, extreme drug resistant-Acinetobacter baumannii infection. PLoS One. 2012;7(1):e29446. doi: 10.1371/journal.pone.0029446.

Mcconnell et al., Vaccination with outer membrane complexes elicits rapid protective immunity to multidrug-resistant Acinetobacter baumannii. Infect Immun. Jan. 2011;79(1):518-26. doi: 10.1128/IAI.00741-10.

Moffatt et al., Colistin resistance in Acinetobacter baumannii is mediated by complete loss of lipopolysaccharide production. Antimicrob Agents Chemother. Dec. 2010;54(12):4971-7. doi: 10.1128/AAC.00834-10.

Moffatt et al., Insertion sequence ISAba11 is involved in colistin resistance and loss of lipopolysaccharide in Acinetobacter baumannii. Antimicrob Agents Chemother. Jun. 2011;55(6):3022-4. doi: 10.1128/AAC.01732-10.

Ong et al., Severe community-acquired Acinetobacter baumannii pneumonia: an emerging highly lethal infectious disease in the Asia-Pacific. Respirology. Nov. 2009;14(8):1200-5. doi: 10.1111/j.1440-1843.2009.01630.x.

Peng et al., Moraxella catarrhalis bacterium without endotoxin, a potential vaccine candidate. Infect Immun. Nov. 2005;73(11):7569-77.

Raetz, Biochemistry of endotoxins. Annu Rev Biochem. 1990;59:129-70.

Steeghs et al., Immunogenicity of outer membrane proteins in a lipopolysaccharide-deficient mutant of Neisseria meningitidis: influence of adjuvants on the immune response. Infect Immun. Oct. 1999;67(10):4988-93.

Henry et al., Colistin-resistant, lipopolysaccharide-deficient Acinetobacter baumannii responds to lipopolysaccharide loss through increased expression of genes involved in the synthesis and transport of lipoproteins, phospholipids, and poly-$\beta$-1,6-N-acetylglucosamine. Antimicrob Agents Chemother. 2012;56(1):59-69. doi:10.1128/AAC.05191-11.

Raetz et al., Discovery of new biosynthetic pathways: the lipid A story. J Lipid Res. Apr. 2009; 50(Suppl): S103-S108. doi: 10.1194/jlr.R800060-JLR200.

Kim et al., Essential role of toll-like receptor 4 in Acinetobacter baumannii-induced immune responses in immune cells. Microb Pathog. Jan. 2013;54:20-5. doi: 10.1016/j.micpath.2012.08.008. Epub Sep. 12, 2012.

Mcconnell et al., Outer membrane vesicles as an acellular vaccine against Acinetobacter baumannii. Vaccine. Aug. 5, 2011;29(34):5705-10. doi: 10.1016/j.vaccine.2011.06.001. Epub Jun. 14, 2011.

Van Der Ley et al., Next-generation outer membrane vesicle vaccines against Neisseria meningitidis based on nontoxic LPS mutants. Hum Vaccin. Aug. 2011;7(8):886-90. doi: 10.4161/hv.7.8.16086. Epub Aug. 1, 2011.

PCT/EP2015/059870, Sep. 14, 2015, International Search Report and Written Opinion.

PCT/EP2015/059870, Nov. 17, 2016, International Preliminary Report on Patentability.

* cited by examiner

FIG. 8

| | | | |
|---|---|---|---|
| OMVs ATCC 19606 | 22.4 | | |
| OMVs ATCC 19606 +DIP | 18.2 | | |
| OMVs IB010 | 133.6 | OMVs ATCC 19606 | 24.2 |
| OMVs IB010 | 158.6 | OMVs ATCC 19606 +DIP | 19.2 |
| OMVs IB010 + 150 DIP | 136.2 | OMVs IB010 | 83.2 |
| OMVs IB010 + 100 DIP | 97.0 | OMVs IB010 + BIP | 149.0 |

ATCC 19606

ATCC 19606 + 200 µM BIP

IB010

IB010 + 150 µM BIP

| | Bradfor | | 2-D QUANT | |
|---|---|---|---|---|
| | µg/µl | Total µg | µg/µl | Total µg |
| IB010 (38ML) | 0.418 | 41.8 | 8.36 | 836 |
| 167R (38ML) | 0.584 | 58.4 | 11.68 | 1168 |
| IB010 (15ML) | 0.580 | 58.0 | 11.60 | 1160 |
| 167R (15ML) | 0.604 | 60.4 | 12.08 | 1208 |

VACCINE AGAINST *ACINETOBACTER BAUMANNII* BASED ON CELLULAR COMPONENTS DEFICIENT IN LIPOPOLYSACCHARIDE

RELATED APPLICATIONS

This application is a divisional of U.S. application Ser. No. 15/308,899, filed Nov. 4, 2016 and now abandoned, which is a national stage filing under 35 U.S.C. § 371 of International Application No. PCT/EP2015/059870, filed May 5, 2015, the entire contents of each of which is incorporated by reference herein in its entirety.

FIELD OF THE INVENTION

The present invention refers, in general, to the field of pharmacology and immunology, and, in particular, to a vaccine composition suitable for the prophylactic treatment of an infection caused by an *Acinetobacter baumannii* strain in a mammal.

BACKGROUND OF THE INVENTION

The increasing clinical importance of infections caused by multidrug resistant *A. baumannii* warrants the development of novel approaches for the prevention and treatment of infections caused by this pathogen. In this context, immunization of certain patient populations could contribute to reducing the morbidity and mortality caused by this pathogen. Vaccines against Gram-negative bacteria based on inactivated whole bacterial cells are highly immunogenic and have been shown to produce protective immunity against a number of bacterial species. However, the high levels of endotoxin, due to the presence of lipopolysaccharide, in these vaccines complicate their use in humans.

*Acinetobacter baumannii* is a Gram-negative coccabacillus with clinical importance in the hospital environment. This organism is highly distributed in soil and environmental water sources (Baumann, P. 1968. *J. Bacteriol.* 96, 39-42), and can cause different types of infections as a nosocomial pathogen such as pneumonia, bacteremia, meningitis and skin and soft tissue infection, among others (García-Quintanilla et al., 2013. *Curr. Pharm. Biotechnol. In press*). This pathogen typically infects patients receiving mechanical ventilation and patients sustaining burn injury (Muñoz-Price y Weinstein. 2008. *N. Engl. J. Med.* 358, 1271-1281). However, it has also been isolated in cases of community-acquired pneumonia (Ho et al., 2009. *Chest.* 136, 1119-1127; Ong et al., 2009. *Respirology* 14, 1200-1205) and in military personnel sustaining war-related trauma in Vietnam, Iraq, Kuwait and Afghanistan (Jones et al., 2006. *Lancet Infect. Dis.* 6, 317-318; Tong, 1972. *JAMA* 219, 1044-1047). The crude mortality rates associated with infection by *A. baumannii* are between 35% and 70% for nosocomial infections (Vila y Pachón, 2008. *Expert Opin. Pharmacother.* 9, 587-599). Due to the ability of *A. baumannii* to acquire resistance to antibiotics, the number of multidrug resistant strains has increased dramatically over the preceding years (Tasbakan et al., 2009. *Mikrobiyol Bul.* 43, 61-70; Valencia et al., 2009. *Infect. Control Hosp. Epidemiol.* 30: 257-263). The appearance of these highly resistant strains has complicated the clinical Management of infections caused by *A. baumannii*. In this context, the development of a vaccine against *A. baumannii* could reduce the morbidity and mortality caused by this pathogen (Pachón y McConnell, 2014. *Vaccine*, In press).

The experimental vaccines that have been described for *A. baumannii* can be classified into two broad groups, vaccines consisting of a single purified antigen, and multicomponent vaccines. Within the first group, the outer membrane protein OmpA (Luo et al., 2012. *PLoS One* 7, e29446), the biofilm associated protein Bap (Fattahian et al., 2011. *Microb. Pathog.* 51, 402-406), the membrane transporter Ata (Bentancor et al., 2012. *Infect. Immun.* 80, 3381-3388), and the suface polysaccharide poly-N-acetyl-β-(1-6)-glucosamine (Bentancor et al., 2012. Infect Immun 80, 651-656) have been described as good candidates due to their capacity to elicit a specific immune response. However, the experiments testing survival after active immunization have only demonstrated that OmpA provides partial protection, and that the expression of Bap has not been clearly demonstrated in strains that do no form biofilm. The approaches that employ multicomponent vaccines include outer membrane complexes (McConnell et al., 2011. *Infect. Immun.* 79, 518-526), outer membrane vesicles (outer membrane vesicles; McConnell et al., 2011. *Vaccine* 29,5705-5710) and inactivated whole cells (McConnell y Pachón, 2010. *Vaccine* 29: 1-5). Each of these vaccines induces a strong immune response and is able to elicit high levels of protection against infection in a murine model using the ATCC 19606 strain and clinical isolates. However, in spite of these promising results, the use of these vaccines in humans is complicated in view of the high levels of endotoxin in these vaccines due to the high amounts of lipopolysaccharide (LPS) present in these preparations.

LPS is formed by the O antigen, a core polysaccharide and lipd A, which is responsible for the endotoxin activity of LPS. The first studies that employed *Escherichia coli* demonstrated that the production of LPS was essential for bacterial viability (Raetz, 1990. *Annu. Rev Biochem.* 59, 129-170). However, subsequent work demonstrated that certain bacterial species, such as *Neisseria meningitidis* y *Moraxella catarrhalis*, were viable after mutation of the genes encoding enzymes involved in LPS biosynthesis, resulting in strains completely lacking LPS (Peng et al., 2005. *Infect. Immun.* 73, 7569-7577; Steeghs et al., 1999. *Infect. Immun.* 67, 4988-4993). A recent study demonstrated that *A. baumannii* can acquire resistance to the antibiotic colistin through mutation of the genes involved in LPS biosynthesis IpxA, IpxC and IpxD (Moffatt et al., 2010. *Antimicrob. Agents Chemother.* 54, 4971-4977), living rise to strains completely deficient in LPS. This results indicate that *A. baumannii* is also viable in the absence of LPS, raising the possibility of developing vaccines based on these strains.

Outer membrane vesicles (OMVs) are vesicles derived from the bacterial outer membrane that are secreted from numerous Gram-negative bacteria (Kulp et al., 2010. *Annu. Rev. Microbiol.* 64, 163-184). OMVs are spherical vesicles of approximately 20-200 nm that are composed of outer membrane proteins, periplasmic proteins and LPS (Kuehn et al., 2005. *Genes Dev.* 19, 2645-2655; Mashburn et al., 2005. *Nature.* 437, 422-425). Secreted OMVs have been shown to participate in the detection of quorum sensing, the transport of virulence factors and the transfer of genes, indicating that they play a role in bacterial patogenesis. It has also been demonstrated that OMVs can deliver proteins to the interior of host cells through fusion with lipid rafts, suggesting that OMVs can be used to transport bacterial products over large distances (Kesty et al., 2004. *Embo J.* 23, 4538-4549). A recent study by Kwon et al demonstrated that a clinical isolate of *A. baumannii* secreted OMVs during growth in vitro (Kwon et al., 2009. *FEMS Microbiol. Lett.* 297, 150-

156). A proteomic analysis of the OMVs demonstrated that they contain multiple virulence factors and immunomodulating proteins, suggesting that OMVs play an important role in the pathogenesis of *A. baumannii*.

Vaccines based on OMVs have been developed for various Gram-negative bacteria including *Neisseria meningitidis, Helicobacter pylori*, and *Vibrio cholerae* (Bjune et al., 1991. *NIPH Ann.* 14, 125-130; Keenan et al., 2003. *FEMS Immunol. Med. Microbiol.* 36, 199-205; Bishop et al., 2012. *J. Infect. Dis.* 205, 412-21). Immunization with OMVs has been shown to induce antibodies against multiple bacterial antigens, and the capacity to provide protective immunity in animal models of infection. In addition, the OMVs isolated form *N. meningitids* serogroup B have been shown to be safe and immunogenic in humans, and have been used to control an outbreak of meningococcus meningitis in New Zealand (Nokleby et al., 2007. *Vaccine.* 25, 3080-84).

The infections caused by *A. baumannii* often occur in outbreaks caused by a single clone. For this reason, a vaccine based on OMVs could be more effective if the OMVs are isolated form the causative clone. The purification of OMVs from bacterial cultures is rapid and simple, requiring only filtering of the culture supernatant and concentration of the OMVs.

BRIEF DESCRIPTION OF THE INVENTION

Aspect A: This aspect of the invention refers to a pharmaceutical composition, preferably a vaccine composition, suitable for the prophylactic treatment (before infection) of an infection caused by an *Acinetobacter baumannii* strain in a mammal, which comprises:
  a. an *Acinetobacter baumannii* strain whole cell deficient in lipopolysaccharide (LPS) characterized by the partial or complete inactivation of one or various cellular nucleic acid molecules that encode endogenous LPS; and/or
  b. an outer membrane vesicle (OMV) derived from an *Acinetobacter baumannii* strain deficient in lipopolysaccharide (LPS) as defined in paragraph a) above.

In a prefer embodiment of this aspect of the invention, the *Acinetobacter baumannii* strain deficient in lipopolysaccharide (LPS) is characterized by the partial or complete inactivation of the genes selected from the list consisting of IpxA, IpxB and/or IpxC.

In another prefer embodiment of this aspect of the invention or of any of its preferred embodiments, the pharmaceutical composition, preferably the vaccine composition, further comprises a, preferably recombinant, polypeptide selected from the list consisting of:
  a. Aminoacid sequence SEQ ID No 27 (putative ferric siderophore receptor (*A. baumannii* ATCC 17978; accession number YP_001084684)) or a fragment thereof, wherein the term fragment is understood herein as biologically active fragments selected from the list consisting of SEQ ID No 1 to SEQ ID NO 11 or any combination thereof, or an amino acid sequence having at least 85% identity with any of sequences SEQ ID NO 1 to SEQ ID No 11; and/or
  b. Amino acid sequence SEQ ID No 28 (putative ferric hydroximate siderophore receptor (*A. baumannii* ATCC 17978; accession number YP_001084696)) or a fragment thereof, wherein the term fragment is understood herein as biologically active fragments selected from the list consisting of SEQ ID NO 12 to SEQ ID NO 23 or any combination thereof, or sequences that have at least 85% identity with the amino acids SEQ ID NO 12 to SEC ID NO 23.

In another prefer embodiment of this aspect of the invention or of any of its preferred embodiments, the pharmaceutical composition, preferably the vaccine composition, further comprises a purified outer membrane protein sequence of *A. baumannii* selected from the list consisting of: SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76, SEQ ID NO: 77, SEQ ID NO: 78, SEQ ID NO: 79, SEQ ID No: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, or any combination thereof.

In yet another prefer embodiment of this aspect of the invention or of any of its preferred embodiments, the pharmaceutical composition, preferably the vaccine composition, further comprises fusion recombinant polypeptides sequences SEQ ID NO 24 and/or 25 and/or the amino acid sequence coded by nucleotide sequence SEQ ID NO 26.

In yet another prefer embodiment of this aspect of the invention or of any of its preferred embodiments, the *Acinetobacter baumannii* strain deficient in lipopolysaccharide (LPS) comprises or is transformed, transduced or transfected with a nucleotide sequence capable of coding for any of the amino acid sequences as defined in any of the precedent paragraphs so that such strain is capable of producing the exogenous expression any of these amino acid sequences.

In yet another prefer embodiment of this aspect of the invention or of any of its preferred embodiments, said pharmaceutical composition, preferably the vaccine composition, further comprises a vector, such as viral vector, a plasmid or an expression cassette comprising a nucleotide sequence capable of coding for any of the amino acid sequences as defined in any of the precedent paragraphs and expressing said amino acid sequences.

In yet another prefer embodiment of this aspect of the invention or of any of its preferred embodiments, the *Acinetobacter baumannii* strain deficient in lipopolysaccharide (LPS) is inactivated. Preferably, said strain or cell is derived from ATCC strain 19606.

Aspect B: This aspect of the invention refers to the pharmaceutical composition, preferably the vaccine composition, of the aspect A of the invention or of any of its preferred embodiments, for use in the prophylactic treatment or for the active immunization of an infection caused by *A. baumannii* in a mammal, preferably in a human.

Aspect C: This aspect of the invention refers to a vaccine composition comprising an antibody (monoclonal or polyclonal) or a fragment thereof, preferably selected from the list consisting of Fab, Fab', Fab'-SH, Fv, scFv, F(ab')$_2$, Vhh, nanobody and diabody, having affinity or binding affinity against the *Acinetobacter baumannii* strain deficient in lipopolysaccharide (LPS) and/or against an outer membrane vesicle (OMV) derived therefrom. In a preferred embodiment, said antibody or fragment thereof specifically binds the *Acinetobacter baumannii* strain deficient in lipopolysaccharide (LPS) and/or to the outer membrane vesicle (OMV) derived therefrom.

"Affinity" or "binding affinity" KD are often determined by measurement of the equilibrium association constant (ka) and equilibrium dissociation constant (kd) and calculating the quotient of kd to ka (KD=kd/ka).

The term "specifically binding" means that the antibody binds to the LPS deficient strain or to the OMV derived therefrom with an affinity KD of lower than or equal to $10^{-6}$M (monovalent affinity). The antibody may have substantially greater affinity for the target antigen compared to other unrelated molecules. The antibody may also have substantially greater affinity for the target antigen compared to homologs, e.g. at least 1.5-fold, 2-fold, 5-fold 10-fold, 100-fold, $10^{-3}$-fold, $10^{-4}$-fold, $10^{-5}$-fold, $10^{-6}$-fold or greater relative affinity for the target antigen. Such affinities may be readily determined using conventional techniques, such as by equilibrium dialysis; by radioimmunoassay using radiolabeled target antigen; or by another method known to the skilled artisan. The affinity data may be analyzed, for example, by the method described in [Kaufman R J, Sharp P A. (1982) Amplification and expression of sequences cotransfected with a modular dihydrofolate reductase complementary dna gene. J Mol Biol. 159:601-621].

The term "antibody" is used in the broadest sense and includes fully assembled antibodies, monoclonal antibodies, polyclonal antibodies, multispecific antibodies (e.g., bispecific antibodies), antibody fragments that can bind the antigen (e.g., Fab', F'(ab)2, Fv, single chain antibodies, diabodies), camelbodies and recombinant peptides comprising the forgoing as long as they exhibit the desired biological activity.

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs.

The term "hypervariable" region refers to the amino acid residues of the variable domains VH and VL of an antibody or functional fragment which are responsible for antigen-binding.

Nonlimiting examples of antibody fragments include Fab, Fab', F(ab')2, Fv, domain antibody (dAb), complementarity determining region (CDR) fragments, single-chain antibodies (scFv), single chain antibody fragments, diabodies, triabodies, tetrabodies, minibodies, linear antibodies [Johnson G, Wu T T. (2000) Kabat database and its applications: 30 years after the first variability plot. Nucleic Acids Res. 28:214-218]; chelating recombinant antibodies, tribodies or bibodies, intrabodies, nanobodies, small modular immunopharmaceuticals (SMI Ps), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity; and multispecific antibodies formed from antibody fragments [Chothia C, Lesk A M. (1987) Canonical structures for the hypervariable regions of immunoglobulins. J Mol Biol. 196:901-917; Zapata G, Ridgway J B, Mordenti J, Osaka G, Wong W L, Bennett G L, Carter P. (1995) Engineering linear F(ab')2 fragments for efficient production in *Escherichia coli* and enhanced antiproliferative activity. Protein Eng. 8:1057-1062].

In a preferred embodiment of aspect C of the invention, the pharmaceutical or vaccine composition is obtained or obtainable after immunizing a mammal with the vaccine composition as defined in the first aspect of the invention.

Aspect D: This aspect of the invention refers to the vaccine composition as defined in aspect C of the invention, for use in the therapeutic treatment (after the infection), or in the passive immunization, of an infection caused by *A. baumannii* in a mammal, preferably in a human.

Aspect E: This aspect of the invention refers to an *Acinetobacter baumannii* strain deficient in lipopolysaccharide (LPS), transformed, transduced or transfected with a nucleotide sequence capable of coding for any of the amino acid sequences as defined in aspect A of the invention so that such strain is capable of producing the exogenous expression any of said amino acid sequences. Preferably, said *A. baumannii* deficient strain is use as a medicament.

Aspect F: This aspect of the invention refers to a method for the production of antibodies or fragments thereof, preferably selected from the list consisting of Fab, Fab', Fab'-SH, Fv, scFv, F(ab')$_2$, Vhh, nanobody and diabody, which comprises:

a. Selecting an antibody or a fragment thereof, preferably from an antibody library;
b. Using an *Acinetobacter baumannii* strain deficient in lipopolysaccharide (LPS) and/or an outer membrane vesicle (OMV) derived therefrom, as an antigenic target;
c. Selecting those antibodies or fragments thereof having affinity or binding affinity or capable of specifically binding such strain and/or OMV; and
d. Producing those antibodies or fragments thereof identified in step c) above It is noted, that Serotype specific variability in *A. baumannii* relies on variations in epitopes of the LPS component. By eliminating the LPS component according to the method as detailed in aspect F above, we focus the antibody raising to antibodies against less variable epitopes of the bacterial surface, not related to the LPS component. These epitopes are conserved among *A. baumannii* strains or individual isolates belonging to all *A. baumannii* international clones used in *A. baumannii* classification. This method thus provides the tools for a universal treatment against *A. baumannii* infections independently of the origin of the strain(s) responsible for the host infection.

Aspect G: This aspect of the invention refers to an antibody or fragment thereof produced, obtained or obtainable by the method of aspect F of the invention.

Aspect H: This aspect of the invention refers to the use of an *Acinetobacter baumannii* strain deficient in lipopolysaccharide (LPS) and/or an outer membrane vesicle (OMV) derived therefrom, for the production of antibodies or fragments thereof having affinity or binding affinity or capable of specifically binding such strain and/or OMV.

DETAILED DESCRIPTION OF THE INVENTION

The present invention refers to compositions and vaccines that consist of whole cells deficient in LPS and/or outer membrane vesicles of *Acientobacter baumannii* (*A. bau-* mannii) capable of conferring protection against infection caused by infectious pathogens.

The authors of the present invention demonstrate that inactivated cells of *A. baumannii* deficient in LPS and/or outer membrane vesicles from *A. baumannii*, upon being inoculated produce immunization, which provides protection against posterior infection by said bacteria, which demonstrates the utility of these cells or strains as prophylactic vaccines against infections caused by *A. baumannii*.

A first aspect of the present invention refers to an *Acinetobacter* cell or strain that is deficient in LPS, hereinafter cell or strain of the invention.

The species of *Acinetobacter* are strictly aerobic non-fermenting and non-motile bacilli that are oxidase negative and appear in pairs by microscopy. They are distributed widely in nature, and are important in soil and contribute to its mineralization.

It is understood that "inactivated cell" in the present invention is a cell that does not have the ability to replicate but that conserves its immunogenic capacity. The cells of the present invention are inactivated prior to their inoculation to prevent their replication in the host, and therefore prevent invention produced by their administration. The inactivation of the cells of the invention can be performed using diverse methods known in the state of the art for example, although not limited to, adsorption, heat, ultraviolet light, ionizing radiation, ultrasound, phenol, formol, formaldehyde, crystal violet, glyceraldehyde, ethylene oxide, propiolactone, ethylenamina, bromoethyleneamina or formalin. In a preferred embodiment, the cells of the invention are inactivating with formalin. In another preferred embodiment the cells of the invention are from the species *Acinetobacter baumannii* and they are inactivated with formalin.

In a preferred embodiment of this aspect of the invention, the deficiency in LPS can be achieved by partial or complete inactivation of one or various cellular molecules of nucleic acids that encode the endogenous genes for the LPS subunits, particularly IpxA, IpxB and/or IpxC of LPS.

In another preferred embodiment of the invention, the cell or strain of *Acinetobacter* deficient in LPS is obtained by deletions and/or insertions of one or various nucleotides in nucleic acid sequences encoding the gene involved in the biosynthesis of LPS and/or the sequences that control their expression. The deletions and/or insertions can be generation by homologous recombination, insertion of transposons, or other adequate methods known in the state of the art.

In preferred embodiment of the invention, the sequence is inactivated e.g by construction of a suicide vector that contains the gene IpxA, IpxB, IpxC, IpxD, IpxK, IpxL and/or IpxM or any of their combination, or interrupting with a marker gene for selection, transforming the target cells with the vector and screening for positive cells that are negative for LPS expression.

In another preferred embodiment of the invention, the cell or strain of the invention is preferably an *A. baumannii* cell, particularly an attenuated *A. baumannii* cell or other *Acinetobacters*; *Acinetobacter baylyi, A. beijerinckii, A. bereziniae, A. boissieri, A. bouvetii, A. brisouii, A. calcoaceticus, A. gerneri, A. guillouiae, A. grimontii, A. gyllenbergii, A. haemolyticus, A. indicus, A. johnsonii, A. junii, A. lwoffii, A. nectaris, A. nosocomialis, A. parvus, A. pittii, A. puyangensis, A. radioresistens, A. rudis, A. schindleri, A. soli, A. tandoii, A. tjernbergiae, A. towneri, A. ursingii* or *A. venetianus*.

In this report, it is understood that *Acinetobacter* refers to the kingdom Bacteria, phylum Proteobacteria, class Gammaproteobacteria, order Pseudomonadales, family Moraxellaceae.

It is understood that "cells or strains of the *Acinetobacter baumannii*" in the present invention are those cells pertaining to the domain Bacteria, phylum Proteobacteria, class Gammaproteobacteria, order Pseudomonadales, family Moraxellaceae, genus *Acinetobacer*, species *Acinetobacter baumannii*.

It is understood that "lipopolysaccharide (LPS) or lipooligosaccharide" is a component that is found on the external membrane of various Gram-negative bacteria. The term LPS is used often and interchangeably with "endotoxin", due to its history of discovery. LPS consists of a polysaccharide chain and the rest is lipid, known as lipid A, which is responsible for the endotoxin activity. The polysaccharide chain is variable between different bacterias and determines the serotype. Endotoxin is of approximately 10 kDa in size, but can form large aggregates of up to 1000 kDa. Humans are able to produce antibodies against LPS, but in general these antibodies can only protect against bacteria of a specific serotype. Endotoxin is responsible for many of the clinical manifestations of infections caused by Gram-negative bacteria such as *Neisseria meningitidis* and *Acinetobacter baumannii*.

Composition of the Invention

A second aspect of the invention refers to a composition, hereinafter composition of the invention comprising:
  a) a cell or strain of the invention, and
  b) optionally a sequence of nucleotides and/or amino acids or polypeptides.

In a more preferred embodiment of this aspect of the invention, the nucleic acid and/or the amino acid sequence or polypeptide is recombinant.

In a still more preferred embodiment, the polypeptide is selected from
  I) the peptide sequence SEQ ID NO: 27 (putative ferric siderophore receptor (*A. baumannii* ATCC 17978; accession number YP_001084684)) or a fragment thereof, wherein the fragments are biologically active fragments, preferably selected from the list consisting of SEQ ID NO: 1 to SEQ ID NO: 11, or any of its combinations, or sequences having at least 85% sequence identity with the peptide sequences SEQ ID NO: 1 to SEQ ID NO: 11, and/or
  II) the peptide sequence SEQ ID No 28 (putative ferric hydroximate siderophore receptor (*A. baumannii* ATCC 17978; accesión number YP_001084696)) or a fragment thereof, wherein the fragments are biologically active fragments, preferably selected from the list consisting of SEQ ID NO: 12 to SEQ ID NO: 23, or any of its combinations, or sequences having at least 85% sequence identity with the peptide sequences SEQ ID NO: 12 to SEQ ID NO: 23.

In a still more preferred embodiment, the composition of the invention comprises the amino acid sequence SEQ ID NO: 28 and the amino acid sequence SEQ ID NO: 27.

In another preferred embodiment, the composition of the invention comprises a fusion protein that consists of at least 2, preferably 3, more preferably 4, amino acid sequences from the following list consisting of: SEQ ID NO: 1 to SEQ ID NO: 23 or a variant of these sequences having at least 85% identity with the sequences SEQ ID NO: 1 to SEQ ID NO: 23.

In another preferred embodiment, the fusion protein comprises the amino acid sequence SEQ ID NO: 24 or the amino acid sequence SEQ ID NO: 25.

In another preferred embodiment, the composition of the invention comprises a nucleotide sequence, hereinafter nucleotide sequence of the invention, capable of transcribing an amino acid sequence described in the invention. More preferably, the nucleotide sequence is SEQ ID NO: 26.

The fragments described previously differ in amino acid sequence by at least one amino acid. The most preferred variations are those having at least 85%, or more, including 90%, 93% or more, and preferably 95% or more, 96% or more, 97% or more, 98% or more, 99% or more of sequence identity with any of the polypeptides shown in SEQ ID NO:1 to SEQ ID NO:25. More preferably, the invention refers to a sequence variant characterize by at least one (at least two, at least three, at least four) mutation(s) in relation to any of the polypeptides SEO ID NO:1 to SEC ID NO:25. In agreement with the invention as described in the descriptive section, mutation can refer to any mutation selected by insertion(s), deletion(s), and substitution(s). Preferably substitution(s).

In another preferred embodiment, the composition of the invention comprises an expression vector (hereinafter expression vector of the invention), comprising a nucleotide sequence of the invention.

In another preferred embodiment, the composition of the invention also comprises outer membrane vesicles, hereinafter outer membrane vesicles of the invention, deficient in LPS.

In another preferred embodiment, the composition of the invention also comprises at least one or the proteins purified from the membrane of *A. baumanni* with amino acid sequence SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, y SEQ ID NO: 89, or any of their combinations.

More preferably, at least one of the proteins of the outer membrane of *A. baumannii* is obtained by a process comprising:

a. Inoculating one liter of Mueller-Hinton broth with a colony of *A. baumannii* ATCC 19606;
b. incubating the culture until an optical density of 0.6 at 600 nm;
c. Washing bacterial cells with 30 ml of 10 mM phosphate buffer pH, 7.2;
d. Centrifuge at 6000×g for 10 min;
e. Resuspend the bacterial pellet sin 10 ml of 10 mM phosphate buffer pH 7.2 and lysing by sonication 5 times for 1 minute;
f. Eliminate unlysed cells by centrifugation at 6000×g for 5 minutes;
g. Centrifuge the supernatant at 4° C. at 20000×g for one hour;
h. Eliminate proteins of the external membrane by solubilising with 5 ml of 2% N-lauraylsarcosinante in 10 mM phosphate buffer pH 7.2 for 30 minutes at 37° C.;
i. Precipitate the insolube fraction (that contains the outer membrane proteins) by centrifuging at 4° C. at 20000×g for one hour;
j. Wash the pellet once with 2 ml 62.5 mM Tric-HCl ph, 6.8 and centrifuge at 4° C. for one hour;
k. Resuspend the pellet in a solution of 5% SDS and precipitate with methanol/chloroform; and
l. Resuspend the pellet in sterile PBS.

In another preferred embodiment of the invention, the composition of the invention is a pharmaceutical composition, more preferably also comprises an acceptable pharmaceutical vehicle, and still more preferably, also comprises another active ingredient.

In another preferred embodiment, the composition of the invention also comprises an adjuvant. In another preferred embodiment, the composition of the invention is a vaccine.

In the context of the present invention, the term "vaccine" refers to an antigenic preparation employed for inducing an immune response to a disease. They are prepared from antigens that, once inside the host, provoke an immune response through the production of antibodies, and generate immunologic memory producing transient or permanent immunity. It is noted that as used herein the term "vaccine" can also be understood as a preparation from antibodies or fragments thereof suitable for the therapeutic treatment or for passive immunization of an infection caused by an *Acinetobacter* strains, in particular from an *A. baumannii* strain.

Nucleotide Sequence and Expression Vector

A third aspect of the invention refers to a nucleotide sequence, hereinafter second nucleotide sequence of the invention, which encodes any of SEQ ID NO 1 to 25, 27 or 28 or any combination thereof. Said second nucleotide sequence of the invention also includes nucleic acid sequence SEQ ID NO: 26.

A fourth aspect of the invention refers to an expression vector, hereinafter expression vector of the invention, comprising the second nucleotide sequence of the invention.

In a preferred embodiment of this aspect, the cell of the invention comprises the expression vector of the invention.

The nucleic acid can be localized in a recombinant vector. Preferably, the recombinant vector is a prokaryotic vector, that is a vector that contains elements for replication and/or integration into the genome of prokaryotic cells. Preferably, the recombinant vector contains the nucleic acid molecule of the present invention operatively linked to an expression control sequence. The control sequence is preferably a sequence controlling the active expression in *Acinetobacter*, particularly in *A. baumannii*. The vector can be an extrachromosomic vector adequate for integration in the chromosome. Examples of such as vectors are known by experts in the field, for example in Sambrook et al. supra.

Outer Membrane Vesicles of the Invention

A fifth aspect of the invention refers to an outer membrane vesicle that is deficient in LPS. In a preferred embodiment of this aspect, the outer membrane vesicle is obtained from the cell or strain of the invention.

Use of the Cells, Vesicles and the Compositions of the Invention

A sixth aspect refers to the composition of the invention for use as a medicament, or alternatively, to the use of the composition of the invention for the manufacture of a medicament.

The term "medicament" or "pharmaceutical composition" as used in this report, makes reference to any substance used for the prevention, alleviation, treatment or cure of a disease in man or animals. The context of the present invention refers to a composition comprising the composition of the invention. This composition of the invention comprises inactivated cells of the genus *Acinetobacter* and/or outer membrane vesicles of the same in a quantity therapeutically effective, that is able to inducer an immune response in the organism in which they are administered against an organism of the genus *Acinetobacter*. The term "medicament" or "pharmaceutical composition" therefore is known as a vaccine.

The dosing for obtaining the effective therapeutic quantity depends on a variety of factors such as for example, age, weight, sex, tolerante, . . . of the mammal. As used in this description, the "effective therapeutic quantity" refers to the quantity of inactive cells of the genus *Acinetobacter* and/or outer membrane vesicles that produce the desired effect, and in general are determined by the therapeutic effect that is desired.

A seventh aspect of the invention refers to the composition of the invention for the prevention, the improvement or the treatment of an infection caused by *A. baumannii*, en a mammal, or alternatively, to the use of the composition of the invention for the elaboration of a medicament for the prevention, improvement or treatment of an infection caused by *A. baumannii* in a mammal.

It is understood by "disease produced by organisms of the genus *Acientobacter*" those diseases in which the causal agent of the pathology is from the genus *Acinetobacter*, or any of its metabolic products. The genus *Acinetobcter* produces diverse pathologies for example but not limited to, bacteremia, meningitis, urinary tract infections, skin and soft tissue infections, surgical site infections and pneumonia. For these reasons, one of the more preferred forms, diseases produced by organisms of the genus *Acinetobacter* are selected from a list that consists of bacteremia, meningitis, urinary tract infections, skin and soft tissue infections, surgical site infections and pneumonia.

The medicaments and compositions of the invention can be used alone or in combination with other medicaments or compositions for the treatment of diseases produced by organisms from the genus *Acinetobacter*.

Both the medicaments and the compositions of the invention can also include pharmaceutically acceptable vehicles or excipients The medicaments and compositions of the invention may be used either alone or in combination with other medicaments or compositions for the treatment or prevention of diseases caused by organisms of the genus *Acinetobacter.*

The term "excipient" makes reference to a substance that helps in the absorption of the elements of the composition of the medicaments of the invention, stabilizing said elements, activating or helping the preparation of the medicament such that it provides consistency or flavours that make it more palatable. The excipeints can maintain the ingredients together, like for example is the case with starches, sugars, cellulose, sweetners, coloring agents, the function of protecting the medicament, for example isolating it form air and/or humidity, the function of filling the pill, capsule or any other form of presentation, for example, the case of dibasic calcium phosphate, the function for facilitating dissolution of the components and their absorption in the intestine, without excluding other types of excipients described in this paragraph.

The vehicle, in the same way as the excipient, is a substance that is used in the medicament to dilute any of the components of the present invention to a desired volume or weight. The pharmaceutically acceptable vehicle is an inert substance or of similar action to any of the elements of the present invention. The function of the vehicle is to facilitate the incorporation of other elements, permit better dosing and administration and give consistency and form to the medicament. When the form of presentation is liquid, the pharmaceutically acceptable vehicle is the diluent.

The adjuvants and pharmaceutically acceptable vehicle that can be used in the composition of the invention are those vehicles known by experts in the field.

In this report, the term "adjuvant" refers to any agent that does not poses antigenic activity in and of itself, that can be used to stimulate the immune system to increase the response to a vaccine. There are many adjuvants, for example but not limited to, aluminium phosphate, aluminium hydroxide, toll-like receptor agonists, cytokines, squaline, Freunds incomplete and complete adjuvants. In a preferred form of this aspect of the invention, the adjuvant is selected for a list that consists of aluminium phosphate, aluminium hydroxide, toll-like receptor agonists, cytokines, squaline, Freunds incomplete and complete adjuvants. In a still more preferred form of this aspect of the invention, the adjuvant is aluminium phosphate.

As used here, the term "active ingredient", "active substance" or "pharmaceutically active substance" or "pharmaceutically active ingredient" refers to any component that potentially provides pharmacological activity or other different effect in the diagnosis, cure, alleviation, treatment or prevention of a disease or that affects the structure or function of the human or animal body. The term includes those components that promote a chemical change in the elaboration of the drug and are present in the same and a modified form that provides specific activity or the effect.

An eighth aspect of the invention refers to the composition of the invention for conferring protection against an infection caused by *A. baumannii* en a mammal, or alternatively, the use of the composition of the invention in the elaboration of a medicament for conferring protection against an infection caused by *A. baumannii* in a mammal.

Another aspect of the invention refers to the fusion protein or peptide of the invention or the composition of the first or second aspect of the invention or the pharmaceutical composition of the invention that can be administered once or various, such as two, three, four, five, six, seven, eight, nine or ten or more times. There are no particular limitations relative to the quantity of the active ingredient per dose.

An additional aspect of the present invention refers to a composition that consists of an antibody or fragment thereof that is capable of binding to SEQ ID NO: 27 or SEQ ID NO: 28 or a fusion protein as defined in the second aspect or the fusion protein of the invention, wherein preferably said composition is a pharmaceutical composition, preferably a vaccine, and wherein said pharmaceutical composition is used in the treatment or prevention of an infection caused by *A. baumannii*.

A ninth aspect of the invention refers to an antibody or an active fragment thereof obtainable by immunization of a mammal with the composition of the first or second aspect of the invention or with the fusion protein of the invention, preferably said antibody or active fragment consists of a composition in which preferably said composition is a pharmaceutical composition and said pharmaceutical composition is used as a therapy, particularly for the treatment of infections caused by *A. baumannii*.

Method for Preparing an *Acinetobacter* Cell Following the Invention

A tenth aspect of the invention refers to a method for preparing a cell of *A. baumannii* as described above.

*Acinetobacter*

In agreement with this aspect, this method consists of the steps to (i) provide a bacterial cell deficient in LPS, particularly a cell of *Acinetobacter*, (ii) insert a recombinant nucleic acid molecule in said bacterial cell, encoding said nucleic acid molecule a fusion peptide that consists of (a) at least on domain of the polypeptide wherein said domain is capable of producing an immune response in mammal and (b) a domain of escape for the phagolysosome, and (iii) culture the obtained cell in agreement with step (ii) in adequate conditions. Preferably, a cell capable of expressing said nucleic acid is obtained. More preferably, the cell is a cell of *A. baumannii.*

In agreement with the additional aspect, this method consists of step of (i) providing a bacterial cell deficient in LPS, particularly an *Acinetobacter* cell, (ii) inserting a recombinant nucleic acid molecule in said bacteria, encoding said nucleic acid molecule a peptide or polypeptide for escape from the phagolysosome, and (iii) culture the obtained cell in agreement with step (ii) in adequate conditions.

If desired, the method of the present invention consists of inserting at least one recombinant nucleic acid molecule in the bacterial cell, said molecule encoding a peptide or polypeptide capable of producing an immune response in mammals.

It is understood that "infection" in the present invention is that pathology generated by the invasion or colonization of any host tissue by any organisms of the genus *Acinetobacter*, preferably *Acinetobacter baumannii.*

It is understood that "soft tissue" in the present invention, is all non-bony tissue of an organism.

The term "prevention" as understood in the present invention consists of avoiding the appearance of damage whose cause is cells of the genus *Acinetobacter*, or any derivative or metabolic product of the same.

The term "antigen" in the report refers to a molecule (generally a protein or polysaccharide) that can induce the formation of antibodies. There many different types of molecules that can act as antigens, such as proteins, peptides, polysaccharides, and more rarely other molecules such as nucleic acids.

The term "resistance" refers to any mechanism of defense developed by bacteria against a drug. The mechanisms of resistance acquired and transmitted by bacteria are the most important and consist primarily of: the production of enzymes that inactivate antibiotics, appearance of modifications that impede the arrival of the drug to its target and/or alteration of the target itself. One bacterial strain can develop various resistance mechanisms against one or many antibiotics and in the same way an antibiotic can be inactivated by distinct mechanisms from diverse bacterial species.

The terms "polynucleotide" and "nucleic acid" are used interchangeably, referring to polymeric forms of nucleotides of any length, both of DNA and RNA The terms "amino acid sequence", "peptide", "oligopeptide", "polypeptide" and "protein" are used interchangeably, and refer to a polymeric form of amino acids of any length that can be chemically or biochemically modified.

During the description of the claims, the word "comprising" and its variants does not intend to exclude other technical characteristics, additives, components or steps. For those expert in the state of the art, other objects, advantages and characteristics of the invention are released in the section of the description and practice of the invention. The following examples and drawings are provided as illustrations, and are not intended to limit the present invention.

DESCRIPTION OF THE FIGURES

FIGS. 1A and 1B. Stability and endotoxin content of IB010. (FIG. 1A) Genomic DNA from three independent cultures of ATCC 19606 and IB010 was extracted and amplified using primers specific for the IpxD gene. The band corresponding to approximately 1000 Kb corresponds to the intact IpxD gene, whereas the faster migrating band corresponds to the IpxD gene with a deletion of 462 nucleotides. (FIG. 1B) Endotoxin levels of ATCC 19606 and 16010 determined by the Limulus Amebocyte Assay. Bars represent the median values of three independent cultures, and error bars represent the standard error of the mean. EU; endotoxin units.

FIGS. 2A-2D. Antibody response to immunization with IB010. Serum samples were collected from ATCC 19606 vaccinated, IB010 vaccinated and control mice before vaccination (Day 0) and at day 7 and 21 after the first immunization, and levels of antigen specific total IgG (FIG. 2A) and IgM (FIG. 2B) were measured by ELISA (n=8 mice/group). IgG1 (FIG. 2C) and IgG2c (FIG. 2D) levels were measured in 21-day serum were measured by ELISA in ATCC 19606 vaccinated, IB010 vaccinated and control mice. In all panels box and whisker plots represent the interquartile ranges and ranges, respectively, and horizontal lines represent median values. *$p<0.05$ compared to levels in control mice at the same time point, #$p<0.05$ compared to 7-day samples from the same experimental group, †$p<0.05$ compared to 21-day samples in ATCC 19606 vaccinated mice.

FIG. 3. Effect of vaccination on tissue bacterial loads. Immunized and control mice were infected with $2.0\times10^6$ cfu ($300\times LD_{50}$) of the ATCC 19606 strain and spleen bacterial loads were determined 12 hours post-infection (n=8 mice/group). Data points represent bacterial loads from individual mice, and horizontal lines represent median values from groups of mice. *$p<0.05$ compared to control mice.

FIG. 4. Effect of vaccination on post-infection pro-inflammatory cytokine levels. Immunized and control mice were infected with $2.0\times10^6$ cfu ($300\times LD_{50}$) of the ATCC 19606 strain and serum levels of IL-1β, TNF-α, and IL-6 were determined (n=8 mice/group). Data points represent cytokine levels from individual mice, and horizontal lines represent median values from groups of mice. *$p<0.05$ compared to control mice, #$p<0.05$ compared to ATCC 19606 vaccinated mice.

FIGS. 5A and 5B. Effect of vaccination on survival in a mouse model of disseminated *A. baumannii* infection. Vaccinated and control mice were infected with $2.25\times10^6$ cfu ($340.9\times LD_{50}$) of the ATCC 19606 strain (FIG. 5A) or $1.05\times10^6$ cfu ($2.18\times LD_{50}$) of the *A. baumannii* clinical isolate Ab-154 FIG. 5B), and survival was monitored over the following 7 days (n=8 mice/group). *$p<0.05$ compared to control mice.

FIG. 6. Protein profile of the *A. baumannii* OMVs without LPS. The strains ATCC 19606 and IB010 for the production of OMVs after culturing 24, 48 and 72 hours. After the purification of OMVs the amount of protein was quantified using Bradford method and 10 mcg of the protein was visualized in a 10% polyacrylamide gel with Coomassie stain.

Figure 7:
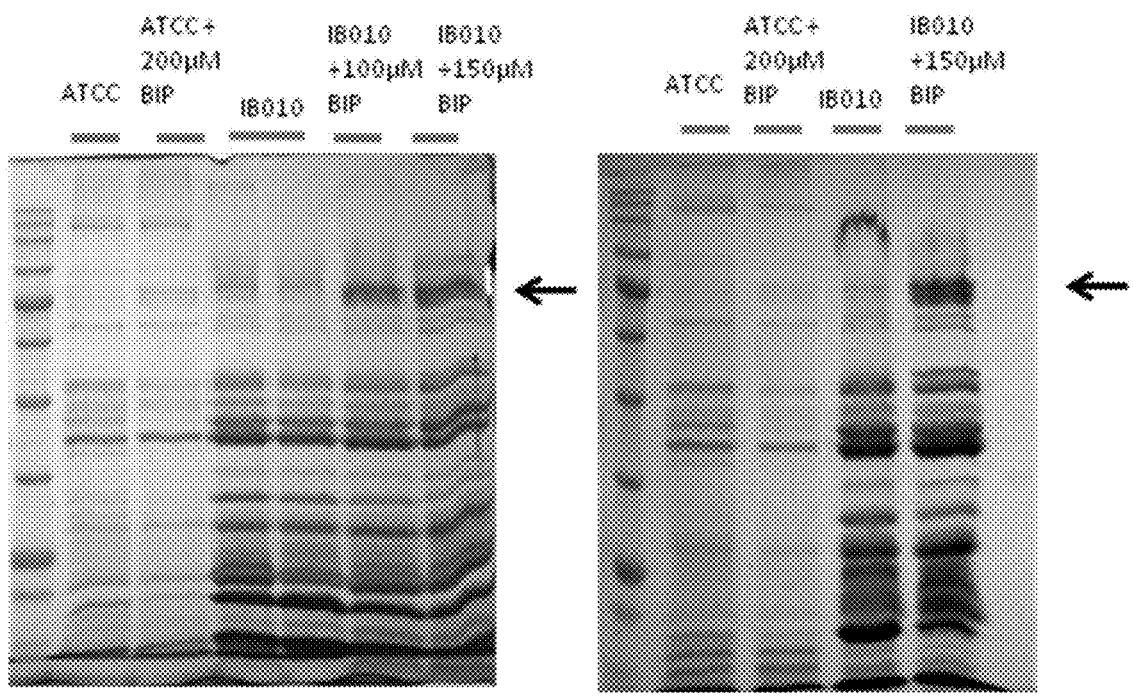

FIG. 7. Effect of 2,2 Bipyridyl, iron chelator, in the protein profile of OMVs. The strains ATCC 19606 and IB010 were used to analyze the effect of 2,2 bypiridyl (BIP) on the protein profile of the eOMVs after culturing for 24 hours. In the case of the ATCC 19606 strain a concentration of 200 mcM was used while in the case of IB010 100 and 150 mcM was used. After the purification of OMVs the amount of protein was quantified using Bradford method and 10 mcg of the protein was visualized in a 10% polyacrylamide gel with Coomassie stain.

FIG. 8. Effect of 2,2 Bipyridyl, iron chelator, on the production of OMVs. The strains ATCC 19606 and IB010 were used to analyze the effect of 2,2 bypiridyl (BIP) on the production of the OMVs after culturing for 24 hours. In the figure the total protein content of the OMVs is shown after treatment with Bip and measuring the concentration with Bradford.

Figure 9:
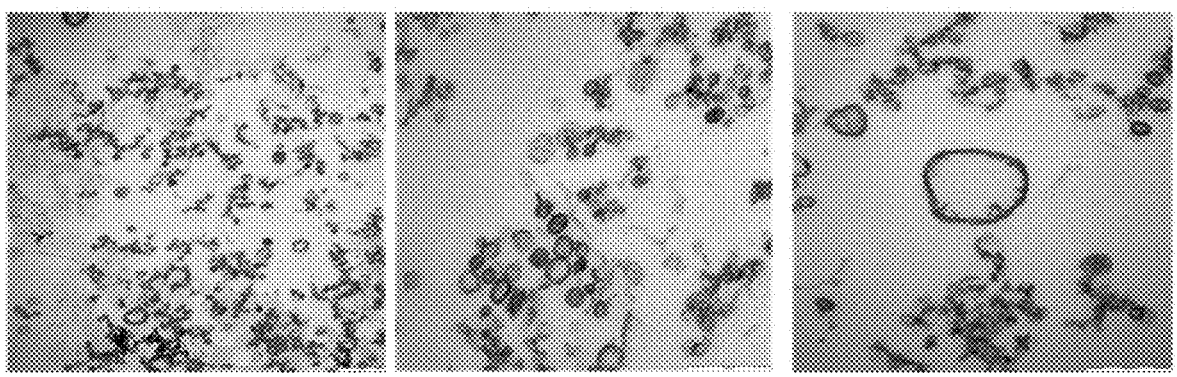
Figure 9:
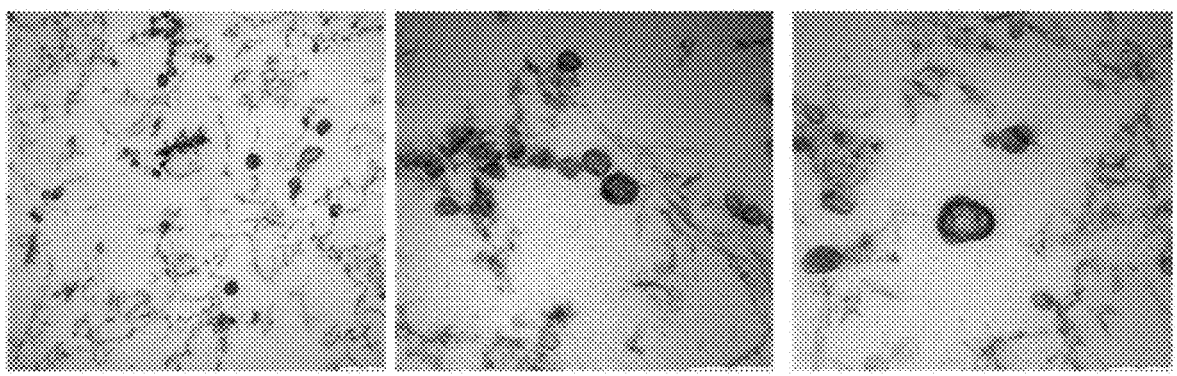

FIG. 9. Visualization of OMVs. OMVs purified form ATCC 19606 were fixed using glutaraldehyde at 1.6% and stained with osmium tetroxide and lead and uranium and visualized by electron microscopy.

Figure 10:
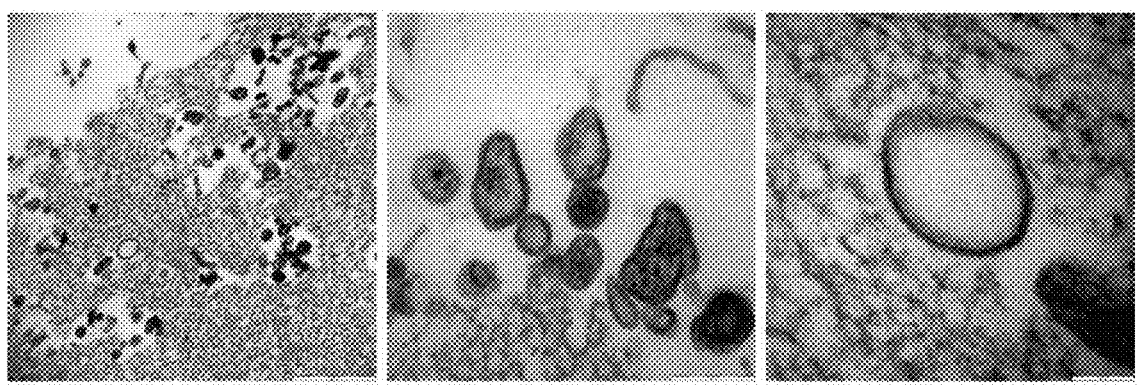
Figure 10:
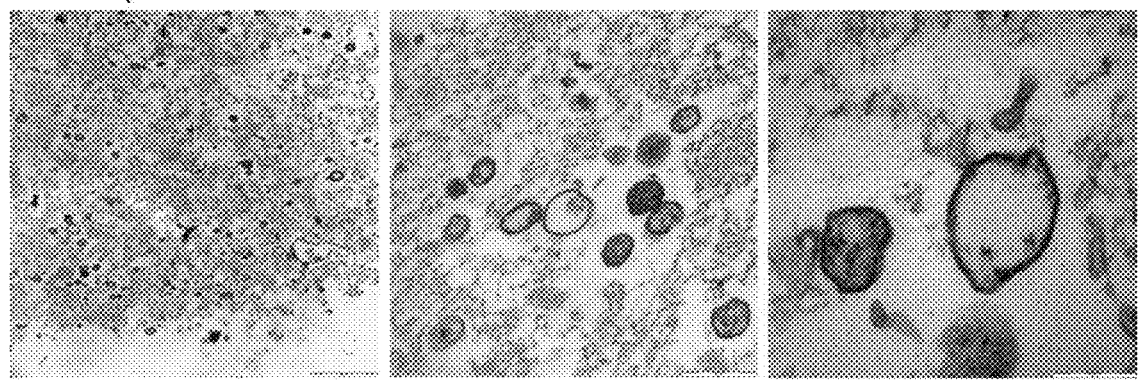

FIG. 10. Visualization of purified OMVs. OMVs purified form IB010 were fixed using glutaraldehyde at 1.6% and stained with osmium tetroxide and lead and uranium and visualized by electron microscopy.

Figure 11:
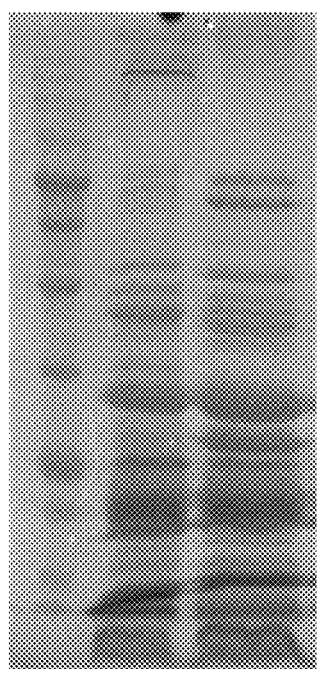

FIG. 11. Protein profile of OMVs without LPS. The strains IB010 and 167R were used to produce OMVs and the amount of protein was quantified from each sample. Ten mcg of the protein was visualized in a 10% polyacrylamide gel with Coomassie stain.

EXAMPLES OF THE INVENTION

Example 1

Ethics Statement

All experiments involving the use of animals were approved by the University Hospital Virgen del Rocío Committee on Ethics and Experimentation (Evaluation code: 2013PI/296). In all experiments, efforts were made to minimize suffering, and any animals appearing moribund during the course of experimentation were immediately euthanized using thiopental.

Bacterial strains. *A. baumannii* ATCC 19606 is an antibiotic susceptible reference strain. An LPS-deficient derivative of ATCC 19606 was obtained by plating an overnight culture of ATCC 19606 on Mueller Hinton agar containing 10 mg/l of colistin, as described previously (Clinical Laboratory Standards Institute 2013) Strains with mutations in the genes involved in LPS biosynthesis were identified by sequencing the IpxA, IpxC and IpxD genes of the colistin resistant mutants that were present after overnight growth at 37° C. A strain with a large deletion in the IpxD gene was identified and designated IB010. Resistance to colistin was confirmed by broth microdilution according to Clinical Laboratory Standard Institute guidelines [23]. Absence of LPS was confirmed by measuring the endotoxin levels of three independent cultures of each strain using the QCL-1000 Limulus Amebocyte Assay (Lonza) according to the manufacturer's instructions. The Ab-154 strain is a previously characterized *A. baumannii* clinical isolate (Gautom, 1997. *J. Clin. Microbiol.* 35, 2977-2980).

Vaccine preparation and mouse immunization. The IWC vaccines (both LPS-containing and LPS-deficient) were prepared as described based on a previously described method (Moffatt et al., 2010. *Antimicrob. Agents Chemother.* 54, 4971-4977). Briefly, the ATCC 19606 and IB010 strains were grown in Mueller-Hinton broth to $OD_{600}$ of 0.8. In the case of IB010, 10 µg/ml of colistin were added to the culture. In order to confirm that no reversion to wild type occurred during growth of IB010, three independent cultures of ATCC 19606 and IB010 were grown, and genomic DNA was isolated from each culture using the QIAmp DNA Mini Kit (Qiagen). The IpxD specific primers 5' GCTAATTGGT-GAAGGTAGTC 3' and 5' GACGAATCGTTTGAATCTGC 3' were used to amplify genomic DNA from the cultures in order to confirm that the deletion in IpxD of IB010 was present after growth.

For vaccine preparation, bacteria were washed extensively in phosphate buffer saline before inactivation in 0.5 M formalin for 18 h with shaking at room temperature. Complete inactivation of the bacteria was confirmed by plating on blood agar. The concentration of inactivated cells was adjusted to $1 \times 10^{10}$ cells/ml and combined 1:1 (v/v) with the aluminium-based adjuvant, Alhydrogel 2% (w/v) (Invivo-Gen). Vaccination was carried out in 6 to 8-week-old, female C57BL/6 mice by intramuscular injection of 100 µl of the vaccine into each quadriceps muscle on days 0 and 14. Control mice were injected similarly with a mixture of phosphate buffer saline and adjuvant.

Mouse model of *A. baumannii* infection. A mouse model of sepsis previously developed by our group and used for the evaluation of vaccines against *A. baumannii* was used to characterize the efficacy of the (Batson et al., 1950. *J. Exp. Med.* 91, 219-229; Rodríguez-Hernández et al., 2000. *J. Antimicrob. Chemother.* 45, 493-501). This model produces a disseminated infection after intraperitoneal instillation of the inoculum, typically resulting in death within 24 to 48 hours. For preparation of the inocula, *A. baumannii* strains were grown for 18 h at 37° C. in Mueller-Hinton broth cultures and adjusted to the appropriated concentration in physiological saline as described previously (Moffatt et al., 2010. *Antimicrob. Agents Chemother.* 54, 4971-4977; Martin et al., 1998. *J. Immunol. Methods* 212, 187-192). Bacterial concentrations of the inocula were determined by plating on blood agar. Mice were infected on day 21 (one week after the second immunization) by intraperitoneal injection with 0.5 ml of the bacterial suspension and survival was monitored for 7 days.

Spleen bacterial loads and serum cytokine levels. Post-infection bacterial loads were determined in vaccinated and control mice 12 h after infection. Mice were euthanized with an overdose of thiopental and after collection of blood samples from the retro-orbital sinus, spleens were aseptically removed, weighed and homogenized in 2 ml of physiological saline. Serial log dilutions were plated on blood agar plates for bacterial quantification. Serum levels of interleukin-1β (IL-1β), tumor necrosis factor alpha (TNF-α), and interleukin-6 (IL-6) were determined in mice at 12 h post-infection using BD OptEIA mouse kits (BD Biosciences).

Enzyme-linked immunosorbent assays (ELISAs). For indirect enzyme-linked immunosorbent assays (ELISAs), 96-well plates were coated with $5 \times 10^7$ bacterial cells/well in phosphate buffer saline by incubating at 4° C. overnight. ELISAs were performed using sera collected on days 0, 7 and 21 as described previously [28]. Antibody titers were measured against the strain which was used to immunize the mouse, and were defined as the dilution in which spectrophotometric readings were at least 0.1 units above background wells (wells containing no serum).

Statistical analysis. Antibody titers, bacterial loads, and cytokine levels were compared using the Kruskal-Wallis H test and the Mann-Whitney U test for independent samples, and the Friedmann and Wilcoxon tests for dependent samples. The Bonferroni correction was applied when appropriate. Survival data were compared using the log-rank test. All statistics were performed using SPSS version 15.0 software (SPSS Inc.), and a p value of 0.05 was considered significant.

Results

Figure 1B:
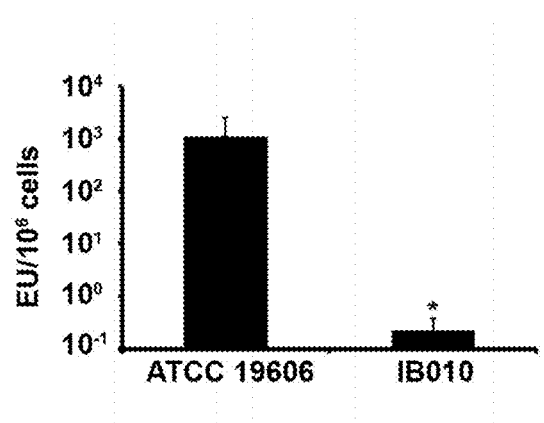

Selection of an LPS-deficient strain for vaccine development. Growth of ATCC 19606 in the presence of 10 µg/ml colistin resulted in numerous colistin-resistant derivatives with mutations in the IpxA, IpxC and IpxD genes (data not shown). One of these strains, IB010, contained a large deletion of 462 nucleotides in the IpxD (nucleotides 104-565) gene and was chosen for further use in vaccine studies. We reasoned that on the basis that the strain contained a large deletion, this strain would be less likely to revert to wild type during growth than strains containing single nucleotide changes or small deletions in the LPS biosynthesis genes. Broth microdilution experiments demonstrated that the minimum inhibitory concentration of the ATCC 19606 strain was 0.25 µg/ml and >128 µg/ml for IB010, demonstrating that, similar to results described previously, mutations in IpxD can result in resistance to colistin (Moffatt et al., 2010. *Antimicrob. Agents Chemother.* 54, 4971-4977). In order to ensure that the IB3010 was genetically stable during growth, genomic DNA from three independent cultures of ATCC 19606 and IB010 were amplified with IpxD-specific primers to confirm that the deletion was present. As shown in FIG. 1A, a band corresponding to the mutated IpxD gene of IB010 containing a deletion of 462 nucleotides was present after amplification from all IB010 cultures indicating that no reversion had occurred. Phenotypic loss of LPS and reduction in endotoxin levels were characterized by the Limulus Amebocyte Assay for ATCC 19606 and IB010, and demonstrated that mutation in the IpxD gene resulted in a dramatic reduction in endotoxin levels to >1 EU per $10^6$ cells (FIG. 1B).

Figure 2A:
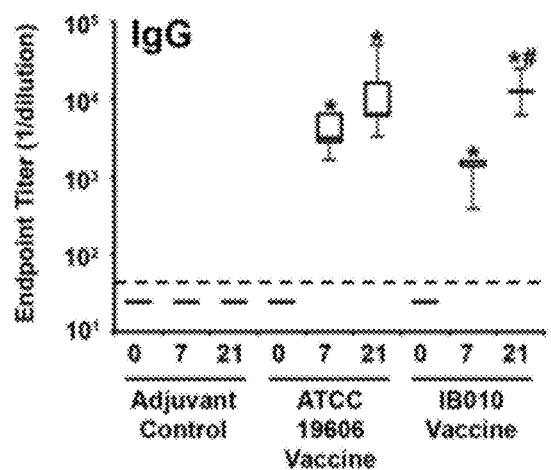
Figure 2B:
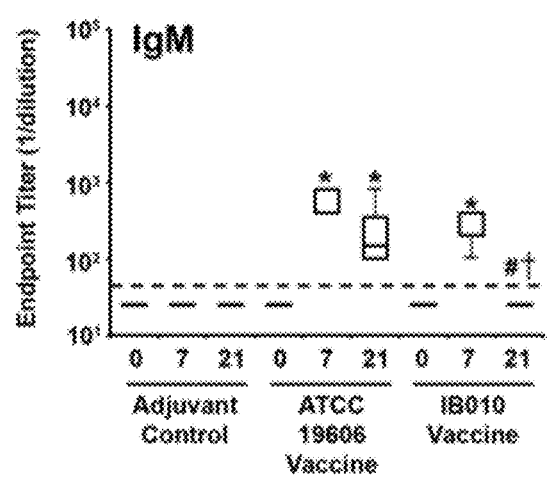

Antibody response to the LPS-deficient IWC vaccine. Formalin treatment of ATCC 19606 and IB010 resulted in no viable bacteria, indicating complete bacterial inactivation. In order to quantify the antibody response produced by immunization with inactivated IB010, indirect ELISAs were performed using sera collected from negative control mice (immunized with PBS and adjuvant) and mice vaccinated with $1 \times 10^9$ inactivated IB010 cells. As a positive control, one group of mice was immunized with $1 \times 10^9$ inactivated ATCC 19606 cells on the basis that we have previously shown that immunization with these cells induces a robust immune response and produces protective immunity against experimental infection (McConnell y Pachón, 2010. *Vaccine* 29, 1-5). As shown in FIG. 2A, immunization with inactivated IB010 elicited detectable levels of antigen-specific total IgG in all mice seven days after a single intramuscular administration, and these antibody levels were significantly increased upon boosting with a second administration of the vaccine (p=0.03 Wilcoxon test). Total IgG titers in mice receiving two administrations of inactivated IB010 vaccine were similar to titers in mice receiving the vaccine containing inactivated wild type cells (p=0.726 Mann Whitney U test). Control mice had no detectable antigen-specific IgG at any point. In contrast, IgM levels were similar between mice immunized with the inactivated IB010 vaccine and mice receiving inactivated wild type cells seven days after a single administration (p=0.186 Mann Whitney U test), however seven days after a second immunization there was no detectable antigen-specific IgM in IB010-vaccinated mice whereas all mice immunized with inactivated wild type cells had detectable levels of IgM (FIG. 2B).

Figure 2C:
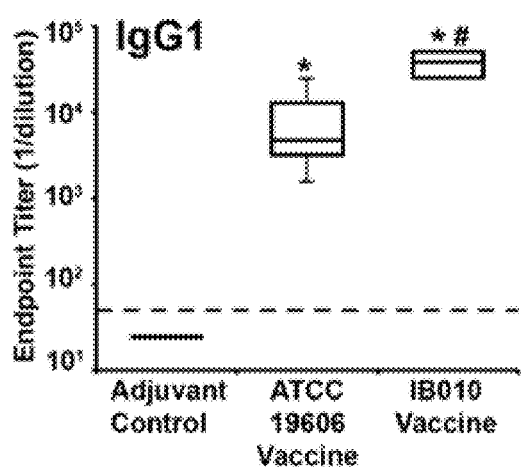
Figure 2D:
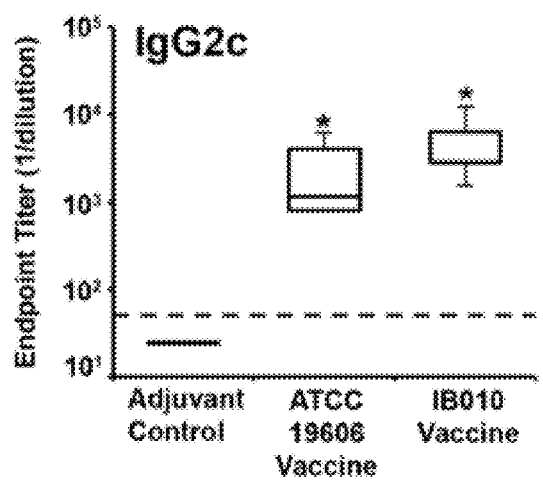

Levels of the IgG subtypes IgG1 and IgG2c, the IgG2a homolog in C57BL/6 (Martin et al., 1998. *J. Immunol. Methods* 212: 187-192), were determined in 21-day serum (FIGS. 2C and D). Both groups of mice receiving the inactivated vaccines had significant levels of IgG1 and IgG2c compared to control mice (p<0.001; Mann-Whitney U test). Interestingly, IgG1 titers were significantly higher in IB010-vaccinated mice compared to ATCC 19606-vaccinated mice (p=0.003; Mann-Whitney U test), whereas IgG2c titers were similar between these groups. These results indicate that both Th1 and Th2 responses are elicited by the inactivated IB010 vaccine similar to what was previously shown for the inactivated ATCC 19606 vaccine (McConnell y Pachón, 2010. Vaccine 29, 1-5).

Figure 3:
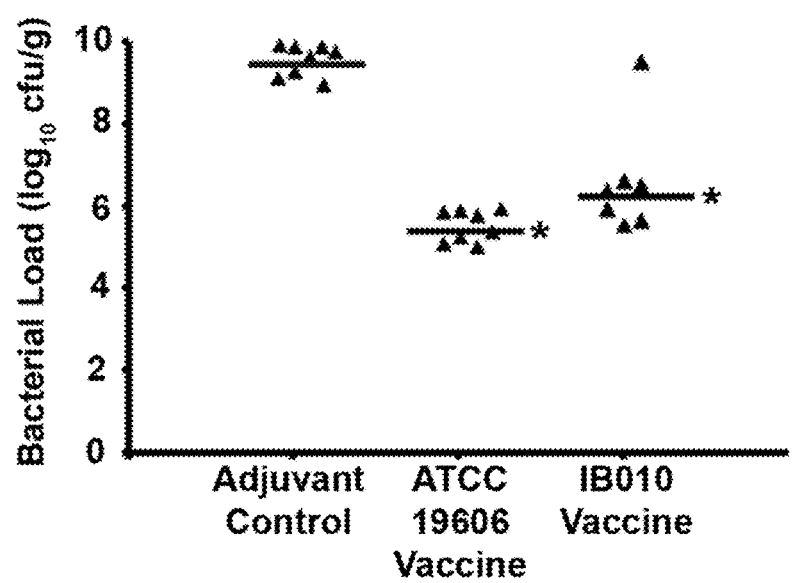

Effect of vaccination on post-infection bacterial loads. In order to characterize the effect of vaccination on post-infection tissue bacterial loads, we employed a mouse model previously developed by our group for the characterization of vaccine for preventing infection by *A. baumannii* (McConnell et al., 2011. *Infect. Immun.* 79, 518-526; McConnell et al., 2011. *Vaccine* 29: 5705-5710; McConnell y Pachón, 2010. *Vaccine* 29, 1-5). This model rapidly produces a disseminated infection in which bacteria are detected in distal organs as soon as one hour post-infection [16]. Vaccinated and control mice were infected with $2.0 \times 10^6$ cfu ($300 \times LD_{50}$) of the ATCC 19606 strain, and 12 hours after infection spleen bacterial loads were determined (FIG. 3). IB010 vaccination reduced the number of bacteria in spleens approximately 1000-fold compared to control mice (p<0.05; Mann-Whitney U test). Spleen bacterial loads in IB010 vaccinated mice were not significantly different than in mice immunized with inactivated ATCC 19606 cells.

Figure 4:
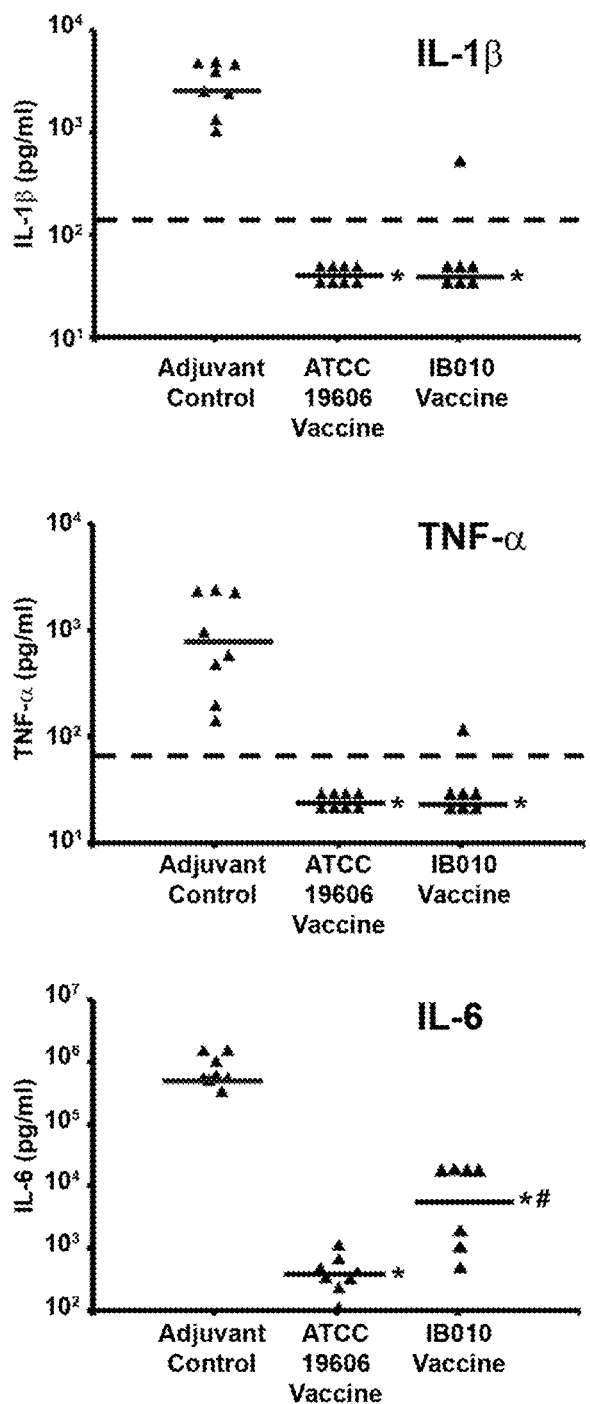

Effect of vaccination on post-infection serum cytokine levels and survival. In order to characterize the effect of immunization with the inactivated LPS deficient vaccine on cytokine levels, sera were collected from vaccinated and control mice 12 h post-infection and the levels of IL-1β, IL-6 and TNF-α were determined (FIG. 4). Levels of all three cytokines were significantly lower in both groups of vaccinated mice than in control mice (p=0.003 for IL-1β, IL-6 and TNF-α; Mann-Whitney U test), suggesting that vaccinated mice did not experience the pro-inflammatory cytokine release associated with the development of septic shock.

Figure 5A:
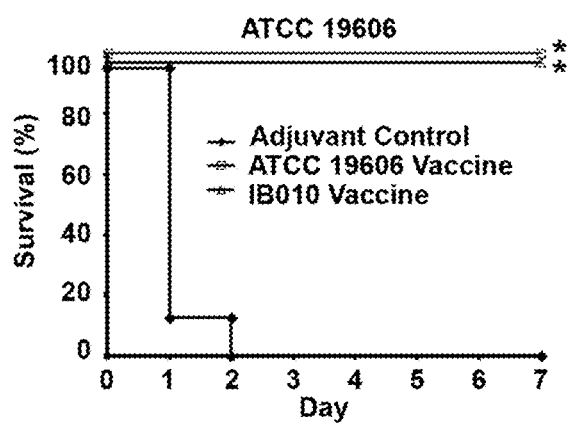
Figure 5B:
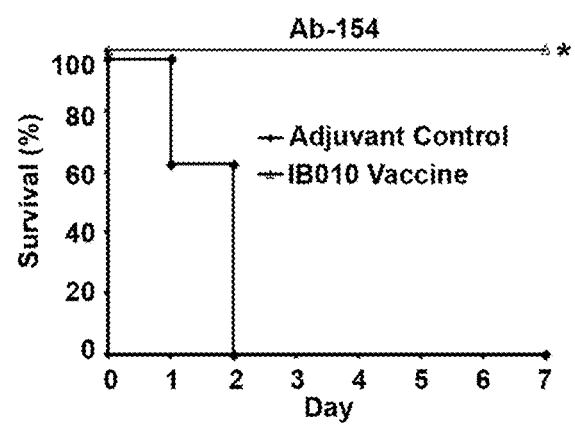
Figure 6:
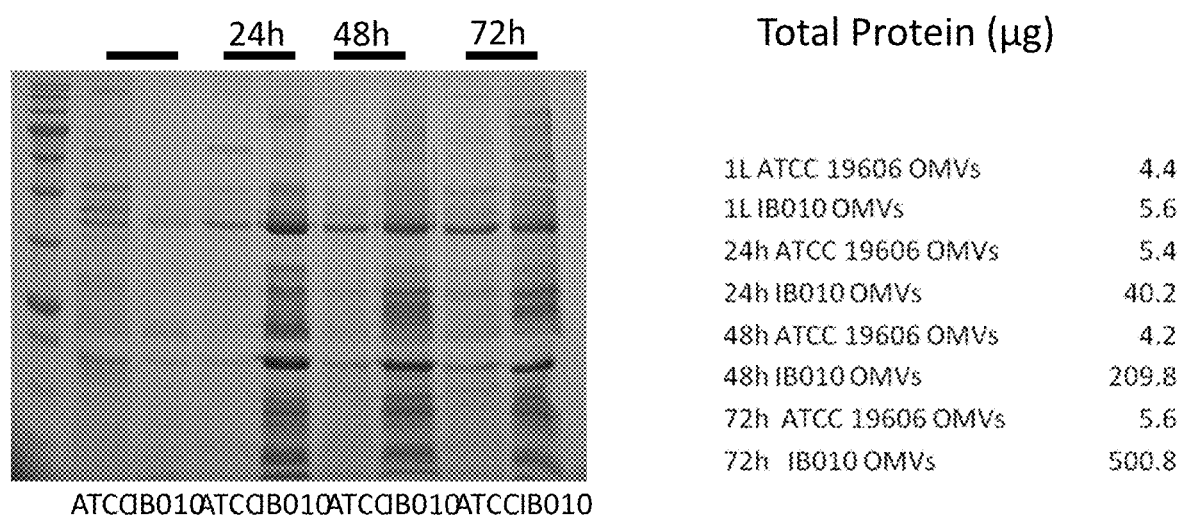

Vaccine efficacy was tested by infecting immunized and control mice with $2.25 \times 10^6$ cfu ($340.9 \times LD_{50}$) of the ATCC 19606 strain seven days after the second immunization, and survival was monitored over seven days (FIG. 5). All mice vaccinated with the IB010 vaccine were protected from challenge, whereas all control mice died within 48 hours (P<0.001; log-rank test). As expected, all mice immunized with the ATCC 19606 strain survived challenge, similar to results that were previously reported (McConnell et al., 2011. *Infect. Immun.* 79, 518-526; McConnell et al., 2011. *Vaccine* 29: 5705-5710; McConnell y Pachón, 2010. *Vaccine* 29, 1-5). In order to determine if vaccination with IB010 could protect against heterologous challenge with an unrelated strain, immunized and control mice were infected with $1.05 \times 10^6$ cfu ($2.18 \times LD_{50}$) of the previously characterized *A. baumannii* clinical isolate Ab-154 [29]. Once again, all immunized mice survived challenge whereas control mice succumbed to infection within 48 hours (p<0.001; log-rank test), indicating that immunization with IB010 can provide cross protection against challenge with a heterologous strain.

In conclusion, these results provide important information regarding the development of a vaccine for the prevention of infections caused by *A. baumannii* based on whole bacterial cells lacking LPS. These results may also provide insights into the possibility of developing vaccines for other bacterial species based on strains lacking LPS.

Example 2

This example relates to the development of a vaccine against *A. baumannii* based on OMVS purified from said cultures of mutants without LPS.

To carry out this objective, the strains ATCC 19606T and its mutant without LPS IB010, which was generated in our laboratory from the ATCC 19606T strain and contains a deletion of 462 nucleotides between positions 103 and 565 of the gene IpxD.

Upon realizing the purification of the OMVs of said strains the following protocol was used:
  Strains are refreshed on blood agar or MHBII plates with colistin at 10 mcg/ml and grown overnight at 37° C.
  A liquid culture is used to growth ATCC 19606 or IB010. They are cultured with aeration at 180 rpm at 37° C. overnight.
  The next day cultures of 50 or 100 ml or 1 L in MHB are made and incubated overnight at 37° C. with aeration (180 rpm)
  After incubation, the cells are centrifuged at 4000 rpm during 30 min at 4° C.
  Next, the supernatant is filtered with a 0.22 micron filter.
  Afterwards, the OMVs are precipitated by ultracentrifugation for 90 minutes at 30000 rpm at 4° C.
  Finally, the pellet is resuspended in PBS and the absence of viable bacteria is confirmed by plating. The OMVs are stored at −80° C.
  (Protocol adapted from McConnell M J et al. 2011 Aug. 5; 29(34):5705-10)

Using the previous protocol different purifications of OMVs have been performed.
  Purifications of OMVs of the strains ATCC 19606 and IB010 for the production of OMVs after culturing 24, 48 and 72 hours. After the purification of OMVs the amount of protein was quantified using Bradford method and 10 mcg of the protein was visualized in a 10% polyacrylamide gel with Coomassie stain.
  In addition, purification have been performed with OMVs from the strain ATCC 19606 and IB010 in the presence and absence of Bip, which is an iron chelator, with the objective of verifying if the presence of the chelator resulted in the increased expression of proteins related with iron metabolism, for example, siderophore receptors. In this case, OMVs were purified for the quantification of proteins and for Coomassie staining of acrylamide gels and for the visualization of OMVs by electron microscopy.
  Finally, OMVs were purified form the LPS mutant of a clinical isolate of *A. baumannii* Ab-167 which contains an ISAba1 insertion in the IpxC gene. Proteins were quantified and visualized on acrylamide gels by Coomassie staining. And proteins were quantified by Bradford and 2D Quant kit.

Example 3

Purification of Outer Membrane Proteins

*A. baumannii* ATCC 19606 was grown in 1 liter of Mueller-Hinton broth to an optical density at 600 nm (OD600) of 0.6, and pelleted bacteria were resuspended in 10 ml of 10 mM phosphate buffer, pH 7.2, and lysed by sonication. Unlysed cells were removed by centrifugation at 4,000×g for 5 min, and the supernatant was centrifuged at 20,000 g for 1 h to pellet cell envelopes. Inner membranes were selectively solubilized with 5 ml of 2% N-laurylsarcosinate by incubation at 37° C. for 30 min. The insoluble fraction was pelleted by centrifugation at 20,000 g for 1 h and then washed with 2 ml of 62.5 mM Tris-Cl, pH 6.8.

Endotoxin was extracted from the preparation by use of a cold detergent wash step in which proteins were resuspended in 5% SDS and incubated at 4° C. for 10 min. SDS and endotoxin were subsequently removed by precipitating in methanol chloroform and resuspended in PBS.

Addition of the Adjuvant

The purified proteins at a concentration of 500 mcg/ml were mixed with aluminum phosphate adjuvant at a 1:1 ration.

Clauses

1. An *Acinetobacter* cell deficient in LPS.
2. The *Acinetobacter* cell according to the preceding claim, obtained through partial or complete inactivation of one or various of the nucleic acids encoding the endogenous LPS biosynthesis genes.
3. The *Acinetobacter* cell according to the preceding claim, wherein the genes are selected from IpxA, IpxB and/or IpxC, or any combination thereof.
4. The *Acinetobacter* cell according to any one of the preceding claims, wherein the cell is obtained by deletions, and/or insertions of one or various nucleotides in the coding sequences of the genes.
5. The *Acinetobacter* cell according to any one of the preceding claims, wherein the cell is an attenuated *Acinetobacter* cell.
6. A composition comprising:
   a) a cell according to any one of claims 1-2, and
   b) a nucleic acid molecule, and/or a polypeptide.
7. The composition according to the preceding claim, wherein the nucleic acid molecule is recombinant and the polypeptide is recombinant.
8. The composition according to any one of claims 6-7, wherein the polypeptide is selected from:
   a) the peptide sequence SEQ ID NO: 27 (putative ferric siderophore receptor (*A. baumannii* ATCC 17978; accession number YP_001084684)) or a fragment thereof, wherein the fragments are biologically active fragments, and preferably selected from the list consisting of SEQ ID NO: 1 to SEQ ID NO: 11, or any of its combinations, or sequences having at least 85% sequence identity with peptide sequences SEQ ID NO: 1 to SEQ ID NO: 11, and/or
   b) the peptide sequence SEQ ID NO: 28 (putative ferric hydroximate siderophore receptor (*A. baumannii* ATCC 17978; accesión number YP_001084696)) or a fragment thereof, where the fragments are biologically active fragments, and preferably selected from the list consisting of SEQ ID NO: 12 to SEQ ID NO: 23, or any of its combinations, or sequences having at least 85% sequence identity with peptide sequences SEQ ID NO: 12 to SEC ID NO: 23.

9. The composition according to any one of claims 6-8, further comprising the amino acid sequence SEQ ID NO: 28 and the amino acid sequence SEQ ID NO: 27.

10. The composition according to any one of claims 6-9 further comprising a fusion protein comprising at least 2, preferably 3, more preferably 4 amino acid sequences form the list SEQ ID NO: 1 to SEQ ID NO: 23 or a variant of these sequences having at least 85% sequence identity with SEQ ID NO. 1 to SEQ ID NO: 23.

11. The composition according to claim 10, wherein the fusion protein further comprises the amino acid sequence SEQ ID NO: 24 or the amino acid sequence SEQ ID NO: 25.

12. The composition according to any one of claims 6-11, wherein the composition comprises a nucleotide sequence capable of transcribing an amino acid sequence as described in any one of claims 8-11.

13. The composition according to claim 12, wherein the nucleotide sequence is the SEQ ID NO: 26.

14. The composition according to any one of claims 6-13, further comprising an expression vector comprising the nucleotide sequence according to any one of claims 12-13.

15. The composition according to any one of claims 6-14, further comprising outer membrane vesicles deficient in LPS, or cells according to any one of claims 1 to 5.

16. The composition according to any one of claims 6-14, further comprising at least one of the purified outer membrane proteins of *A. baumannii* with amino acid sequence SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, or combinations thereof.

17. An outer membrane vesicle that is deficient in LPS.

18. The outer membrane vesicle according to claim 17, obtained from a cell according to any one of claims 1-5.

19. The composition according to any one of claims 6-15, wherein the cells or the outer membrane vesicles are designed to produce the amino acid sequences according to any one of claim 8-11 or 16 and/or comprising the nucleotides or nucleic acids according to any one of claims 12-13.

20. A nucleotide sequence capable of transcribing any fusion protein according to any one of claims 10-11.

21. An expression vector comprising a nucleotide or a nucleic acid according to any one of claims 12-13.

22. The composition according to any one of claims 7 to 16 and 19 that is a pharmaceutical composition.

23. The composition according to claim 22, further comprising a pharmaceutically acceptable vehicle.

24. The composition according to any one of claim 22 or 23, further comprising another active ingredient.

25. The composition according to any one of claims 22-24, further comprising an adjuvant.

26. The composition according to any one of claims 7 to 16, 19 to 22 and 25, wherein the composition is a vaccine.

27. The composition according to any one of claims 7 to 16, 19 to 22, and 25 for use as a medicament.

28. The composition according to any one of claims 7 to 16, 19 to 22, and 25 for the prevention, improvement or the treatment of an infection caused by *A. baumannii* in un mammal.

29. The composition according to any one of claims 7 to 16, 19 to 22, and 25 for conferring protection against infection caused by *A. baumannii* in a mammal.

30. An antibody or active fragment thereof obtained by immunization of a mammal with the composition according to any one of claims 7 to 16, 19 to 22 and 25.

31. The antibody or fragment thereof of the previous claim, wherein the composition is a pharmaceutical composition and wherein said composition is used in therapy, particularly for the treatment and prevention of infection caused by *A. baumannii*.

Additional Clauses

1. An *Acinetobacter* cell deficient in LPS obtained by partial or complete inactivation of one or various cellular nucleic acid molecules that encode endogenous LPS biosynthesis genes.

2. The *Acinetobacter* cell according to the preceding claim, wherein the genes are selected from IpxA, IpxB and/or IpxC, or any of their combinations.

3. A composition comprising:
   a) a cell according to any one of claims 1-2, and
   b) a recombinant nucleic acid molecule, and/or a recombinant polypeptide.

4. The composition according to claim 3, wherein the polypeptide is selected from:
   c) the peptide sequence SEQ ID NO: 27 (putative ferric siderophore receptor (*A. baumannii* ATCC 17978; accession number YP_001084684)) or a fragment thereof, wherein the fragments are biologically active fragments, and preferably selected from the list consisting of SEQ ID NO: 1 to SEQ ID NO: 11, or any of its combinations, or sequences having at least 85% sequence identity with peptide sequences SEQ ID NO: 1 to SEQ ID NO: 11, and/or
   d) the peptide sequence SEQ ID NO: 28 (putative ferric hydroximate siderophore receptor (*A. baumannii* ATCC 17978; accesión number YP_001084696)) or a fragment thereof, where the fragments are biologically active fragments, and preferably selected from the list consisting of SEQ ID NO: 12 to SEQ ID NO: 23, or any of its combinations, or sequences having at least 85% sequence identity with peptide sequences SEQ ID NO: 12 to SEC ID NO: 23.

5. The composition according to any one of claims 3-4, wherein the composition comprises a nucleotide sequence capable of transcribing an amino acid sequence described in claim 4, preferably SEQ ID NO: 26.

6. The composition according to any one of claims 3-5, further comprising an outer membrane vesicle deficient in LPS, or cells according to any one of claims 1 and 2.

7. The composition according to any one of claims 3-6, further comprising at least one of the proteins purified from the outer membrane of *A. baumannii* SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, or any combination thereof.

8. An outer membrane vesicle deficient in LPS.

9. The outer membrane vesicle according to claim 8, obtained from a cell as described in any one of claims 1-2.

10. The composition according to any one of claims 3-7, wherein the cells or the outer membrane vesicles are designed to produce the polypeptide sequences according to any one of claims 4 and 7, and/or comprising the nucleic acid sequences of claim 5.

11. The composition according to any one of claims 3-7 and 10, wherein the composition is a pharmaceutical composition.

12. The composition according to any one of claims 3-7, 10 and 11 for use as a medicament.

13. The composition according to any one of claims 3-7, 10 and 11 for use in the prevention, improvement or treatment of an infection caused by *A. baumannii* in a mammal.

14. An antibody or active fragment thereof obtained by immunization of a mammal with the composition according to any one of claims 3 to 7, 10 and 11.

15. The antibody or the active fragment thereof according to the preceding claim, wherein the composition is a pharmaceutical composition, and where said composition is used in therapy, particularly for the treatment or prevention of an infection caused by *A. baumannii*.

The invention claimed is:

1. A method for the prophylactic treatment of an infection caused by *Acinetobacter baumannii* in a mammal, wherein the method comprises administering to said mammal an *Acinetobacter baumannii* strain deficient in lipopolysaccharide (LPS) characterized by the partial or complete inactivation of the genes selected from the group consisting of LpxA, LpxC and LpxD.

2. The method according to claim 1, wherein the *Acinetobacter baumannii* strain deficient in LPS is an ATCC 19606 strain with a mutation in one or more genes selected from the group consisting of LpxA, LpxC and LpxD.

* * * * *

SEQUENCE LISTING

```
<160> NUMBER OF SEQ ID NOS: 101

<210> SEQ ID NO 1
<211> LENGTH: 12
<212> TYPE: PRT
<213> ORGANISM: Acinetobacter baumannii
<220> FEATURE:
<221> NAME/KEY: PEPTIDE
<222> LOCATION: (1)..(12)
<223> OTHER INFORMATION: anti-A. baumannii immunogen

<400> SEQUENCE: 1

Thr Ser Ser Asp Thr Phe Arg Ser Asp Gly Leu Ala
1               5                   10

<210> SEQ ID NO 2
<211> LENGTH: 28
<212> TYPE: PRT
<213> ORGANISM: Acinetobacter baumannii
<220> FEATURE:
<221> NAME/KEY: PEPTIDE
<222> LOCATION: (1)..(28)
<223> OTHER INFORMATION: Anti-A. Baumannii immunogen

<400> SEQUENCE: 2

Thr Ser Arg Gly Ser Gln Phe Asp Gly Asn Gly Asp Arg Ile Ser Leu
1               5                   10                  15

Ser Pro Trp Gln Gly Ser Thr Met Asp Thr Asp Thr
            20                  25

<210> SEQ ID NO 3
<211> LENGTH: 41
<212> TYPE: PRT
<213> ORGANISM: Acinetobacter baumannii
<220> FEATURE:
<221> NAME/KEY: PEPTIDE
<222> LOCATION: (1)..(41)
<223> OTHER INFORMATION: Anti-A. Baumannii immunogen

<400> SEQUENCE: 3

Tyr Lys Lys Gln Asp Thr Asp Tyr Gly Pro Asp Tyr Ser Tyr Leu Pro
1               5                   10                  15

Thr Thr Ser Lys Ser Asn Asp Ala Thr Thr Pro Thr Tyr Lys Ala Ile
            20                  25                  30

Lys Gly Leu Lys Leu Ser Asn Pro Leu
            35                  40
```

-continued

<210> SEQ ID NO 4
<211> LENGTH: 29
<212> TYPE: PRT
<213> ORGANISM: Acinetobacter baumannii
<220> FEATURE:
<221> NAME/KEY: PEPTIDE
<222> LOCATION: (1)..(29)
<223> OTHER INFORMATION: Anti-A. Baumannii immunogen

<400> SEQUENCE: 4

```
Arg Asn Glu Lys Ser Arg Phe Phe Pro Tyr Gly Leu Ser Asn Lys Ser
1               5                   10                  15

Val Thr Ser Val Asn Gln Ser Gln Ser Glu Ile Glu Val
            20                  25
```

<210> SEQ ID NO 5
<211> LENGTH: 36
<212> TYPE: PRT
<213> ORGANISM: Acinetobacter baumannii
<220> FEATURE:
<221> NAME/KEY: PEPTIDE
<222> LOCATION: (1)..(36)
<223> OTHER INFORMATION: Anti-A. Baumannii immunogen

<400> SEQUENCE: 5

```
Glu Lys Asp Lys Gln Phe Val Asp Ile Leu Ala Thr Gln Tyr Pro Tyr
1               5                   10                  15

Leu Val Tyr Thr Pro Thr Gly Gln Arg Lys Gly Tyr Gly Pro Asn Thr
            20                  25                  30

Glu Ile Gln Asn
        35
```

<210> SEQ ID NO 6
<211> LENGTH: 28
<212> TYPE: PRT
<213> ORGANISM: Acinetobacter baumannii
<220> FEATURE:
<221> NAME/KEY: PEPTIDE
<222> LOCATION: (1)..(28)
<223> OTHER INFORMATION: Anti-A. Baumannii immunogen

<400> SEQUENCE: 6

```
Ile Gln Ala Asp Thr Asp Ala Tyr Ile Pro Ser Arg Glu Thr Thr Met
1               5                   10                  15

Val Pro Ala Gly Ser Thr His Asp Asp Lys Pro Leu
            20                  25
```

<210> SEQ ID NO 7
<211> LENGTH: 27
<212> TYPE: PRT
<213> ORGANISM: Acinetobacter baumannii
<220> FEATURE:
<221> NAME/KEY: PEPTIDE
<222> LOCATION: (1)..(27)
<223> OTHER INFORMATION: Anti-A. Baumannii immunogen

<400> SEQUENCE: 7

```
Pro Asp Val Gln Arg Met Leu Arg Asp Val Ser Thr Tyr Thr Val Ser
1               5                   10                  15

Thr Ala Asn Leu Gln Pro Ile Thr Val Asn Ser
            20                  25
```

<210> SEQ ID NO 8
<211> LENGTH: 23
<212> TYPE: PRT
<213> ORGANISM: Acinetobacter baumannii

```
<220> FEATURE:
<221> NAME/KEY: PEPTIDE
<222> LOCATION: (1)..(23)
<223> OTHER INFORMATION: Anti-A. Baumannii immunogen

<400> SEQUENCE: 8

Asn Thr Ser Asp Lys Thr Val Gln Phe Asn Asn Arg Ala Ala Lys Val
1               5                   10                  15

Val Asp Thr Asp Gln Arg Val
            20

<210> SEQ ID NO 9
<211> LENGTH: 22
<212> TYPE: PRT
<213> ORGANISM: Acinetobacter baumannii
<220> FEATURE:
<221> NAME/KEY: PEPTIDE
<222> LOCATION: (1)..(22)
<223> OTHER INFORMATION: Anti-A. Baumannii immunogen

<400> SEQUENCE: 9

Thr Arg Gly Gln Tyr Lys Asp Val Ala Asn Lys Trp His Glu Leu Asn
1               5                   10                  15

Ser Phe Thr Val Ala Pro
            20

<210> SEQ ID NO 10
<211> LENGTH: 36
<212> TYPE: PRT
<213> ORGANISM: Acinetobacter baumannii
<220> FEATURE:
<221> NAME/KEY: PEPTIDE
<222> LOCATION: (1)..(36)
<223> OTHER INFORMATION: Anti-A. Baumannii immunogen

<400> SEQUENCE: 10

Ile Lys Gly Thr Asn Lys Ala Tyr Lys Asp Asp Arg Glu Leu Ala Ala
1               5                   10                  15

Phe Ala Thr Thr Gln Asp Glu Ala Phe Gln Asn Ala Val Lys Asn Asp
            20                  25                  30

Ala Asn Ser Ala
        35

<210> SEQ ID NO 11
<211> LENGTH: 33
<212> TYPE: PRT
<213> ORGANISM: Acinetobacter baumannii
<220> FEATURE:
<221> NAME/KEY: PEPTIDE
<222> LOCATION: (1)..(33)
<223> OTHER INFORMATION: Anti-A. Baumannii immunogen

<400> SEQUENCE: 11

Tyr Asn Val Trp Asn Arg Gln Tyr Arg Thr Val Phe Ala Gln Gln Ala
1               5                   10                  15

Ala Val Ser Asn Ala Asn Pro Leu Leu Ala Ile Pro Ala Glu Gly Arg
            20                  25                  30

Thr

<210> SEQ ID NO 12
<211> LENGTH: 28
<212> TYPE: PRT
<213> ORGANISM: Acinetobacter baumannii
<220> FEATURE:
<221> NAME/KEY: PEPTIDE
```

```
<222> LOCATION: (1)..(28)
<223> OTHER INFORMATION: Anti-A. Baumannii immunogen

<400> SEQUENCE: 12

Val Lys Gly Ala Asp Ser Leu Thr Asn Ala Phe Gly Asp Pro Ser Ala
1               5                   10                  15

Thr Ile Asn Asn Ile Arg Lys Arg Pro Thr Gln Glu
            20                  25

<210> SEQ ID NO 13
<211> LENGTH: 28
<212> TYPE: PRT
<213> ORGANISM: Acinetobacter baumannii
<220> FEATURE:
<221> NAME/KEY: PEPTIDE
<222> LOCATION: (1)..(28)
<223> OTHER INFORMATION: Anti-A. Baumannii immunogen

<400> SEQUENCE: 13

Ser Gly Lys Val Arg Gly Arg Ile Met Gly Tyr Glu Gln Thr Gly Asp
1               5                   10                  15

Ser Tyr Leu Asp Arg Tyr Ser Ala Glu Lys Asn Gly
            20                  25

<210> SEQ ID NO 14
<211> LENGTH: 11
<212> TYPE: PRT
<213> ORGANISM: Acinetobacter baumannii
<220> FEATURE:
<221> NAME/KEY: PEPTIDE
<222> LOCATION: (1)..(11)
<223> OTHER INFORMATION: Anti-A. Baumannii immunogen

<400> SEQUENCE: 14

Ser Gln Glu Gln Asn Lys Pro Asn Ala Asn Asn
1               5                   10

<210> SEQ ID NO 15
<211> LENGTH: 15
<212> TYPE: PRT
<213> ORGANISM: Acinetobacter baumannii
<220> FEATURE:
<221> NAME/KEY: PEPTIDE
<222> LOCATION: (1)..(15)
<223> OTHER INFORMATION: Anti-A. Baumannii immunogen

<400> SEQUENCE: 15

Asn Pro Asn Pro Asp Trp Ala His Trp Asp Asn Glu Thr Gln Asn
1               5                   10                  15

<210> SEQ ID NO 16
<211> LENGTH: 36
<212> TYPE: PRT
<213> ORGANISM: Acinetobacter baumannii
<220> FEATURE:
<221> NAME/KEY: PEPTIDE
<222> LOCATION: (1)..(36)
<223> OTHER INFORMATION: Anti-A. Baumannii immunogen

<400> SEQUENCE: 16

Leu Asp Thr Lys His Asn Ser Arg Leu Leu Tyr Tyr Tyr Gly Tyr Pro
1               5                   10                  15

Lys Ala Asp Gly Ser Gly Val Ser Leu Thr Pro Trp Gly Gly Gln Glu
            20                  25                  30

His Gln Glu Lys
        35
```

```
<210> SEQ ID NO 17
<211> LENGTH: 50
<212> TYPE: PRT
<213> ORGANISM: Acinetobacter baumannii
<220> FEATURE:
<221> NAME/KEY: PEPTIDE
<222> LOCATION: (1)..(50)
<223> OTHER INFORMATION: Anti-A. Baumanii immunogen

<400> SEQUENCE: 17

Val Arg Asn His Gln Gln Asp Lys Gln Ser Thr Gly Thr Ile Asn Asp
1               5                   10                  15

Ser Asn Val Ile Lys Ser Thr Thr Asp Trp Ala Ser Trp Thr Pro
            20                  25                  30

Gln Ser Ile Thr Trp Ser Asp Phe Thr Glu Ala Ala Asn Tyr Lys Gln
        35                  40                  45

Asn Ile
    50

<210> SEQ ID NO 18
<211> LENGTH: 20
<212> TYPE: PRT
<213> ORGANISM: Acinetobacter baumannii
<220> FEATURE:
<221> NAME/KEY: PEPTIDE
<222> LOCATION: (1)..(20)
<223> OTHER INFORMATION: Anti-A. Baumanii immunogen

<400> SEQUENCE: 18

Val Gln Ala Glu Ser Lys Gly Glu Ser Tyr Ser Ser Pro Met Ser Tyr
1               5                   10                  15

Ser Glu Ser Lys
            20

<210> SEQ ID NO 19
<211> LENGTH: 21
<212> TYPE: PRT
<213> ORGANISM: Acinetobacter baumannii
<220> FEATURE:
<221> NAME/KEY: PEPTIDE
<222> LOCATION: (1)..(21)
<223> OTHER INFORMATION: Anti-A. Baumanii immunogen

<400> SEQUENCE: 19

Arg Pro Gln Thr Gly Ile Asp Lys Asp Thr Asn Gln Ala Leu Lys Pro
1               5                   10                  15

Ile Glu Gly Lys Ser
            20

<210> SEQ ID NO 20
<211> LENGTH: 29
<212> TYPE: PRT
<213> ORGANISM: Acinetobacter baumannii
<220> FEATURE:
<221> NAME/KEY: PEPTIDE
<222> LOCATION: (1)..(29)
<223> OTHER INFORMATION: Anti-A. Baumanii immunogen

<400> SEQUENCE: 20

Thr Glu Gln Asn Asn Tyr Pro Leu Arg Asn Ser Asp Gly Asn Pro Leu
1               5                   10                  15

Asn Arg Lys Val Pro Thr Ser Asp Leu Glu Ser Gln Gly
            20                  25
```

<210> SEQ ID NO 21
<211> LENGTH: 20
<212> TYPE: PRT
<213> ORGANISM: Acinetobacter baumannii
<220> FEATURE:
<221> NAME/KEY: PEPTIDE
<222> LOCATION: (1)..(20)
<223> OTHER INFORMATION: Anti-A. Baumannii immunogen

<400> SEQUENCE: 21

Ala Gln Phe Ser Ile Lys Asp Thr Lys Asn Gly Gly Glu Ala Arg Thr
1               5                   10                  15

Tyr Asn Pro Asn
            20

<210> SEQ ID NO 22
<211> LENGTH: 20
<212> TYPE: PRT
<213> ORGANISM: Acinetobacter baumannii
<220> FEATURE:
<221> NAME/KEY: PEPTIDE
<222> LOCATION: (1)..(20)
<223> OTHER INFORMATION: Anti-A. Baumannii immunogen

<400> SEQUENCE: 22

Gln Asp Gly Ile Lys Leu Tyr Asp Ser Asn Val Asn Gly Thr Ile Lys
1               5                   10                  15

Gln Asp Ala Tyr
            20

<210> SEQ ID NO 23
<211> LENGTH: 20
<212> TYPE: PRT
<213> ORGANISM: Acinetobacter baumannii
<220> FEATURE:
<221> NAME/KEY: PEPTIDE
<222> LOCATION: (1)..(20)
<223> OTHER INFORMATION: Anti-A. Baumannii immunogen

<400> SEQUENCE: 23

Asp Lys Lys Tyr Leu Asn Ser Phe Pro Asp Gly Gln Ala Phe Tyr Gly
1               5                   10                  15

Ala Pro Ala Asn
            20

<210> SEQ ID NO 24
<211> LENGTH: 586
<212> TYPE: PRT
<213> ORGANISM: Artificial Sequence
<220> FEATURE:
<223> OTHER INFORMATION: Fusion protein
<220> FEATURE:
<221> NAME/KEY: PEPTIDE
<222> LOCATION: (1)..(586)
<223> OTHER INFORMATION: Fusion protein

<400> SEQUENCE: 24

Val Lys Gly Ala Asp Ser Leu Thr Asn Ala Phe Gly Asp Pro Ser Ala
1               5                   10                  15

Thr Ile Asn Asn Ile Arg Lys Arg Pro Thr Gln Glu Ser Gln Glu Gln
            20                  25                  30

Asn Lys Pro Asn Ala Asn Asn Pro Asn Pro Asp Trp Ala His Trp
        35                  40                  45

Asp Asn Glu Thr Gln Asn Leu Asp Thr Lys His Asn Ser Arg Leu Leu
    50                  55                  60

```
Tyr Tyr Tyr Gly Tyr Pro Lys Ala Asp Gly Ser Gly Val Ser Leu Thr
 65                  70                  75                  80

Pro Trp Gly Gly Gln Glu His Gln Glu Lys Val Arg Asn His Gln Gln
                 85                  90                  95

Asp Lys Gln Ser Thr Gly Thr Ile Asn Asp Ser Asn Val Ile Lys Ser
            100                 105                 110

Thr Thr Thr Asp Trp Ala Ser Trp Thr Pro Gln Ser Ile Thr Trp Ser
            115                 120                 125

Asp Phe Thr Glu Ala Ala Asn Tyr Lys Gln Asn Ile Val Gln Ala Glu
            130                 135                 140

Ser Lys Gly Glu Ser Tyr Ser Ser Pro Met Ser Tyr Ser Glu Ser Lys
145                 150                 155                 160

Arg Pro Gln Thr Gly Ile Asp Lys Asp Thr Asn Gln Ala Leu Lys Pro
                165                 170                 175

Ile Glu Gly Lys Ser Thr Glu Gln Asn Asn Tyr Pro Leu Arg Asn Ser
            180                 185                 190

Asp Gly Asn Pro Leu Asn Arg Lys Val Pro Thr Ser Asp Leu Glu Ser
            195                 200                 205

Gln Gly Ala Gln Phe Ser Ile Lys Asp Thr Lys Asn Gly Gly Glu Ala
210                 215                 220

Arg Thr Tyr Asn Pro Asn Gln Asp Gly Ile Lys Leu Tyr Asp Ser Asn
225                 230                 235                 240

Val Asn Gly Thr Ile Lys Gln Asp Ala Tyr Asp Lys Lys Tyr Leu Asn
                245                 250                 255

Ser Phe Pro Asp Gly Gln Ala Phe Tyr Gly Ala Pro Ala Asn Thr Ser
            260                 265                 270

Ser Asp Thr Phe Arg Ser Asp Gly Leu Ala Thr Ser Arg Gly Ser Gln
            275                 280                 285

Phe Asp Gly Asn Gly Asp Arg Ile Ser Leu Ser Pro Trp Gln Gly Ser
            290                 295                 300

Thr Met Asp Thr Asp Thr Tyr Lys Asp Lys Gln Asp Thr Asp Tyr Gly
305                 310                 315                 320

Pro Asp Tyr Ser Tyr Leu Pro Thr Thr Ser Lys Ser Asn Asp Ala Thr
                325                 330                 335

Thr Pro Thr Tyr Lys Ala Ile Lys Gly Leu Lys Leu Ser Asn Pro Leu
            340                 345                 350

Arg Asn Glu Lys Ser Arg Phe Phe Pro Tyr Gly Leu Ser Asn Lys Ser
            355                 360                 365

Val Thr Ser Val Asn Gln Ser Gln Ser Glu Ile Glu Val Glu Lys Asp
            370                 375                 380

Lys Gln Phe Val Asp Ile Leu Ala Thr Gln Tyr Pro Tyr Leu Val Tyr
385                 390                 395                 400

Thr Pro Thr Gly Gln Arg Lys Gly Tyr Gly Pro Asn Thr Glu Ile Gln
                405                 410                 415

Asn Ile Gln Ala Asp Thr Asp Ala Tyr Ile Pro Ser Arg Glu Thr Thr
            420                 425                 430

Met Val Pro Ala Gly Ser Thr His Asp Asp Lys Pro Leu Pro Asp Val
            435                 440                 445

Gln Arg Met Leu Arg Asp Val Ser Thr Tyr Thr Val Ser Thr Ala Asn
            450                 455                 460

Leu Gln Pro Ile Thr Val Asn Ser Asn Thr Ser Asp Lys Thr Val Gln
465                 470                 475                 480
```

```
Phe Asn Asn Arg Ala Ala Lys Val Val Asp Thr Asp Gln Arg Val Thr
            485                 490                 495
Arg Gly Gln Tyr Lys Asp Val Ala Asn Lys Trp His Glu Leu Asn Ser
        500                 505                 510
Phe Thr Val Ala Pro Ile Lys Gly Thr Asn Lys Ala Tyr Lys Asp Asp
        515                 520                 525
Arg Glu Leu Ala Ala Phe Ala Thr Thr Gln Asp Glu Ala Phe Gln Asn
    530                 535                 540
Ala Val Lys Asn Asp Ala Asn Ser Ala Tyr Asn Val Trp Asn Arg Gln
545                 550                 555                 560
Tyr Arg Thr Val Phe Ala Gln Gln Ala Val Ser Asn Ala Asn Pro
                565                 570                 575
Leu Leu Ala Ile Pro Ala Glu Gly Arg Thr
            580                 585

<210> SEQ ID NO 25
<211> LENGTH: 615
<212> TYPE: PRT
<213> ORGANISM: Artificial Sequence
<220> FEATURE:
<223> OTHER INFORMATION: Fusion protein
<220> FEATURE:
<221> NAME/KEY: PEPTIDE
<222> LOCATION: (1)..(615)
<223> OTHER INFORMATION: Fusion protein

<400> SEQUENCE: 25

Met Ser Gly Lys Val Arg Gly Arg Ile Met Gly Tyr Glu Gln Thr Gly
1               5                   10                  15
Asp Ser Tyr Leu Asp Arg Tyr Ser Ala Glu Lys Asn Gly Val Lys Gly
            20                  25                  30
Ala Asp Ser Leu Thr Asn Ala Phe Gly Asp Pro Ser Ala Thr Ile Asn
        35                  40                  45
Asn Ile Arg Lys Arg Pro Thr Gln Glu Ser Gln Glu Gln Asn Lys Pro
    50                  55                  60
Asn Ala Asn Asn Asn Pro Asn Pro Asp Trp Ala His Trp Asp Asn Glu
65                  70                  75                  80
Thr Gln Asn Leu Asp Thr Lys His Asn Ser Arg Leu Leu Tyr Tyr Tyr
                85                  90                  95
Gly Tyr Pro Lys Ala Asp Gly Ser Gly Val Ser Leu Thr Pro Trp Gly
            100                 105                 110
Gly Gln Glu His Gln Glu Lys Val Arg Asn His Gln Gln Asp Lys Gln
        115                 120                 125
Ser Thr Gly Thr Ile Asn Asp Ser Asn Val Ile Lys Ser Thr Thr Thr
    130                 135                 140
Asp Trp Ala Ser Trp Thr Pro Gln Ser Ile Thr Trp Ser Asp Phe Thr
145                 150                 155                 160
Glu Ala Ala Asn Tyr Lys Gln Asn Ile Val Gln Ala Glu Ser Lys Gly
                165                 170                 175
Glu Ser Tyr Ser Ser Pro Met Ser Tyr Ser Glu Ser Lys Arg Pro Gln
            180                 185                 190
Thr Gly Ile Asp Lys Asp Thr Asn Gln Ala Leu Lys Pro Ile Glu Gly
        195                 200                 205
Lys Ser Thr Glu Gln Asn Asn Tyr Pro Leu Arg Asn Ser Asp Gly Asn
    210                 215                 220
Pro Leu Asn Arg Lys Val Pro Thr Ser Asp Leu Glu Ser Gln Gly Ala
225                 230                 235                 240
```

```
Gln Phe Ser Ile Lys Asp Thr Lys Asn Gly Gly Glu Ala Arg Thr Tyr
                245                 250                 255

Asn Pro Asn Gln Asp Gly Ile Lys Leu Tyr Asp Ser Asn Val Asn Gly
            260                 265                 270

Thr Ile Lys Gln Asp Ala Tyr Asp Lys Lys Tyr Leu Asn Ser Phe Pro
        275                 280                 285

Asp Gly Gln Ala Phe Tyr Gly Ala Pro Ala Asn Thr Ser Ser Asp Thr
    290                 295                 300

Phe Arg Ser Asp Gly Leu Ala Thr Ser Arg Gly Ser Gln Phe Asp Gly
305                 310                 315                 320

Asn Gly Asp Arg Ile Ser Leu Ser Pro Trp Gln Gly Ser Thr Met Asp
                325                 330                 335

Thr Asp Thr Tyr Lys Asp Lys Gln Asp Thr Tyr Gly Pro Asp Tyr
            340                 345                 350

Ser Tyr Leu Pro Thr Thr Ser Lys Ser Asn Asp Ala Thr Thr Pro Thr
        355                 360                 365

Tyr Lys Ala Ile Lys Gly Leu Lys Leu Ser Asn Pro Leu Arg Asn Glu
    370                 375                 380

Lys Ser Arg Phe Phe Pro Tyr Gly Leu Ser Asn Lys Ser Val Thr Ser
385                 390                 395                 400

Val Asn Gln Ser Gln Ser Glu Ile Glu Val Glu Lys Asp Lys Gln Phe
                405                 410                 415

Val Asp Ile Leu Ala Thr Gln Tyr Pro Tyr Leu Val Tyr Thr Pro Thr
            420                 425                 430

Gly Gln Arg Lys Gly Tyr Gly Pro Asn Thr Glu Ile Gln Asn Ile Gln
        435                 440                 445

Ala Asp Thr Asp Ala Tyr Ile Pro Ser Arg Glu Thr Thr Met Val Pro
    450                 455                 460

Ala Gly Ser Thr His Asp Asp Lys Pro Leu Pro Asp Val Gln Arg Met
465                 470                 475                 480

Leu Arg Asp Val Ser Thr Tyr Thr Val Ser Thr Ala Asn Leu Gln Pro
                485                 490                 495

Ile Thr Val Asn Ser Asn Thr Ser Asp Lys Thr Val Gln Phe Asn Asn
            500                 505                 510

Arg Ala Ala Lys Val Val Asp Thr Asp Gln Arg Val Thr Arg Gly Gln
        515                 520                 525

Tyr Lys Asp Val Ala Asn Lys Trp His Glu Leu Asn Ser Phe Thr Val
    530                 535                 540

Ala Pro Ile Lys Gly Thr Asn Lys Ala Tyr Lys Asp Asp Arg Glu Leu
545                 550                 555                 560

Ala Ala Phe Ala Thr Thr Gln Asp Glu Ala Phe Gln Asn Ala Val Lys
                565                 570                 575

Asn Asp Ala Asn Ser Ala Tyr Asn Val Trp Asn Arg Gln Tyr Arg Thr
            580                 585                 590

Val Phe Ala Gln Gln Ala Ala Val Ser Asn Ala Asn Pro Leu Leu Ala
        595                 600                 605

Ile Pro Ala Glu Gly Arg Thr
    610                 615

<210> SEQ ID NO 26
<211> LENGTH: 1650
<212> TYPE: DNA
<213> ORGANISM: Artificial Sequence
<220> FEATURE:
```

<223> OTHER INFORMATION: Polynucleotide coding for the fusion protein
<220> FEATURE:
<221> NAME/KEY: misc_feature
<222> LOCATION: (1)..(1650)
<223> OTHER INFORMATION: Polynucleotide coding for fusion protein

<400> SEQUENCE: 26

```
atgtctggta aagttcgtgg tcgtatcatg ggttacgaac agaccggtga ctcttacctg      60
gaccgttact ctgctgaaaa aaacggtgtt aaaggtgctg actctctgac caacgctttc     120
ggtgacccgt ctgctaccat caacaacatc cgtaaacgtc cgacccagga atctcaggaa     180
cagaacaaac cgaacgctaa caacaacccg aacccggact gggctcactg ggacaacgaa     240
acccagaacc tggacaccaa acacaactct cgtctgctgt actactacgg ttacccgaaa     300
gctgacggtt ctggtgtttc tctgaccccg tggggtggtc aggaacacca ggaaaaagtt     360
cgtaaccacc agcaggacaa acagtctacc ggtaccatca cgactctaa cgttatcaaa     420
tctaccacca ccgactgggc ttcttggacc ccgcagtcta tcacctggtc tgacttcacc     480
gaagctgcta actacaaaca gaacatcgtt caggctgaat ctaaaggtga atcttactct     540
tctccgatgt cttactctga atctaaacgt ccgcagaccg tatcgacaa agacaccaac     600
caggctctga aaccgatcga aggtaaatct accgaacaga caactaccc gctgcgtaac     660
tctgacggta acccgctgaa ccgtaaagtt ccgacctctg acctggaatc tcagggtgct     720
cagttctcta tcaaagacac caaaaacggt ggtgaagctc gtacctacaa cccgaaccag     780
gacggtatca aactgtacga ctctaacgtt aacggtacca tcaaacagga cgcttacgac     840
aaaaaatacc tgaactcttt cccggacggt caggctttct acggtgctcc ggctaacacc     900
tcttctgaca ccttccgttc tgacggtctg gctacctctc gtggttctca gttcgacggt     960
aacggtgacc gtatctctct gtctccgtgg caggttctca ccatggacac cgacacctac    1020
aaagacaaac aggacaccga ctacggtccg gactactctt acctgccgac cacctctaaa    1080
tctaacgacg ctaccaccc gacctacaaa gctatcaaag gtctgaaact gtctaacccg    1140
ctgcgtaacg aaaaatctcg tttcttcccg tacggtctgt ctaacaaatc tgttacctct    1200
gttaaccagt ctcagtctga aatcgaagtt gaaaaagaca acagttcgt tgacatcctg    1260
gctacccagt acccgtacct ggtttacacc ccgaccggtc agcgtaaagg ttacggtccg    1320
aacaccgaaa tccagaacat ccaggctgac accgacgctt acatcccgtc tcgtgaaacc    1380
accatggttc cggctggttc taccacgac gacaaaccgc tgccggacgt tcagcgtatg    1440
ctgcgtgacg tttctaccta caccgtttct accgctaacc tgcagccgat caccgttaac    1500
tctaacacct ctgacaaaac cgttcagttc aacaaccgtg ctgctaaagt tgttgacacc    1560
gaccagcgtg ttacccgtgg tcagtacaaa gacgttgcta caaatggca cgaactgaac    1620
tctttcaccg ttgctccgat caaaggtacc                                     1650
```

<210> SEQ ID NO 27
<211> LENGTH: 746
<212> TYPE: PRT
<213> ORGANISM: Acinetobacter baumannii
<220> FEATURE:
<221> NAME/KEY: PEPTIDE
<222> LOCATION: (1)..(746)
<223> OTHER INFORMATION: Amino acid sequence of putative ferric siderophore receptor protein

<400> SEQUENCE: 27

Met Thr Pro Cys Cys Leu Ala Ile Ser Ala Ile Phe Ala Gln Gln Ala
1               5                   10                  15

```
Tyr Ala Glu Thr Val Thr Gln Thr Ala Glu Val Ser Glu Asn Ala Thr
         20                  25                  30

Gln Lys Pro Val Ala Gln Leu Gln Lys Ile Val Val Thr Ala Thr Arg
         35                  40                  45

Thr Pro Lys Asn Ile Ala Glu Ile Ala Gly Thr Val Gln Ser Ile Asp
         50                  55                  60

Gln Lys Gln Ile Ile Gln Ala Thr Ala Gly Arg Lys Val Ala Asp
65                   70                  75                  80

Ile Leu Ala Gln Leu Val Pro Ser Leu Ala Ser Ser Gly Thr Thr
                 85                  90                  95

Ser Asn Tyr Gly Gln Thr Met Arg Gly Arg Asn Val Leu Val Met Ile
            100                 105                 110

Asp Gly Val Ser Gln Thr Gly Ser Arg Asp Val Ser Arg Gln Leu Asn
            115                 120                 125

Ser Ile Ser Pro Gly Met Ile Glu Arg Ile Glu Val Ile Ser Gly Ala
            130                 135                 140

Thr Ser Ile Tyr Gly Ser Gly Ala Thr Gly Gly Ile Ile Asn Ile Ile
145                 150                 155                 160

Thr Lys Arg Ala Asp Thr Ser Lys Pro Leu Ser Phe Glu Thr Lys Val
                165                 170                 175

Gly Ile Thr Ser Ser Asp Thr Phe Arg Ser Asp Gly Leu Ala Tyr Glu
            180                 185                 190

Val Gly Gln Ser Val Ser Phe Asn Lys Gly Asn Ile Asp Gly Phe Leu
            195                 200                 205

Gly Ala Asn Phe Thr Ser Arg Gly Ser Gln Phe Asp Gly Asn Gly Asp
            210                 215                 220

Arg Ile Ser Leu Ser Pro Trp Gln Gly Ser Thr Met Asp Thr Asp Thr
225                 230                 235                 240

Ile Asp Val Asn Gly Arg Leu Asn Phe Asn Leu Asn Asp Thr Gln Thr
                245                 250                 255

Leu Ser Phe Gly Ala Gln Tyr Tyr Lys Asp Lys Gln Asp Thr Asp Tyr
            260                 265                 270

Gly Pro Asp Tyr Ser Tyr Leu Pro Thr Thr Ser Lys Ser Asn Asp Ala
            275                 280                 285

Thr Thr Pro Thr Tyr Lys Ala Ile Lys Gly Leu Lys Leu Ser Asn Pro
290                 295                 300

Leu Phe Thr Glu Arg Tyr Ala Val Asn Ser Gln Tyr Gln Asn Gln Asp
305                 310                 315                 320

Phe Leu Gly Gln Ile Leu Asn Val Glu Ala Tyr Tyr Arg Asn Glu Lys
                325                 330                 335

Ser Arg Phe Phe Pro Tyr Gly Leu Ser Asn Lys Ser Val Thr Ser Val
            340                 345                 350

Asn Gln Ser Gln Ser Glu Ile Glu Val Ala Gly Leu Arg Ser Thr Met
            355                 360                 365

Gln Thr Asp Leu Asn Ile Ala Asn Arg Asp Met Lys Ile Thr Tyr Gly
            370                 375                 380

Leu Asp Tyr Asp Trp Glu Lys Asp Lys Gln Phe Val Asp Ile Leu Ala
385                 390                 395                 400

Thr Gln Tyr Pro Tyr Leu Val Tyr Thr Pro Thr Gly Gln Arg Lys Gly
                405                 410                 415

Tyr Gly Pro Asn Thr Glu Ile Gln Asn Ile Gly Ala Phe Val Gln Ser
            420                 425                 430
```

```
Asp Tyr Ala Val Thr Asp Lys Leu Asn Leu Gln Ala Gly Ile Arg Tyr
            435                 440                 445

Gln Tyr Ile Gln Ala Asp Thr Asp Ala Tyr Ile Pro Ser Arg Glu Thr
        450                 455                 460

Thr Met Val Pro Ala Gly Ser Thr His Asp Asp Lys Pro Leu Phe Asn
465                 470                 475                 480

Leu Gly Ala Val Tyr Lys Leu Thr Asp Ala Gln Gln Val Tyr Ala Asn
                485                 490                 495

Phe Ser Gln Gly Phe Ser Phe Pro Asp Val Gln Arg Met Leu Arg Asp
            500                 505                 510

Val Ser Thr Tyr Thr Val Ser Thr Ala Asn Leu Gln Pro Ile Thr Val
        515                 520                 525

Asn Ser Tyr Glu Leu Gly Trp Arg Leu Asn Gln Asp Asp Gly Leu Asn
530                 535                 540

Leu Gly Leu Thr Gly Phe Tyr Asn Thr Ser Asp Lys Thr Val Gln Phe
545                 550                 555                 560

Asn Asn Arg Ala Ala Lys Val Val Asp Thr Asp Gln Arg Val Tyr Gly
                565                 570                 575

Ala Glu Ala Thr Ile Ser Tyr Pro Phe Met Glu Asn Tyr Lys Val Gly
            580                 585                 590

Gly Thr Leu Gly Tyr Thr Arg Gly Gln Tyr Lys Asp Val Ala Asn Lys
        595                 600                 605

Trp His Glu Leu Asn Ser Phe Thr Val Ala Pro Val Lys Gly Thr Leu
        610                 615                 620

Phe Ala Glu Trp Asp Asn Asn Glu Gly Tyr Gly Val Arg Val Gln Met
625                 630                 635                 640

Gln Ala Ile Lys Gly Thr Asn Lys Ala Tyr Lys Asp Asp Arg Glu Leu
                645                 650                 655

Ala Ala Phe Ala Thr Thr Gln Asp Glu Ala Phe Gln Asn Ala Val Lys
            660                 665                 670

Asn Asp Ala Asn Ser Ala Ala Gln Ile Lys Gly Tyr Thr Thr Met Asp
        675                 680                 685

Val Leu Ala His Phe Pro Ala Trp Lys Gly Arg Val Asp Phe Gly Val
690                 695                 700

Tyr Asn Val Trp Asn Arg Gln Tyr Arg Thr Val Phe Ala Gln Gln Ala
705                 710                 715                 720

Ala Val Ser Asn Ala Asn Pro Leu Leu Ala Ile Pro Ala Glu Gly Arg
                725                 730                 735

Thr Tyr Gly Leu Ser Tyr Thr Phe Asn Tyr
            740                 745

<210> SEQ ID NO 28
<211> LENGTH: 679
<212> TYPE: PRT
<213> ORGANISM: Acinetobacter baumannii
<220> FEATURE:
<221> NAME/KEY: PEPTIDE
<222> LOCATION: (1)..(679)
<223> OTHER INFORMATION: Amino acid sequence of putative ferric
    hydroxamate siderophore receptor

<400> SEQUENCE: 28

Met Gln Thr Ile Gln Val Lys Ala Ser Asp Ala Glu Gln Ser Ser Glu
1               5                   10                  15

Gln Thr Lys Ala Tyr Asn Val Lys Asn Ser Ser Ser Ala Thr Lys Leu
            20                  25                  30
```

-continued

```
Asn Ile Glu Ala Lys Glu Thr Pro Gln Thr Ile Asn Val Val Thr Arg
             35                  40                  45
Gln Gln Ile Glu Asp Phe Gly Leu Thr Ser Thr Arg Asp Val Leu Arg
 50                  55                  60
Asn Thr Pro Gly Val Thr Val Ser Asn Gln Glu Thr Glu Arg Thr Thr
 65                  70                  75                  80
Tyr Met Ala Arg Gly Phe Glu Ile Ser Asn Ile Leu Thr Asp Gly Val
                 85                  90                  95
Gly Phe Pro Leu Ser Gly Tyr Asn Tyr Asn Thr Asn Pro Asp Thr
                100                 105                 110
Tyr Phe Tyr Asp Arg Val Glu Val Lys Gly Ala Asp Ser Leu Thr
                115                 120                 125
Asn Ala Phe Gly Asp Pro Ser Ala Thr Ile Asn Asn Ile Arg Lys Arg
130                 135                 140
Pro Thr Gln Glu Phe Gln Ala Ser Asp Gly Val Ser Tyr Gly Ser Trp
145                 150                 155                 160
Asp Thr Gln Arg Tyr Glu Ala Asp Val Ser Gly Ser Ile Leu Pro Ser
                165                 170                 175
Gly Lys Val Arg Gly Arg Ile Met Gly Tyr Glu Gln Thr Gly Asp Ser
                180                 185                 190
Tyr Leu Asp Arg Tyr Ser Ala Glu Lys Asn Gly Phe Ala Gly Ile Val
                195                 200                 205
Glu Ala Asp Leu Thr Asp Ser Thr Leu Leu Thr Ala Gly Tyr Ser Gln
210                 215                 220
Glu Gln Asn Lys Pro Asn Ala Asn Asn Trp Gly Ala Leu Pro Leu Leu
225                 230                 235                 240
Asp Ala Asn Gly Lys Gln Ile Ser Tyr Asp Arg Ser Tyr Asn Pro Asn
                245                 250                 255
Pro Asp Trp Ala His Trp Asp Asn Glu Thr Gln Asn Ala Phe Val Glu
                260                 265                 270
Leu Lys Gln Lys Leu Asn Asp Gln Trp Asn Ala Lys Leu Thr Tyr Asn
                275                 280                 285
Tyr Leu Asp Thr Lys His Asn Ser Arg Leu Leu Tyr Tyr Gly Tyr
                290                 295                 300
Pro Lys Ala Asp Gly Ser Gly Val Ser Leu Thr Pro Trp Gly Gly Gln
305                 310                 315                 320
Glu His Gln Glu Lys His Ala Val Asp Phe Asn Leu Glu Gly Thr Tyr
                325                 330                 335
Lys Leu Phe Asn Arg Glu His Glu Ala Thr Leu Gly Tyr Ser Tyr Val
                340                 345                 350
Arg Asn His Gln Gln Asp Lys Gln Ser Thr Gly Thr Ile Asn Asp Ser
                355                 360                 365
Asn Val Ile Lys Ser Thr Thr Thr Asp Trp Ala Ser Trp Thr Pro Gln
370                 375                 380
Ser Ile Thr Trp Ser Ala Phe Thr Glu Ala Ala Asn Tyr Lys Gln Asn
385                 390                 395                 400
Ile Asn Ser Ile Tyr Ala Ala Thr Arg Leu His Leu Asn Glu Asp Leu
                405                 410                 415
Lys Leu Leu Leu Gly Val Asn Tyr Val Gln Ala Glu Ser Lys Gly Glu
                420                 425                 430
Ser Tyr Ser Ser Pro Met Ser Tyr Ser Glu Ser Lys Val Ser Pro Tyr
                435                 440                 445
Val Gly Leu Thr Tyr Asn Phe Thr Pro Glu Tyr Thr Gly Tyr Met Ser
```

```
            450                 455                 460
Tyr Thr Ser Ile Phe Arg Pro Gln Thr Gly Ile Asp Lys Asp Thr Asn
465                 470                 475                 480

Gln Ala Leu Lys Pro Ile Glu Gly Lys Ser Tyr Glu Met Gly Val Lys
                485                 490                 495

Ser Ser Trp Leu Asp Asp Arg Leu Thr Gly Thr Leu Ser Val Phe Lys
                500                 505                 510

Thr Glu Gln Asn Asn Tyr Pro Leu Arg Asn Ser Asp Gly Asn Pro Leu
                515                 520                 525

Asn Arg Lys Val Pro Thr Ser Asp Leu Glu Ser Gln Gly Val Glu Val
                530                 535                 540

Gly Leu Ser Gly Gln Ile Thr Asp Asn Val Asn Leu Ser Leu Gly Tyr
545                 550                 555                 560

Ala Gln Phe Ser Ile Lys Asp Thr Lys Asn Gly Gly Glu Ala Arg Ile
                565                 570                 575

Tyr Asn Pro Asn Gln Thr Leu Asn Leu Leu Thr Thr Tyr Thr Pro Pro
                580                 585                 590

Val Leu Pro Lys Leu Lys Val Gly Ala Gly Leu Gln Trp Gln Asp Gly
                595                 600                 605

Ile Lys Leu Tyr Asp Ser Asn Val Asn Gly Thr Ile Lys Gln Asp Ala
                610                 615                 620

Tyr Ala Leu Val Asn Leu Met Ala Ser Tyr Glu Val Asn Asp His Ile
625                 630                 635                 640

Thr Leu Gln Ala Asn Gly Asn Asn Ile Phe Asp Lys Lys Tyr Leu Asn
                645                 650                 655

Ser Phe Pro Asp Gly Gln Ala Phe Tyr Gly Ala Pro Ala Asn Tyr Thr
                660                 665                 670

Val Ala Val Lys Phe Lys Tyr
                675

<210> SEQ ID NO 29
<211> LENGTH: 829
<212> TYPE: PRT
<213> ORGANISM: Acinetobacter baumannii

<400> SEQUENCE: 29

Met Pro Leu Ala Leu Val Ser Ala Met Ala Val Gln Gln Ala Tyr
1               5                   10                  15

Ala Ala Asp Asp Phe Val Val Arg Asp Ile Arg Val Asn Gly Leu Val
                20                  25                  30

Arg Leu Thr Pro Ala Asn Val Tyr Thr Met Leu Pro Ile Asn Ser Gly
            35                  40                  45

Asp Arg Val Asn Glu Pro Met Ile Ala Glu Ala Ile Arg Thr Leu Tyr
        50                  55                  60

Ala Thr Gly Leu Phe Asp Asp Ile Lys Ala Ser Lys Glu Asn Asp Thr
65                  70                  75                  80

Leu Val Phe Asn Val Ile Glu Arg Pro Ile Ile Ser Lys Leu Glu Phe
                85                  90                  95

Lys Gly Asn Lys Leu Ile Pro Lys Glu Ala Leu Glu Gln Gly Leu Lys
                100                 105                 110

Lys Met Gly Ile Ala Glu Gly Glu Val Phe Lys Lys Ser Ala Leu Gln
            115                 120                 125

Thr Ile Glu Thr Glu Leu Glu Gln Gln Tyr Thr Gln Gln Gly Arg Tyr
        130                 135                 140
```

```
Asp Ala Asp Val Thr Val Asp Thr Val Ala Arg Pro Asn Asn Arg Val
145                 150                 155                 160

Glu Leu Lys Ile Asn Phe Asn Glu Gly Thr Pro Ala Lys Val Phe Asp
            165                 170                 175

Ile Asn Val Ile Gly Asn Thr Val Phe Lys Asp Ser Glu Ile Lys Gln
        180                 185                 190

Ala Phe Ala Val Lys Glu Ser Gly Trp Ala Ser Val Val Thr Arg Asn
    195                 200                 205

Asp Arg Tyr Ala Arg Glu Lys Met Ala Ala Ser Leu Glu Ala Leu Arg
210                 215                 220

Ala Met Tyr Leu Asn Lys Gly Tyr Ile Asn Phe Asn Ile Asn Asn Ser
225                 230                 235                 240

Gln Leu Asn Ile Ser Glu Asp Lys Lys His Ile Phe Ile Glu Val Ala
            245                 250                 255

Val Asp Glu Gly Ser Gln Phe Lys Phe Gly Gln Thr Lys Phe Leu Gly
        260                 265                 270

Asp Ala Leu Tyr Lys Pro Glu Glu Leu Gln Ala Leu Lys Ile Tyr Lys
    275                 280                 285

Asp Gly Asp Thr Tyr Ser Gln Glu Lys Val Asn Ala Val Lys Gln Leu
290                 295                 300

Leu Leu Arg Lys Tyr Gly Asn Ala Gly Tyr Tyr Phe Ala Asp Val Asn
305                 310                 315                 320

Ile Val Pro Gln Ile Asn Asn Glu Thr Gly Val Val Asp Leu Asn Tyr
            325                 330                 335

Tyr Val Asn Pro Gly Gln Gln Val Thr Val Arg Arg Ile Asn Phe Thr
        340                 345                 350

Gly Asn Ser Lys Thr Ser Asp Glu Val Leu Arg Arg Glu Met Arg Gln
    355                 360                 365

Met Glu Gly Ala Leu Ala Ser Asn Glu Lys Ile Asp Leu Ser Lys Val
370                 375                 380

Arg Leu Glu Arg Thr Gly Phe Phe Lys Thr Val Asp Ile Lys Pro Ala
385                 390                 395                 400

Arg Ile Pro Asn Ser Pro Asp Gln Val Asp Leu Asn Val Asn Val Glu
            405                 410                 415

Glu Gln His Ser Gly Thr Thr Leu Ala Val Gly Tyr Ser Gln Ser
        420                 425                 430

Gly Gly Ile Thr Phe Gln Ala Gly Leu Ser Gln Thr Asn Phe Met Gly
    435                 440                 445

Thr Gly Asn Arg Val Ala Ile Asp Leu Ser Arg Ser Glu Thr Gln Asp
450                 455                 460

Tyr Tyr Asn Leu Ser Val Thr Asp Pro Tyr Phe Thr Ile Asp Gly Val
465                 470                 475                 480

Ser Arg Gly Tyr Asn Val Tyr Arg Lys Thr Lys Leu Asn Asp Asp
            485                 490                 495

Tyr Asn Val Asn Asn Tyr Val Thr Asp Ser Phe Gly Gly Ser Leu Ser
        500                 505                 510

Phe Gly Tyr Pro Ile Asp Glu Asn Gln Ser Leu Ser Ala Ser Val Gly
    515                 520                 525

Val Asp Asn Thr Lys Val Thr Thr Gly Ala Phe Val Ser Thr Tyr Val
530                 535                 540

Arg Asp Tyr Leu Leu Ala Asn Gly Gly Lys Thr Thr Ser Thr Asn Thr
545                 550                 555                 560

Tyr Cys Leu Val Asp Leu Val Gln Asp Pro Gln Thr Gly Leu Tyr Lys
```

```
                565                 570                 575
Cys Pro Glu Gly Gln Thr Ser Gln Pro Tyr Gly Asn Ala Phe Glu Gly
            580                 585                 590

Glu Phe Phe Thr Tyr Asn Leu Asn Leu Gly Trp Ser Tyr Asn Thr Leu
        595                 600                 605

Asn Arg Pro Ile Phe Pro Thr Ser Gly Met Ser His Arg Val Gly Leu
    610                 615                 620

Glu Ile Gly Leu Pro Gly Ser Asp Val Asp Tyr Gln Lys Val Thr Tyr
625                 630                 635                 640

Asp Thr Gln Ala Phe Phe Pro Ile Gly Ser Thr Gly Phe Val Leu Arg
            645                 650                 655

Gly Tyr Gly Lys Leu Gly Tyr Gly Asn Asp Leu Pro Phe Tyr Lys Asn
            660                 665                 670

Phe Tyr Ala Gly Gly Tyr Gly Ser Val Arg Gly Tyr Asp Asn Ser Thr
            675                 680                 685

Leu Gly Pro Lys Tyr Ala Ser Val Asn Leu Gln Glu Glu Lys Lys Asn
        690                 695                 700

Asp Ser Ser Pro Glu Glu Val Gly Gly Asn Ala Leu Val Gln Phe Gly
705                 710                 715                 720

Thr Glu Leu Val Leu Pro Met Pro Phe Lys Gly Asp Trp Thr Arg Gln
                725                 730                 735

Val Arg Pro Val Leu Phe Ala Glu Gly Gly Gln Val Phe Asp Thr Lys
            740                 745                 750

Cys Asp Val Arg Ser Tyr Ser Met Ile Met Asn Gly Gln Gln Ile Ser
        755                 760                 765

Asp Ala Lys Lys Tyr Cys Glu Asp Asn Tyr Gly Phe Asp Leu Gly Asn
    770                 775                 780

Leu Arg Tyr Ser Val Gly Val Gly Val Thr Trp Ile Thr Met Ile Gly
785                 790                 795                 800

Pro Leu Ser Leu Ser Tyr Ala Phe Pro Leu Asn Asp Lys Pro Gly Asp
            805                 810                 815

Glu Thr Lys Glu Ile Gln Phe Glu Ile Gly Arg Thr Phe
            820                 825

<210> SEQ ID NO 30
<211> LENGTH: 458
<212> TYPE: PRT
<213> ORGANISM: Acinetobacter baumannii

<400> SEQUENCE: 30

Met Arg Gly Pro Glu Pro Val Val Lys Thr Asp Ile Pro Gln Ser Tyr
1               5                   10                  15

Ala Tyr Asn Ser Ala Ser Gly Thr Ser Ile Ala Glu Gln Gly Tyr Lys
            20                  25                  30

Gln Phe Phe Ala Asp Pro Arg Leu Leu Glu Val Ile Asp Leu Ala Leu
        35                  40                  45

Ala Asn Asn Arg Asp Leu Arg Thr Ala Thr Leu Asn Ile Glu Arg Ala
    50                  55                  60

Gln Gln Gln Tyr Gln Ile Thr Gln Asn Asn Gln Leu Pro Thr Ile Gly
65                  70                  75                  80

Ala Ser Gly Ser Ala Ile Arg Gln Val Ser Gln Ser Arg Asp Pro Asn
                85                  90                  95

Asn Pro Tyr Ser Thr Tyr Gln Val Gly Leu Gly Val Thr Ala Tyr Glu
            100                 105                 110
```

```
Leu Asp Phe Trp Gly Arg Val Arg Ser Leu Lys Asp Ala Leu Asp
            115                 120                 125

Ser Tyr Leu Ala Thr Gln Ser Ala Arg Asp Ser Thr Gln Ile Ser Leu
    130                 135                 140

Ile Ser Gln Val Ala Gln Ala Trp Leu Asn Tyr Ser Phe Ala Thr Ala
145                 150                 155                 160

Asn Leu Arg Leu Ala Glu Gln Thr Leu Lys Ala Gln Leu Asp Ser Tyr
                165                 170                 175

Asn Leu Asn Lys Lys Arg Phe Asp Val Gly Ile Asp Ser Glu Val Pro
            180                 185                 190

Leu Arg Gln Ala Gln Ile Ser Val Glu Thr Ala Arg Asn Asp Val Ala
        195                 200                 205

Asn Tyr Lys Thr Gln Ile Ala Gln Ala Gln Asn Leu Leu Asn Leu Leu
    210                 215                 220

Val Gly Gln Pro Val Pro Gln Asn Leu Leu Pro Thr Gln Pro Val Lys
225                 230                 235                 240

Arg Ile Ala Gln Gln Asn Val Phe Thr Ala Gly Leu Pro Ser Asp Leu
                245                 250                 255

Leu Asn Asn Arg Pro Asp Val Lys Ala Ala Glu Tyr Asn Leu Ser Ala
            260                 265                 270

Ala Gly Ala Asn Ile Gly Ala Ala Lys Ala Arg Leu Phe Pro Thr Ile
        275                 280                 285

Ser Leu Thr Gly Ser Ala Gly Tyr Ala Ser Thr Asp Leu Ser Asp Leu
    290                 295                 300

Phe Lys Ser Gly Gly Phe Val Trp Ser Val Gly Pro Ser Leu Asp Leu
305                 310                 315                 320

Pro Ile Phe Asp Trp Gly Thr Arg Arg Ala Asn Val Lys Ile Ser Glu
                325                 330                 335

Thr Asp Gln Lys Ile Ala Leu Ser Asp Tyr Glu Lys Ser Val Gln Ser
            340                 345                 350

Ala Phe Arg Glu Val Asn Asp Ala Leu Ala Thr Arg Ala Asn Ile Gly
        355                 360                 365

Glu Arg Leu Thr Ala Gln Gln Arg Leu Val Glu Ala Thr Asn Arg Asn
370                 375                 380

Tyr Thr Leu Ser Asn Ala Arg Phe Arg Ala Gly Ile Asp Ser Tyr Leu
385                 390                 395                 400

Thr Val Leu Asp Ala Gln Arg Ser Ser Tyr Ala Ala Glu Gln Gly Leu
                405                 410                 415

Leu Leu Leu Gln Gln Ala Asn Leu Asn Asn Gln Ile Glu Leu Tyr Lys
            420                 425                 430

Thr Leu Gly Gly Gly Leu Lys Ala Asn Thr Ser Asp Thr Val Val His
        435                 440                 445

Gln Pro Ser Ser Ala Glu Leu Lys Lys Gln
    450                 455

<210> SEQ ID NO 31
<211> LENGTH: 412
<212> TYPE: PRT
<213> ORGANISM: Acinetobacter baumannii

<400> SEQUENCE: 31

Met Met Ser Gly Ala Asn Ala Ala Thr Ser Asp Lys Glu Glu Ile Arg
1               5                   10                  15

Lys Leu Arg Gln Glu Val Glu Ala Leu Lys Ala Leu Val Gln Glu Gln
            20                  25                  30
```

Arg Gln Val Gln Gln Gln Gln Val Gln Gln Gln Gln Val
            35                  40                  45
Gln Leu Ala Glu Val Lys Ala Gln Pro Gln Pro Val Ala Ala Pro Val
        50                  55                  60
Ser Pro Leu Ala Gly Phe Lys Ser Lys Ala Gly Ala Asp Val Asn Leu
65                  70                  75                  80
Tyr Gly Phe Val Arg Gly Asp Ala Asn Tyr Ile Ile Glu Gly Ala Asp
                85                  90                  95
Asn Asp Phe Gly Asp Val Ser Lys Ser Asp Gly Lys Thr His Asp Lys
            100                 105                 110
Leu Arg Ala Thr Ala Lys Thr Thr Arg Leu Gly Leu Asp Phe Asn Thr
        115                 120                 125
Pro Val Gly Asp Asp Lys Val Gly Gly Lys Ile Glu Val Asp Phe Ala
130                 135                 140
Gly Ser Thr Thr Asp Ser Asn Gly Ser Leu Arg Ile Arg His Ala Tyr
145                 150                 155                 160
Leu Thr Tyr Asn Asn Trp Leu Phe Gly Gln Thr Thr Ser Asn Phe Leu
                165                 170                 175
Ser Asn His Ala Pro Glu Met Ile Asp Phe Ser Thr Asn Ile Gly Gly
            180                 185                 190
Gly Thr Lys Arg Val Pro Gln Val Arg Tyr Asn Tyr Lys Leu Gly Pro
        195                 200                 205
Thr Thr Gln Leu Phe Val Ser Ala Glu Lys Gly Asp Ser Thr Thr Ser
210                 215                 220
Val Thr Gly Asp Ser Ile Lys Tyr Ser Leu Pro Ala Leu Thr Ala Lys
225                 230                 235                 240
Ile Thr Gln Gly Tyr Ala Glu Gly Arg Gly Ser Ala Ser Ala Arg Val
                245                 250                 255
Leu Val Glu Asn Tyr Lys Ser Gln Leu Ala Asp Asp Lys Thr Gly
            260                 265                 270
Trp Gly Val Ala Val Gly Thr Asp Phe Lys Val Ser Asp Pro Leu Lys
        275                 280                 285
Leu Phe Ala Asp Ala Ser Tyr Val Val Gly Asp Asn Ser Tyr Leu Tyr
290                 295                 300
Gly Ser Asn Ser Pro Tyr Ala Val Asp Gly Asn Ser Ile Glu Gln Asn
305                 310                 315                 320
Glu Phe Val Ala Val Gln Val Gly Gly Thr Tyr Lys Ile Leu Pro Asn
                325                 330                 335
Leu Arg Ser Thr Leu Ala Tyr Gly Ala Gln Phe Ser Asp Asp Gly Thr
            340                 345                 350
Asp Tyr Ala Arg Leu Asn Ala Ser Ala Asn Glu Lys Val Gln Gln Ala
        355                 360                 365
Trp Ile Asn Phe Ile Tyr Thr Pro Val Lys Pro Ile Asp Leu Gly Val
370                 375                 380
Glu Tyr Val Asn Gly Lys Arg Asp Thr Phe Asp Gly Lys Ser Tyr Lys
385                 390                 395                 400
Asp Asn Arg Val Gly Leu Met Ala Lys Tyr Ser Phe
                405                 410

<210> SEQ ID NO 32
<211> LENGTH: 233
<212> TYPE: PRT
<213> ORGANISM: Acinetobacter baumannii

<400> SEQUENCE: 32

Tyr Gln Ala Glu Val Gly Gly Ser Tyr Asn Tyr Leu Asp Pro Asp Asn
1               5                   10                  15

Gly Ser Ser Val Ser Lys Phe Gly Val Asp Gly Thr Tyr Tyr Phe Asn
            20                  25                  30

Pro Val Gln Thr Arg Asn Ala Pro Leu Ala Glu Ala Ala Phe Leu Asn
        35                  40                  45

Arg Ala Ser Asn Val Asn Ala His Val Asn Tyr Gly Asp Asn Ser Gly
    50                  55                  60

Thr Lys Asp Thr Gln Tyr Gly Val Gly Val Glu Tyr Phe Val Pro Asn
65                  70                  75                  80

Ser Asp Phe Tyr Leu Ser Gly Asp Val Gly Arg Asn Glu Arg Glu Ile
                85                  90                  95

Asp Asn Thr Asn Ile Asp Ser Lys Val Thr Thr Tyr Ala Ala Glu Val
            100                 105                 110

Gly Tyr Leu Pro Ala Pro Gly Leu Leu Leu Ala Leu Gly Val Lys Gly
        115                 120                 125

Tyr Asp Glu Lys Asp Gly Lys Asp Gly Ala Asp Pro Thr Val Arg Ala
    130                 135                 140

Lys Tyr Val Thr Gln Val Gly Gln His Asp Val Asn Leu Glu Ala Tyr
145                 150                 155                 160

Gly Ala Phe Gly Asp Leu Asp Glu Tyr Lys Val Arg Gly Asp Tyr Tyr
                165                 170                 175

Ile Asp Lys Thr Leu Ser Leu Gly Val Asp Tyr Tyr Asn Asn Asp Leu
            180                 185                 190

Thr Asp Lys Asp Glu Phe Gly Ile Asn Ala Lys Lys Phe Leu Asn Gln
        195                 200                 205

Gln Val Ser Val Glu Gly Arg Val Gly Phe Gly Asp Asn Asp Asn Thr
    210                 215                 220

Tyr Gly Val Arg Ala Ala Tyr Arg Phe
225                 230

<210> SEQ ID NO 33
<211> LENGTH: 364
<212> TYPE: PRT
<213> ORGANISM: Acinetobacter baumannii

<400> SEQUENCE: 33

Met Gly Cys Ser Ser Asn Pro Ser Lys Lys Glu Val Val Asp Thr Gly
1               5                   10                  15

Pro Gln Ser Ser Glu Gln Ala Tyr Phe Asp Lys Ala Gln Lys Ala Leu
            20                  25                  30

Asp Arg Gly Gln Tyr Leu Asp Ala Thr Lys Ser Leu Glu Ala Ile Asp
        35                  40                  45

Thr Tyr Tyr Pro Thr Gly Gln Tyr Ala Gln Gln Ala Gln Leu Glu Leu
    50                  55                  60

Leu Tyr Ser Lys Phe Lys Gln Lys Asp Tyr Glu Gly Ala Ile Ala Leu
65                  70                  75                  80

Ala Glu Arg Phe Ile Arg Leu Asn Pro Gln His Pro Asn Val Asp Tyr
                85                  90                  95

Ala Tyr Tyr Val Arg Gly Val Ser Asn Met Glu Met Asn Tyr Asp Ser
            100                 105                 110

Leu Leu Arg Tyr Thr Ser Leu Gln Gln Ser His Arg Asp Val Ser Tyr
        115                 120                 125

Leu Lys Val Ala Tyr Gln Asn Phe Val Asp Leu Ile Arg Arg Phe Pro
130                 135                 140

Ser Ser Gln Tyr Ser Val Asp Ala Ala Gln Arg Met Lys Phe Ile Gly
145                 150                 155                 160

Gln Glu Leu Ala Glu Ser Glu Met Asn Ala Ala Arg Phe Asn Val Lys
                165                 170                 175

Arg Lys Ala Trp Ile Ala Ala Glu Arg Ser Gln Trp Val Ile Glu
            180                 185                 190

His Tyr Pro Gln Thr Pro Gln Val Pro Glu Ala Leu Ala Thr Leu Ala
            195                 200                 205

Tyr Ser Tyr Asp Gln Leu Gly Asp Lys Ala Thr Ser Gln Gln Tyr Ile
210                 215                 220

Glu Val Leu Lys Leu Asn Tyr Pro Ser Leu Val Asn Lys Asn Gly Thr
225                 230                 235                 240

Val Asn Met Arg Ala Ala Arg Lys Glu Gly Asn Trp Ile Asn Arg Ala
                245                 250                 255

Thr Leu Gly Ile Leu Gly Arg Glu Ser Lys Ser Val Thr Pro Asp Thr
            260                 265                 270

Thr Thr Ser Ser Glu Ala Glu Pro Lys Arg Ser Leu Leu Asn Arg Val
        275                 280                 285

Ser Phe Gly Leu Ile Gly Asn Ser Gly Lys Glu Glu Thr Glu Glu Thr
        290                 295                 300

Thr Asn Thr Pro Val Glu Ala Pro Lys Ser Glu Arg Ser Trp Thr Asn
305                 310                 315                 320

Arg Leu Ser Phe Gly Leu Leu Asp Lys Pro Lys Pro Lys Ala Ala Glu
                325                 330                 335

Gly Ala Thr Ile Ala Pro Ala Thr Ser Ser Ser Glu Ala Pro Ser Ala
            340                 345                 350

Ser Pro Ala Asp Asn Glu Ala Asp Ala Ala Gln
            355                 360

<210> SEQ ID NO 34
<211> LENGTH: 356
<212> TYPE: PRT
<213> ORGANISM: Acinetobacter baumannii

<400> SEQUENCE: 34

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Ser Gln His Asn Asn Gly Gly Lys Asp Gly Asn
            35                  40                  45

Leu Thr Asn Gly Pro Glu Leu Gln Asp Asp Leu Phe Val Gly Ala Ala
    50                  55                  60

Leu Gly Ile Glu Leu Thr Pro Trp Leu Gly Phe Glu Ala Glu Tyr Asn
65              70                  75                  80

Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Asp Phe Asp Gly Val Asn Arg Gly Thr Arg Gly Thr
    130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
            165                 170                 175

Ala Asp Glu Glu Phe Trp Asn Tyr Thr Ala Leu Ala Gly Leu Asn Val
        180                 185                 190

Val Leu Gly Gly His Leu Lys Pro Ala Ala Pro Val Glu Val Ala
        195                 200                 205

Pro Val Glu Pro Thr Pro Val Ala Pro Gln Pro Gln Glu Leu Thr Glu
        210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
            245                 250                 255

Ser Glu Tyr Pro Asn Ala Thr Ala Arg Ile Glu Gly His Thr Asp Asn
        260                 265                 270

Thr Gly Pro Arg Lys Leu Asn Glu Arg Leu Ser Leu Ala Arg Ala Asn
        275                 280                 285

Ser Val Lys Ser Ala Leu Val Asn Glu Tyr Asn Val Asp Ala Ser Arg
        290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
            325                 330                 335

Gly Ser Arg Thr Val Val Val Gln Pro Gly Gln Glu Ala Ala Ala Pro
        340                 345                 350

Ala Ala Ala Gln
        355

<210> SEQ ID NO 35
<211> LENGTH: 581
<212> TYPE: PRT
<213> ORGANISM: Acinetobacter baumannii

<400> SEQUENCE: 35

Met Asn Gln Glu Thr Gly Arg Gly Val Thr Arg Gly Thr Lys Leu Tyr
1               5                   10                  15

Val Lys Asp Val Pro Val Leu Ala Val Pro Tyr Phe Asn Phe Pro Ile
            20                  25                  30

Asp Asp Arg Arg Thr Thr Gly Ile Leu Asn Pro Gln Phe Gly Phe Ser
        35                  40                  45

Asn Asp Gly Gly Ile Glu Leu Ser Val Pro Val Tyr Leu Asn Leu Ala
    50                  55                  60

Pro Asn Tyr Asp Ala Thr Ile Thr Pro Arg Tyr Leu Ala Asp Arg Gly
65                  70                  75                  80

Ala Met Leu Gln Gly Glu Phe Arg Tyr Leu Thr Asp Gly Phe Gly Ala
            85                  90                  95

Gly Gln Ile Trp Gly Gly Ile Leu Pro Ser Asp Lys Glu Tyr Asp Asp
        100                 105                 110

Lys Asp Arg Lys Asp Phe His Phe Leu His Asn Trp Ile Asn Asp
        115                 120                 125

Gln Trp Ser Thr Asn Leu Glu Tyr Asn Tyr Ala Ser Asp Lys Asp Tyr
    130                 135                 140

Phe Ser Asp Leu Asp Ser Ser Pro Ile Ser Lys Thr Asp Leu Asn Leu

-continued

```
            145                 150                 155                 160
Arg Arg Ala Trp Glu Leu Asn Tyr Gln His Gly Ile Pro Gly Leu Lys
                165                 170                 175
Ala Gln Leu Lys Val Glu Asp Phe Gln Thr Leu Asp Pro Gln Val Lys
                180                 185                 190
Asp Ala Asp Lys Pro Tyr Ala Arg Leu Pro Gln Phe Leu Leu Asn Tyr
                195                 200                 205
Val Thr Gly Asn Pro Leu Gly Leu Gln Tyr Glu Phe Asn Asn Asp Thr
    210                 215                 220
Ala Tyr Phe Lys Lys Ser Ile Asn Asp Asn Ser Ala Gln Glu Ser Ser
225                 230                 235                 240
Gly Thr Arg Ile Tyr Asn Gln Phe Ala Thr Arg Tyr Asn Tyr Arg Thr
                245                 250                 255
Pro Ala Ala Phe Val Ile Pro Glu Val Ser Val Arg Ser Ile Gln Thr
                260                 265                 270
Phe Tyr Asp Lys Asp Thr Gln Leu Asn Asn Pro Gly Gly Ser Glu Asn
                275                 280                 285
Lys Ser Val Val Pro Gln Phe Thr Leu Asp Thr Gly Leu Asn Phe
    290                 295                 300
Glu Arg Glu Gly Lys Tyr Leu Gln Thr Leu Thr Pro Arg Ala Phe Tyr
305                 310                 315                 320
Ala Tyr Ala Pro Tyr Lys Asn Gln Asp Gly Tyr Pro Asn Phe Asp Ser
                325                 330                 335
Thr Thr Ala Ser Ile Ser Tyr Asp Gln Leu Phe Asn Pro Tyr Arg Phe
                340                 345                 350
Tyr Gly His Asp Arg Leu Glu Asp Asn Asn Phe Leu Ser Leu Gly Val
                355                 360                 365
Ser Tyr Ser Leu Phe Asp Thr Val Gly Leu Glu Arg Leu Arg Ala Ser
    370                 375                 380
Val Gly Gln Ser Tyr Tyr Phe Glu Asp Arg Arg Val Thr Leu Lys Gln
385                 390                 395                 400
Gly Gln Asp Glu Phe Asp Thr Glu Arg Lys Thr Gly Pro Val Ile Ser
                405                 410                 415
Leu Ser Ser Gln Leu Asn Gln Asn Phe Thr Ile Ala Ala Asn Ser Ala
                420                 425                 430
Trp Met Ser Asn Gly Asp Asn Ala Gln Arg Asp Phe Gln Val Tyr Tyr
                435                 440                 445
Thr Gly Asp Lys Gly Asn Leu Tyr Asn Leu Gly Tyr Phe Tyr Arg Lys
                450                 455                 460
Asp Ile Pro Gly Arg Gln Asp Thr Tyr Asp Gln Val Val Ala Ser Phe
465                 470                 475                 480
Ile Gln Pro Ile Lys Asp Asn Trp Arg Ile Met Gly His Val Gln Tyr
                485                 490                 495
Asp Met Asp Asn Asp Val Ala Arg Glu Leu Leu Leu Gly Val Asn Tyr
                500                 505                 510
Glu Ser Cys Cys Trp Gly Ile Ser Val Tyr Gly Arg Ser Tyr Tyr Asn
                515                 520                 525
Asp Leu Asp Asp Pro Lys Thr Ser Asp Val Ser Glu Lys Arg Ala Ile
    530                 535                 540
Met Ala Glu Ile Thr Leu Lys Gly Leu Gly Gly Leu Asn Asn Lys Leu
545                 550                 555                 560
Ala Ser Leu Leu Glu Asn Arg Phe Leu Gly Phe Asn Lys Ile Asn Gln
                565                 570                 575
```

<210> SEQ ID NO 36
<211> LENGTH: 747
<212> TYPE: PRT
<213> ORGANISM: Acinetobacter baumannii

<400> SEQUENCE: 36

Met Ser Ser Glu Lys Arg Asp Leu Thr Asn Phe Ser Arg Phe Leu Val
1               5                   10                  15

Asn Ile Asn Tyr Val Asp Phe Pro Glu Tyr Ala Lys Leu Pro Leu Ile
            20                  25                  30

Gln Asn Phe Arg Asp Phe Lys His Phe Lys Thr Ala Ile Asp Trp Ser
        35                  40                  45

Asn Lys Phe Asn Ile Gln Lys Ser Val Asp Gly Arg Ile Leu Leu Ser
    50                  55                  60

Val Leu Tyr Ala Glu Ala Gln Asp Val Ala Asn Ala Lys Asp Gln Leu
65                  70                  75                  80

Ser Lys Ile Asp Ile Lys Gly Leu Thr Ala Asp Gln Leu Val Arg Val
                85                  90                  95

Ala Tyr Ala Tyr Arg Leu Ile Asn Leu Pro Val Asp Ala Leu Ala Thr
            100                 105                 110

Val Glu His Ala Tyr Gln Gln Pro Lys Ser Leu Ser Val Leu Gln
        115                 120                 125

Glu Tyr Val Tyr Asp Leu Ile Ala Ile Gly Ser Tyr Lys Lys Ala Gln
    130                 135                 140

Gln Leu Leu Gln Ala Ser Glu Lys Thr Glu Gln Thr Val Gln Met Leu
145                 150                 155                 160

Lys Thr Leu Gln Val Ser Glu Phe Ser Gln His Ile Asn Asn Ala Ile
                165                 170                 175

Ala Arg Tyr Lys Tyr Leu Asn Arg Glu Gly Leu Ser Asp Ala Glu Ser
            180                 185                 190

Phe Ala Glu Leu Asp Lys Val Leu Glu Gln Gly Gln Lys Met His Gln
        195                 200                 205

Gln Met Asn Pro Ser Asp Pro Asn Tyr Leu Arg Phe Tyr Tyr Asp Tyr
    210                 215                 220

Leu Tyr Gly Leu Asp Phe Arg Gly Arg Ser Lys Ala Val Ile Glu Ser
225                 230                 235                 240

Phe Thr Gln Leu Asn Ile Pro Leu Glu Lys Leu Pro Ala Tyr Val Arg
                245                 250                 255

His Ala Ile Ala Asp Ser Tyr Leu Ala Glu Gln Lys Pro Lys Gln Ala
            260                 265                 270

Glu Phe Ala Tyr Lys Thr Leu Leu Thr Glu Lys Asn Tyr Pro Asp Met
        275                 280                 285

Thr Val Tyr Thr Gly Leu Tyr Tyr Ser Tyr Ile Glu Gln Glu Lys Tyr
    290                 295                 300

Lys Glu Ala Glu Gln Leu Leu Ala Glu Val Asp Arg Leu Ile Pro Thr
305                 310                 315                 320

Tyr Lys Tyr Ser Gln Ala Lys Gly Val Asp Lys Ile Ser His Pro Asp
                325                 330                 335

Arg Asp Asp Tyr Ile Ala Leu Gln Gly Met His Leu Tyr Ala Asn
            340                 345                 350

His Leu Asp Gln Ala Glu Lys His Phe Gln Lys Lys Val Glu Gln Ala

```
                355                 360                 365
Pro Ala Asn Glu Ser Leu Ile Asn Asn Leu Ala Arg Val Glu Arg Trp
370                 375                 380

Arg Glu Lys Pro Leu Glu Ala Lys Lys Thr Ile Ser Arg Leu Asn Gly
385                 390                 395                 400

Ile Asp Pro Ile Ala Lys Asp Thr Arg Ile Asn Glu Met Gln Asn Ala
                405                 410                 415

Gln Ala Leu Gly Asp Ile Pro Thr Trp Arg Lys Thr Thr Gln Asn Leu
            420                 425                 430

Val Gln Tyr Tyr Pro Asp Asp Ser Gly Val Ile Lys Ser Arg Lys Glu
        435                 440                 445

Leu Glu Asp Arg Asn Arg Ala Thr Ile Ser His Ser Thr Thr Trp Gly
    450                 455                 460

Gln Ser Lys Ala Asp Gly Arg Asp Thr Val Ser Gly Gln Asn Gly Leu
465                 470                 475                 480

Lys Asp Arg Glu Met Glu Thr Arg Leu Asn Ser Pro Trp Ile Asn Asp
                485                 490                 495

Asn Tyr Arg Leu Phe Ala Trp His Gln Asp Arg Tyr Gly Glu Tyr Arg
            500                 505                 510

Phe Gly Asp Val His Asp Gln Arg Tyr Gly Val Gly Ala Glu Trp Gln
        515                 520                 525

Ala Asn Arg Lys Ala Leu Ser Ala Ile Ser Gln Ser Thr Asp Gly
    530                 535                 540

Gly Gln Ala Gly Val Arg Leu Asp Trp Ser Gln Trp Leu Asn Asp His
545                 550                 555                 560

Trp Gln Tyr Gln Leu Gln Tyr Asn Ser Gln Ala Asp Ile Pro Leu Gln
                565                 570                 575

Ala Leu Asp Ala Gly Glu Asp Gly Gln Ser Tyr Arg Ala Ala Val Thr
            580                 585                 590

Trp Gln Lys Asp Glu Ser Arg Gln Ile Gly Ala Ser Tyr Gly Leu Thr
        595                 600                 605

Asp Ile Ser Asp Gly Asn Lys Gln Gln Glu Phe Ser Thr Phe Trp Arg
    610                 615                 620

Glu Arg Leu Phe Asp Ala Pro His His Ile Thr Tyr Gly Thr Val Arg
625                 630                 635                 640

Gly Phe Tyr Gly Thr Asn Ser Gln Asp Gln Thr Ala Tyr Phe Ser Pro
                645                 650                 655

Ser Ser His Tyr Ser Ala Glu Leu Asn Leu Ser His Asp Trp Val Thr
            660                 665                 670

Trp Arg Glu Tyr Glu Arg Ser Phe Lys Gln His Phe Glu Ala Gly Val
        675                 680                 685

Gly Leu Tyr Lys Gln Ala Asp Tyr Ser Ala Lys Pro Thr Tyr Ser Leu
    690                 695                 700

Gln Tyr Gln His Gln Trp Gln Leu Ser Arg Thr Trp Gln Leu Asn Tyr
705                 710                 715                 720

Gly Ile Gly Trp Gln Tyr His Pro Tyr Asp Gly His Asp Glu Gln His
                725                 730                 735

Thr Tyr Gly Ile Phe Gly Phe Glu Gly Arg Phe
            740                 745

<210> SEQ ID NO 37
<211> LENGTH: 381
<212> TYPE: PRT
<213> ORGANISM: Acinetobacter baumannii
```

<400> SEQUENCE: 37

```
Met Leu Gly Asp Trp Asn Gly Gln Arg Thr Ala Leu Gln Ala Gln Gly
1               5                   10                  15

Tyr Asp Phe Ser Phe Gly Tyr Thr Gly Glu Tyr Ala Gly Ile Leu Asp
            20                  25                  30

Ser Lys Gln Thr Ser Thr His Gly Ser Ala Tyr Thr Gly Gln Leu Ala
        35                  40                  45

Leu Gly Ser His Leu Asp Leu Gly Lys Ile Leu Gly Trp Gln Asp Thr
    50                  55                  60

Glu Ala Gln Ile Thr Leu Thr Tyr Arg Asp Gly Gln Ser Leu Ser Glu
65                  70                  75                  80

His Ser Pro Ala Leu Ala Gly His Gln Ser Ser Val Gln Glu Val Trp
                85                  90                  95

Gly Arg Glu Gln Thr Trp Arg Leu Thr Asp Leu Trp Ile Lys Lys Lys
            100                 105                 110

Phe Leu Asp Gln Lys Leu Asp Val Lys Val Gly Arg Phe Gly Glu Gly
        115                 120                 125

Glu Asp Phe Asn Ser Phe Asp Cys Asp Phe Gln Asn Leu Ala Leu Cys
    130                 135                 140

Gly Ser Gln Val Gly Asn Trp Val Gly Asp Gln Trp Tyr Asn Trp Pro
145                 150                 155                 160

Val Ser Gln Trp Ala Met Arg Val Lys Tyr Asn Leu Gln Pro Asp Leu
                165                 170                 175

Tyr Thr Gln Val Gly Val Tyr Glu Tyr Asn Pro Glu Asn Leu Glu Arg
            180                 185                 190

Gly Lys Gly Phe Asn Leu Ser Thr Asp Gly Ser His Gly Ala Ile Ile
        195                 200                 205

Pro Ala Glu Val Val Trp Ser Pro Lys Leu Gly Val Gln Ser Met Pro
    210                 215                 220

Gly Glu Tyr Arg Leu Gly Tyr Tyr Ser Thr Ala Asp Ala Lys Glu
225                 230                 235                 240

Ile Ala Asp Ser Thr Lys Thr Ser His Lys Gln Gly Val Trp Val Thr
                245                 250                 255

Ala Lys Gln Lys Leu Phe Gln Pro Ala Asp Gln Thr Asp Arg Gly Leu
            260                 265                 270

Thr Gly Phe Val Asn Leu Thr Phe His Asp Ser Asp Thr Asn Lys Val
        275                 280                 285

Asp Asn Met Gln Asn Ile Gly Leu Val Tyr Lys Gly Leu Leu Asn Gln
    290                 295                 300

Arg Pro Gln Asp Glu Leu Ala Leu Gly Val Ala Arg Ile His Ile Asn
305                 310                 315                 320

Asp Asp Trp Ser Asp Val Gln Ala Lys Glu Tyr Asp Thr Glu Tyr Asn
                325                 330                 335

Thr Glu Leu Tyr Tyr Gly Ile His Ala Thr Asn Trp Leu Thr Ile Arg
            340                 345                 350

Pro Asn Val Gln Tyr Val Arg His Val Gly Ala Leu Lys Asn Gly Asp
        355                 360                 365

Asn Thr Trp Val Gly Gly Ile Lys Phe Ser Thr Ala Phe
    370                 375                 380

<210> SEQ ID NO 38
<211> LENGTH: 183
<212> TYPE: PRT
```

<213> ORGANISM: Acinetobacter baumannii

<400> SEQUENCE: 38

Met Leu Phe Arg Thr Gly Leu Ala Asp Gly Leu Glu Leu Gln Leu Gly
1               5                   10                  15

Trp Gln Gly Pro Ala Trp Thr Gln Thr Lys Arg Ala Gly Lys Lys Thr
            20                  25                  30

Asp Asn Ser Gly Phe Gly Asp Val Ser Ile Gly Leu Lys Lys Ala Ile
        35                  40                  45

Asp Leu Asn Asp Glu Asn Leu Thr Met Ala Val Leu Ala Glu Ala Val
    50                  55                  60

Ile Ala Thr Gly Asn Asp Glu Phe Thr Ala His Asp Asp Ile Tyr Ser
65                  70                  75                  80

Leu Ser Ser Ala Val Ala Tyr Lys Tyr Asn Asp Leu Leu Asp Thr Ser
                85                  90                  95

Ile Thr Met Arg Tyr Glu Val Gln Asn Ser Asn Trp Ala Val Thr Ala
            100                 105                 110

Ile Pro Thr Ile Asn Tyr Lys Ile Ala Gly Lys Leu Ser Gly Tyr Ser
        115                 120                 125

Glu Phe Val Tyr Arg Lys Ala Glu Ser Gln Asp Tyr Gln Tyr Gly Leu
    130                 135                 140

Gly Thr Gly Leu Val Tyr Ala Val Asn Asn Arg Thr Gln Leu Asp Ala
145                 150                 155                 160

Asn Ile Gly Val Asp Leu Glu Gly Gln Asp Lys Ser Tyr Lys Gly Gly
                165                 170                 175

Leu Gly Met Ala Phe Leu Phe
            180

<210> SEQ ID NO 39
<211> LENGTH: 217
<212> TYPE: PRT
<213> ORGANISM: Acinetobacter baumannii

<400> SEQUENCE: 39

Met Arg Ala Leu Val Ile Ser Thr Val Val Gly Ala Ala Val Val Leu
1               5                   10                  15

Ser Gly Cys Gln Thr Thr Gly Asn Asn Leu Gly Gly Val Glu Tyr Asp
            20                  25                  30

Lys Ala Ala Leu Gly Thr Leu Ile Gly Ala Ala Ala Gly Tyr Gly Ile
        35                  40                  45

Ser Lys Ser Asn Ala Asn Ser Ser Arg Gln Asn Asn Arg Ala Ala Ala
    50                  55                  60

Ile Gly Ala Val Leu Gly Ala Ala Gly Gly Leu Tyr Leu Asp Gln Lys
65                  70                  75                  80

Glu Lys Lys Leu Arg Glu Gln Met Ala Gly Thr Gly Val Glu Val Gly
                85                  90                  95

Arg Asn Pro Asp Gly Ser Val Gln Leu Ile Met Pro Gly Ser Ile Thr
            100                 105                 110

Phe Asp Thr Asn Lys Ser Asn Ile Lys Pro Asn Phe Tyr Ala Thr Leu
        115                 120                 125

Asp Lys Val Ala Gln Thr Leu Ala Glu Asp Asn Lys Ser Ala Ile Leu
    130                 135                 140

Val Thr Gly Tyr Thr Asp Asn Thr Gly Asn Asp Ser Ile Asn Ile Pro
145                 150                 155                 160

Leu Ser Gln Ala Arg Ala Gln Ser Val Lys Asn Tyr Leu Ala Gly Lys

```
                        165                 170                 175
Gly Val Pro Ser Ser Arg Ile Asp Ala Gln Gly Tyr Gly Ser Ser Asn
                180                 185                 190

Pro Ile Ala Asp Asn Ser Thr Ala Ser Gly Arg Glu Gln Asn Arg Arg
            195                 200                 205

Val Glu Ile Ser Ile Tyr Ala Lys Gln
    210                 215

<210> SEQ ID NO 40
<211> LENGTH: 299
<212> TYPE: PRT
<213> ORGANISM: Acinetobacter baumannii

<400> SEQUENCE: 40

Met Lys Lys Leu Gly Leu Ala Thr Ala Val Leu Leu Ala Met Thr Gly
1               5                   10                  15

Ala His Ala Tyr Gln Phe Glu Val Gly Gln Ser Glu Tyr Val Asp
            20                  25                  30

Thr Thr Ala Asn Asp Lys Asn Phe Thr Gly Asp Val Ala Gly Thr Phe
        35                  40                  45

Tyr Leu Lys Asn Val Asp Thr Ala Lys Gly Pro Leu Ala Glu Ala Ala
    50                  55                  60

Phe Leu Asn Gln Ala Ser Ser Val Ser Leu Gly Tyr Ser Tyr Gln Gln
65                  70                  75                  80

Tyr Asp Gln Asn Asn Val Asn Tyr His Ile Gly Thr Tyr Gly Val Lys
                85                  90                  95

Gly Glu Ala Tyr Val Pro Thr Pro Tyr Leu Pro Val Tyr Ala Ser Ala
            100                 105                 110

Thr Tyr Asn His Thr Asp Val Asp Gly Lys Asn Asn Phe Ser Lys Asp
        115                 120                 125

Asp Asn Gly Asp Arg Tyr Ala Leu Glu Val Gly Ala Met Leu Leu Pro
    130                 135                 140

Asn Phe Leu Met Thr Val Gly Tyr Thr Ser Val Ala Asn Gln Phe Ala
145                 150                 155                 160

Leu Asp Asn Phe Gly Ile Ile Gly Asn Gly Ile Tyr Ser Ala Val Asn
                165                 170                 175

Gln Thr Ala Ala Ile Gln Asn Asp Gln Asp Ala Val Thr Ala Arg Ala
            180                 185                 190

Lys Tyr Val Gly Pro Ile Asp Gly Thr Asn Met Ala Ile Gly Phe Glu
        195                 200                 205

Ala Ala Gly Ala Phe Gly Gln Glu Asn Gln Tyr Gly Leu Lys Thr Asp
    210                 215                 220

Leu Tyr Leu Thr Pro Lys Leu Ser Val Gly Ala Thr Phe Val Gly Asn
225                 230                 235                 240

Asp Gly Glu Ala Asp Ile Lys Gly Asn Asp Leu Gly Glu Phe Arg Gln
                245                 250                 255

Ala Trp Gly Gly Asn Val Asn Tyr Phe Ile Thr Pro Ala Leu Ala Val
            260                 265                 270

Gly Ala Ser Tyr Met Lys Ala Asp Val Lys Lys Ser Ser Tyr Asp Thr
        275                 280                 285

Gln Thr Ile Gly Leu Asn Ala Lys Phe Arg Phe
    290                 295

<210> SEQ ID NO 41
<211> LENGTH: 228
```

<212> TYPE: PRT
<213> ORGANISM: Acinetobacter baumannii

<400> SEQUENCE: 41

```
Asp Glu Ala Val Val His Asp Ser Tyr Ala Phe Asp Lys Asn Gln Leu
1               5                   10                  15

Ile Pro Val Gly Ala Arg Ala Glu Val Gly Thr Thr Gly Tyr Gly Gly
            20                  25                  30

Ala Leu Leu Trp Gln Ala Asn Pro Tyr Val Gly Leu Ala Leu Gly Tyr
        35                  40                  45

Asn Gly Gly Asp Ile Ser Trp Thr Asp Asp Val Ser Val Asn Gly Thr
    50                  55                  60

Lys Tyr Asp Leu Asp Met Asp Asn Asn Val Tyr Leu Asn Ala Glu
65                  70                  75                  80

Ile Arg Pro Trp Gly Ala Ser Thr Asn Pro Trp Ala Gln Gly Leu Tyr
                85                  90                  95

Ile Ala Ala Gly Ala Ala Tyr Leu Asp Asn Asp Tyr Asp Leu Ala Lys
            100                 105                 110

Arg Ile Gly Asn Gly Asp Thr Leu Ser Ile Asp Gly Lys Asn Tyr Gln
        115                 120                 125

Gln Ala Val Pro Gly Gln Glu Gly Gly Val Arg Gly Lys Met Ser Tyr
    130                 135                 140

Lys Asn Asp Ile Ala Pro Tyr Leu Gly Phe Gly Phe Ala Pro Lys Ile
145                 150                 155                 160

Ser Lys Asn Trp Gly Val Phe Gly Glu Val Gly Ala Tyr Tyr Thr Gly
                165                 170                 175

Asn Pro Lys Val Glu Leu Thr Gln Tyr Asn Leu Ala Pro Val Thr Gly
            180                 185                 190

Asn Pro Thr Ser Ala Gln Asp Ala Val Asp Lys Glu Ala Asn Glu Ile
        195                 200                 205

Arg Asn Asp Asn Lys Tyr Glu Trp Met Pro Val Gly Lys Val Gly Val
    210                 215                 220

Asn Phe Phe Trp
225
```

<210> SEQ ID NO 42
<211> LENGTH: 609
<212> TYPE: PRT
<213> ORGANISM: Acinetobacter baumannii

<400> SEQUENCE: 42

```
Met Gly Phe Asn Ser Ile Gln Ser Gly Gly Thr Asn Gly Asp Val Thr
1               5                   10                  15

Phe Arg Gly Met Phe Gly Ser Arg Ile Lys Ile Leu Thr Asp Gly Thr
            20                  25                  30

Glu Asn Leu Gly Ala Cys Pro Asn Arg Met Asp Ala Pro Thr Ser Tyr
        35                  40                  45

Ile Ser Pro Glu Ser Tyr Asp Arg Ile Ser Val Ile Lys Gly Pro Gln
    50                  55                  60

Thr Val Gln Tyr Ala Asn Thr Gly Ser Ala Ala Thr Val Leu Phe Glu
65                  70                  75                  80

Arg Gln Pro Glu Lys Leu Thr Ser Glu Lys Pro Tyr Arg Gly Gln Ala
                85                  90                  95

Ser Val Leu Leu Gly Ser Tyr Gly Arg Ile Asp His Asn Ile Glu Ala
            100                 105                 110
```

Ala Val Gly Asp Glu Lys Lys Tyr Ile Arg Leu Asn Ala Asn Arg Ser
            115                 120                 125

Glu Ser Asn Ser Tyr Gln Asp Gly Asp Gly Asn Thr Val Pro Ser Ala
    130                 135                 140

Trp Lys Lys Trp Asn Ala Asp Val Ala Leu Gly Phe Thr Pro Asp Glu
145                 150                 155                 160

Asn Thr Trp Val Glu Ile Thr Gly Gly Lys Ser Asp Gly Glu Ser Leu
                165                 170                 175

Tyr Ala Gly Arg Ser Met Asp Gly Ser Gln Phe Ala Arg Glu Ser Leu
            180                 185                 190

Gly Leu Arg Phe Glu Lys Lys Asn Ile Thr Asp Val Ile Lys Lys Ile
        195                 200                 205

Glu Gly Gln Val Asn Tyr Ser Tyr Asn Asp His Val Met Asp Asn Phe
    210                 215                 220

Arg Leu Arg Ile Pro Pro Met Thr His Asp Met Met Thr His Gln Met
225                 230                 235                 240

Val Val Asn Pro Ser Glu Met Gln Val Thr Arg Arg Thr Leu Asn Thr
                245                 250                 255

Arg Phe Ala Met Thr Ser Glu Trp Gly Lys Leu Asn Val Ile Thr Gly
            260                 265                 270

Ile Asp Ser Gln Gln Asn His His Ala Glu Ser Met Lys Ser Leu Met
        275                 280                 285

Met Asp Met Pro Leu Thr Thr Asn Met Lys Phe Gln Ser Tyr Gly Ala
    290                 295                 300

Phe Gly Glu Leu Gly Tyr Gln Leu Ser Glu Asn Ser Lys Leu Val Thr
305                 310                 315                 320

Gly Ala Arg Leu Asp Gln Val Lys Ile Asp Ala Leu Lys Leu Asn Asp
                325                 330                 335

Asp Arg Ser Glu Thr Leu Pro Ser Gly Phe Ile Arg Leu Glu Thr Gln
            340                 345                 350

Leu Pro Glu His Asn Ala Lys Ser Tyr Ile Gly Leu Gly Tyr Val Glu
        355                 360                 365

Arg Val Pro Asp Tyr Trp Glu Leu Phe Ser Thr Ala His Gly Asn Ser
    370                 375                 380

Gly Met Pro Lys Pro Thr Phe Asn Asp Leu Asp Thr Glu Lys Thr Leu
385                 390                 395                 400

Gln Leu Asp Met Gly Tyr Gln His Gln Gly Ala Phe Asn Ser Trp
                405                 410                 415

Ala Ser Ala Tyr Val Gly Leu Ile Asn Asp Tyr Ile Leu Met Ser Tyr
            420                 425                 430

His Asn His Pro Thr Ser Gly Gly His Gly His Gly Ser Ser Phe Ser
        435                 440                 445

Ala Gly Ala Lys Asn Val Asp Ala Thr Ile Ala Gly Ala Glu Ala Gly
    450                 455                 460

Ile Gly Tyr Gln Phe Thr Asp Arg Ile Gln Ala Asp Leu Ser Ala Met
465                 470                 475                 480

Tyr Ala Trp Gly Lys Asn Thr Thr Asp Asp Lys Pro Leu Pro Gln Ile
                485                 490                 495

Ser Pro Leu Glu Gly Arg Leu Asn Ile Arg Tyr Val Ala Asp Lys Tyr
            500                 505                 510

Asn Leu Gly Leu Leu Trp Arg Ala Val Ala Glu Gln Asn Arg Val Ser
        515                 520                 525

Leu His Gln Gly Asn Ile Val Gly Tyr Asp Leu Lys Pro Ser Lys Gly

```
                530             535             540
Phe Ser Thr Leu Ser Leu Asn Gly Ser Tyr Asn Leu Arg Lys Asp Ile
545                 550                 555                 560

Asp Val Ser Val Gly Ile Asp Asn Val Leu Asp Lys Thr Tyr Thr Glu
                565                 570                 575

His Leu Asn Lys Ala Gly Ser Ala Gly Phe Gly Phe Ala Ser Glu Glu
            580                 585                 590

Gln Phe Asn Asn Ile Gly Arg Asn Tyr Trp Val Arg Met Ser Met Lys
        595                 600                 605

Phe
```

<210> SEQ ID NO 43
<211> LENGTH: 170
<212> TYPE: PRT
<213> ORGANISM: Acinetobacter baumannii

<400> SEQUENCE: 43

```
Met Thr Gly Cys Ala Ser Arg Lys Pro Ala Thr Thr Ala Thr Thr Gly
1               5                   10                  15

Thr Thr Asn Pro Ser Thr Val Asn Thr Thr Gly Leu Ser Glu Asp Ala
            20                  25                  30

Ala Leu Asn Ala Gln Asn Leu Ala Gly Ala Ser Ser Lys Gly Val Thr
        35                  40                  45

Glu Ala Asn Lys Ala Ala Leu Ala Lys Arg Val Val His Phe Asp Tyr
    50                  55                  60

Asp Ser Ser Asp Leu Ser Thr Glu Asp Tyr Gln Thr Leu Gln Ala His
65                  70                  75                  80

Ala Gln Phe Leu Met Ala Asn Ala Asn Ser Lys Val Ala Leu Thr Gly
                85                  90                  95

His Thr Asp Glu Arg Gly Thr Arg Glu Tyr Asn Met Ala Leu Gly Glu
            100                 105                 110

Arg Arg Ala Lys Ala Val Gln Asn Tyr Leu Ile Thr Ser Gly Val Asn
        115                 120                 125

Pro Gln Gln Leu Glu Ala Val Ser Tyr Gly Lys Glu Ala Pro Val Asn
    130                 135                 140

Pro Gly His Asp Glu Ser Ala Trp Lys Glu Asn Arg Arg Val Glu Ile
145                 150                 155                 160

Asn Tyr Glu Ala Val Pro Pro Leu Leu Lys
                165                 170
```

<210> SEQ ID NO 44
<211> LENGTH: 480
<212> TYPE: PRT
<213> ORGANISM: Acinetobacter baumannii

<400> SEQUENCE: 44

```
Met Phe Leu Arg Lys Thr Leu Ser Ile Ala Leu Leu Ala Thr Ala Ser
1               5                   10                  15

Ser Ala Val Phe Ala Gln Gly Leu Val Leu Asn Asn Asp Asp Leu Arg
            20                  25                  30

Thr Asp Leu Asn Trp Leu Asn Gln Gln Gly Val Ile Asn Ile Ser Thr
        35                  40                  45

Ser Thr Trp Pro Leu Ser Gly Asp Glu Ile Gln Arg Ala Leu Ser Gln
    50                  55                  60

Ala Lys Val Thr His Pro Ala Gln Gln Lys Val Ile Asn Ser Val Leu
65                  70                  75                  80
```

Asn Ala Leu Lys Ala Asp Asn Thr Val Lys Val Gly Ala Phe Ala
                85                  90                  95

Glu Ser Asp Ile Lys Asn Ile Pro Gln Ala Phe Gly Asp Asn Gln Lys
                100                 105                 110

Ser Gln Tyr Gln Gly Ser Leu Glu Phe Asn Ala Gly Gly Glu Asn Trp
        115                 120                 125

Asp Ala Lys Ile Arg Val Asn Ala Glu Lys Asp Pro Gln Ile Asp Ser
    130                 135                 140

Gly His Asp Val Asn Val Glu Gly Ser Tyr Val Ala Gly Lys Leu Trp
145                 150                 155                 160

Asn Gln Trp Ile Val Ala Gly Gln Ile Pro Thr Trp Gly Pro Gly
                165                 170                 175

His Asp Gly Ser Leu Ile Arg Gly Asp Ala Ser Arg Pro Val Tyr Gly
                180                 185                 190

Val Thr Ala Gln Arg Ala Val Gln Asn Ala Phe Glu Thr Lys Trp Leu
        195                 200                 205

Ser Trp Ile Gly Pro Trp Gln Tyr Gln Ala Phe Ala Gly Gln Leu Asp
    210                 215                 220

Asp Tyr Lys Ala Val Pro Asp Ala Lys Leu Ile Gly Leu Arg Leu Thr
225                 230                 235                 240

Ala Gln Pro Leu Pro Tyr Leu Glu Leu Gly Ala Ser Arg Thr Ile Gln
                245                 250                 255

Trp Gly Gly Asp Gly Arg Ser Glu Ser Phe Ser Ser Leu Trp Asp Ala
                260                 265                 270

Ile Lys Gly Asn Asp Asn Val Tyr Gly Asp Thr Glu Asn Pro Ser Asn
        275                 280                 285

Gln Leu Ala Gly Phe Asp Gly Arg Leu Leu Gln Pro Leu Leu Asn
    290                 295                 300

Ile Pro Val Ser Leu Tyr Gly Gln Tyr Val Gly Glu Asp Ala Gly
305                 310                 315                 320

Tyr Leu Pro Ser Lys Lys Met Tyr Leu Ala Gly Val Asp Tyr Ser Ser
                325                 330                 335

Ser Tyr Asn Asp Met Pro Tyr Gln Leu Tyr Ala Glu Trp Ala Asp Thr
                340                 345                 350

Arg Thr Asn Gly Asp Val Lys Ser Ile Ser Tyr Thr His Ser Val Tyr
        355                 360                 365

Lys Asp Gly Tyr Tyr Gln His Gly Phe Pro Leu Gly His Ala Met Gly
    370                 375                 380

Gly Asp Gly Gln Met Tyr Ser Val Gly Gly Asp Ile Arg Phe Asp Val
385                 390                 395                 400

Met Asn Arg Leu Ser Gly Arg Ala Met Val Lys Val Asn Gln Ser
                405                 410                 415

Asn Leu Ala Ile Asn Lys Ala Phe Pro Lys Asp Asp Glu Ile Lys Ala
                420                 425                 430

Leu Asp Leu Thr Trp Thr His Tyr Ile Lys Pro Asp Leu Pro Leu Lys
        435                 440                 445

Ile Asn Gly Trp Val Ser Asp Ser Asp Leu Glu Gly Asn Asp Ala Gly
    450                 455                 460

Ala Ser Ile Gly Val Glu Ile Pro Leu Glu Arg Lys Met Phe Gly Phe
465                 470                 475                 480

<210> SEQ ID NO 45
<211> LENGTH: 114

```
<212> TYPE: PRT
<213> ORGANISM: Acinetobacter baumannii

<400> SEQUENCE: 45

Met Asn Lys Leu Leu Val Ala Leu Gly Leu Ala Ala Thr Val Ala Leu
1               5                   10                  15

Val Gly Cys Asn Lys Asp Lys Ala Pro Glu Thr Gly Ala Thr Thr Gly
            20                  25                  30

Glu His Leu Glu Asn Ala Ala Gln Gln Ala Thr Ala Asp Ile Lys Ser
        35                  40                  45

Ala Gly Asp Gln Ala Ala Ser Asp Ile Ala Thr Ala Thr Asp Asn Ala
    50                  55                  60

Ser Ala Lys Ile Asp Ala Ala Asp His Ala Ala Asp Ala Thr Ala
65                  70                  75                  80

Lys Ala Ala Ala Glu Thr Glu Ala Thr Ala Arg Lys Ala Thr Ala Asp
                85                  90                  95

Thr Ala Gln Ala Val Glu Asn Ala Ala Ala Asp Val Lys Lys Asp Ala
            100                 105                 110

Gln His

<210> SEQ ID NO 46
<211> LENGTH: 725
<212> TYPE: PRT
<213> ORGANISM: Acinetobacter baumannii

<400> SEQUENCE: 46

Met Tyr Glu Tyr Pro Ser Tyr Asp Tyr Arg Gly Asn Phe Lys Ile Thr
1               5                   10                  15

Val Asp Pro Ser Gln Ile Lys Gln Asn Val Lys Ala Glu Asn Thr Ala
            20                  25                  30

Lys Leu Asp Ala Glu Leu Gln Lys Val Asp Gln Tyr Leu Arg Glu
        35                  40                  45

Gln Lys Val Ala Leu Ser Lys Ala Gln Lys Gln Thr Leu Tyr Ala Ala
    50                  55                  60

Ile Ala Asn Glu Gln Gly Asp Trp Gly Leu Thr Ser Ser Ala Arg Ser
65                  70                  75                  80

Glu Lys Ile Asn Asn Ile Leu Ile Asn Leu Leu Asn Asp Leu Gln Phe
                85                  90                  95

Ser Tyr Asp Gly Ser Ile His Tyr Arg Gln Lys Met Gly Ser Phe Asn
            100                 105                 110

Leu Thr Ala Arg Tyr Glu Lys Pro Thr Leu Leu Val Gln Ala Lys Leu
        115                 120                 125

Pro Met Val Leu Asp Leu Glu Asn Tyr Lys Phe Tyr Ile Asn Tyr Phe
    130                 135                 140

Gly Leu Met Pro Tyr Leu Val Asn Lys Asp Asn Gln Asn Leu Ala
145                 150                 155                 160

Tyr Val Asp Phe Ser Lys Tyr Lys Ala Phe Phe Lys Asn Val Asp Lys
                165                 170                 175

Lys Lys Phe Ile Glu Tyr Leu Lys Ala Ser Ser Ala Val Ser Tyr Arg
            180                 185                 190

Leu Ala Glu Pro Gln Asn Leu Gln Arg Val Ser Leu Thr Glu Ala Asp
        195                 200                 205

Arg Lys Ala Gly Ala Val Glu Arg Ile Arg Leu Lys Thr Thr Val Glu
    210                 215                 220

Gln Leu Leu Leu Glu Val Asp Leu Phe Gly Gln Val Asn Glu Lys Tyr
```

```
              225                 230                 235                 240
Leu Gln Lys Ser Val Leu Gly Leu Asp Glu Glu Lys Leu Ala Glu Thr
                    245                 250                 255

Leu Ala Ala Glu Ile Ala Ala Ser Asp Ala Lys Lys Gly Thr Ala Gly
                260                 265                 270

Lys Glu Glu Gln Lys Val Ser Ser Asp Ala Ala Ala Val Ser Gln
            275                 280                 285

Gln Leu Tyr Ser Leu Val Asn Ala His Leu Gly Asn Thr Ser Thr Ser
        290                 295                 300

Glu Asp Glu Glu Val Glu Ser Ala Ser Ser Glu Glu Ala Ser Asp Val
305                 310                 315                 320

Ala Val Ala Glu Ala Glu Gln Thr Ser Glu Asn Glu Val Val Val
                325                 330                 335

Leu Thr Glu Asp Gln Cys Ile Glu Leu Lys Ser Leu Lys Asn Pro Val
                340                 345                 350

Ala Leu Gly Asp Ile Asn Tyr Cys Gln Ile Tyr Gly Ile Asp Val Leu
            355                 360                 365

Asp Gln Ser Asp Thr Ser Ile Gln Lys Ala Gln Ile Lys Ser Arg Gln
        370                 375                 380

Asp Ala Leu Lys Gln Thr Phe Glu Val Tyr Asn Gln Asn Gln Phe Ile
385                 390                 395                 400

Asn Asp Glu Ala Phe Lys Val Leu Trp Leu Lys His Lys Asp Glu Ile
                405                 410                 415

Glu Gln Ala Leu Pro Lys Gln Arg Asn Pro Ile Thr Ile Asp Val Ala
            420                 425                 430

Leu Asp Asp Lys Gly Arg Ala Val Asn Met Asp Tyr Asp Val Asp Tyr
        435                 440                 445

Thr Pro Ala Glu Phe Lys His Arg Phe Asn Ile Lys Ala Asp Met Gln
    450                 455                 460

Ile Leu Asn Tyr Gly Lys Ala Thr Ser Ile Asp Gln Gln Leu Lys
465                 470                 475                 480

Gln Ala Lys Ser Val Ala Glu Ala Ser Lys Gly Ser Met Leu Glu Asn
                485                 490                 495

Ile Ile Lys Gly Phe Ser Glu Lys Leu Gly Gln Ser Asp Val Ser Glu
            500                 505                 510

His Pro Val Gly Thr His Ser Asp Val Gln Asp Leu Asp Ala Asn Leu
        515                 520                 525

Ala Ile Leu Ala Asp Lys Thr Tyr Asp Ala Thr His Ala Tyr Asp Lys
    530                 535                 540

Thr Tyr Lys Ala Val Phe Ile Ala Lys Leu Thr Ala Glu Lys Pro Ser
545                 550                 555                 560

Tyr Ile Lys Tyr Tyr Ser Val Gln Gln Leu Gln Glu Ile Ala Glu Val
                565                 570                 575

Tyr Ala Tyr Trp Phe Ser Asp Glu Asp Thr Tyr Asn Pro Gln Gly Lys
            580                 585                 590

Ala Leu Glu Arg Ile Thr Ala Leu Gln Lys Lys His His Leu Glu Gln
        595                 600                 605

Asp Asp Gln Phe Asp His Glu Leu Gly Arg Ala Val Asp His Ile Val
    610                 615                 620

Leu Thr Thr Ile Gln Gly Lys Thr Gly Arg Glu Ala Trp Gln Arg Leu
625                 630                 635                 640

Gln Lys Gln Tyr Lys Gln Pro Ala Gln Leu Phe Ser Lys Gln Tyr Gln
                645                 650                 655
```

```
Leu Glu Phe Glu Lys Gln Asn Gly Val Ser Ala Glu Lys His Leu
                660                 665                 670

Leu Ser Glu Thr Ala Asp Ile Leu Gly Asn Val Tyr Val Ala Ala His
            675                 680                 685

Lys Lys Gln Leu Ser Glu Lys Thr Ile Gln Asn Leu Lys Pro Glu His
690                 695                 700

Asn Glu Phe Ile Asp Tyr Glu Ile Phe Arg Glu Val Tyr Lys Gln Met
705                 710                 715                 720

Val Ala Ala Arg Lys
                725

<210> SEQ ID NO 47
<211> LENGTH: 746
<212> TYPE: PRT
<213> ORGANISM: Acinetobacter baumannii

<400> SEQUENCE: 47

Met Thr Pro Cys Cys Leu Ala Ile Ser Ala Ile Phe Ala Gln Gln Ala
1               5                   10                  15

Tyr Ala Glu Thr Val Thr Gln Thr Ala Glu Val Ser Glu Asn Ala Thr
            20                  25                  30

Gln Lys Pro Val Ala Gln Leu Gln Lys Ile Val Val Thr Ala Thr Arg
        35                  40                  45

Thr Pro Lys Asn Ile Ala Glu Ile Ala Gly Thr Val Gln Ser Ile Asp
    50                  55                  60

Gln Lys Gln Ile Ile Gln Gln Ala Thr Ala Gly Arg Lys Val Ala Asp
65                  70                  75                  80

Ile Leu Ala Gln Leu Val Pro Ser Leu Ala Ser Ser Gly Thr Thr
                85                  90                  95

Ser Asn Tyr Gly Gln Thr Met Arg Gly Arg Asn Val Leu Val Met Ile
            100                 105                 110

Asp Gly Val Ser Gln Thr Gly Ser Arg Asp Val Ser Arg Gln Leu Asn
        115                 120                 125

Ser Ile Ser Pro Gly Met Ile Glu Arg Ile Glu Val Ile Ser Gly Ala
    130                 135                 140

Thr Ser Ile Tyr Gly Ser Gly Ala Thr Gly Gly Ile Ile Asn Ile Ile
145                 150                 155                 160

Thr Lys Arg Ala Asp Thr Ser Lys Pro Leu Ser Phe Glu Thr Lys Val
                165                 170                 175

Gly Ile Thr Ser Ser Asp Thr Phe Arg Ser Asp Gly Leu Ala Tyr Glu
            180                 185                 190

Val Gly Gln Ser Val Ser Phe Asn Lys Gly Asn Ile Asp Gly Phe Leu
        195                 200                 205

Gly Ala Asn Phe Thr Ser Arg Gly Ser Gln Phe Asp Gly Asn Gly Asp
    210                 215                 220

Arg Ile Ser Leu Ser Pro Trp Gln Gly Ser Thr Met Asp Thr Asp Thr
225                 230                 235                 240

Ile Asp Val Asn Gly Arg Leu Asn Phe Asn Leu Asn Asp Thr Gln Thr
                245                 250                 255

Leu Ser Phe Gly Ala Gln Tyr Tyr Lys Asp Lys Gln Thr Asp Tyr
            260                 265                 270

Gly Pro Asp Tyr Ser Tyr Leu Pro Thr Thr Ser Lys Ser Asn Asp Ala
        275                 280                 285

Thr Thr Pro Thr Tyr Lys Ala Ile Lys Gly Leu Lys Leu Ser Asn Pro
```

```
              290                 295                 300
Leu Phe Thr Glu Arg Tyr Ala Val Asn Ser Gln Tyr Gln Asn Gln Asp
305                 310                 315                 320

Phe Leu Gly Gln Ile Leu Asn Val Glu Ala Tyr Tyr Arg Asn Glu Lys
                    325                 330                 335

Ser Arg Phe Phe Pro Tyr Gly Leu Ser Asn Lys Ser Val Thr Ser Val
                340                 345                 350

Asn Gln Ser Gln Ser Glu Ile Glu Val Ala Gly Leu Arg Ser Thr Met
            355                 360                 365

Gln Thr Asp Leu Asn Ile Ala Asn Arg Asp Met Lys Ile Thr Tyr Gly
        370                 375                 380

Leu Asp Tyr Asp Trp Glu Lys Asp Lys Gln Phe Val Asp Ile Leu Ala
385                 390                 395                 400

Thr Gln Tyr Pro Tyr Leu Val Tyr Thr Pro Thr Gly Gln Arg Lys Gly
                405                 410                 415

Tyr Gly Pro Asn Thr Glu Ile Gln Asn Ile Gly Ala Phe Val Gln Ser
                420                 425                 430

Asp Tyr Ala Val Thr Asp Lys Leu Asn Leu Gln Ala Gly Ile Arg Tyr
            435                 440                 445

Gln Tyr Ile Gln Ala Asp Thr Asp Ala Tyr Ile Pro Ser Arg Glu Thr
        450                 455                 460

Thr Met Val Pro Ala Gly Ser Thr His Asp Asp Lys Pro Leu Phe Asn
465                 470                 475                 480

Leu Gly Ala Val Tyr Lys Leu Thr Asp Ala Gln Gln Val Tyr Ala Asn
                485                 490                 495

Phe Ser Gln Gly Phe Ser Phe Pro Asp Val Gln Arg Met Leu Arg Asp
                500                 505                 510

Val Ser Thr Tyr Thr Val Ser Thr Ala Asn Leu Gln Pro Ile Thr Val
            515                 520                 525

Asn Ser Tyr Glu Leu Gly Trp Arg Leu Asn Gln Asp Asp Gly Leu Asn
        530                 535                 540

Leu Gly Leu Thr Gly Phe Tyr Asn Thr Ser Asp Lys Thr Val Gln Phe
545                 550                 555                 560

Asn Asn Arg Ala Ala Lys Val Val Asp Thr Asp Gln Arg Val Tyr Gly
                565                 570                 575

Ala Glu Ala Thr Ile Ser Tyr Pro Phe Met Glu Asn Tyr Lys Val Gly
                580                 585                 590

Gly Thr Leu Gly Tyr Thr Arg Gly Gln Tyr Lys Asp Val Ala Asn Lys
            595                 600                 605

Trp His Glu Leu Asn Ser Phe Thr Val Ala Pro Val Lys Gly Thr Leu
        610                 615                 620

Phe Ala Glu Trp Asp Asn Asn Glu Gly Tyr Gly Val Arg Val Gln Met
625                 630                 635                 640

Gln Ala Ile Lys Gly Thr Asn Lys Ala Tyr Lys Asp Asp Arg Glu Leu
                645                 650                 655

Ala Ala Phe Ala Thr Thr Gln Asp Glu Ala Phe Gln Asn Ala Val Lys
                660                 665                 670

Asn Asp Ala Asn Ser Ala Ala Gln Ile Lys Gly Tyr Thr Thr Met Asp
            675                 680                 685

Val Leu Ala His Phe Pro Ala Trp Lys Gly Arg Val Asp Phe Gly Val
        690                 695                 700

Tyr Asn Val Trp Asn Arg Gln Tyr Arg Thr Val Phe Ala Gln Gln Ala
705                 710                 715                 720
```

-continued

```
Ala Val Ser Asn Ala Asn Pro Leu Leu Ala Ile Pro Ala Glu Gly Arg
            725                 730                 735

Thr Tyr Gly Leu Ser Tyr Thr Phe Asn Tyr
        740                 745

<210> SEQ ID NO 48
<211> LENGTH: 476
<212> TYPE: PRT
<213> ORGANISM: Acinetobacter baumannii

<400> SEQUENCE: 48

Met Gly Ala Gln Leu Val Arg Glu Val Ser Lys Thr Asn Asp Ile
1               5                   10                  15

Ala Gly Asp Gly Thr Thr Thr Ala Thr Val Leu Ala Gln Ala Ile Leu
            20                  25                  30

Asn Glu Gly Ile Lys Ser Val Thr Ala Gly Met Asn Pro Met Asp Leu
        35                  40                  45

Lys Arg Gly Ile Asp Ile Ala Val Lys Thr Val Glu Asn Ile Arg
50                  55                  60

Ser Ile Ala Lys Pro Ala Asp Asp Phe Lys Ala Ile Glu Gln Val Gly
65                  70                  75                  80

Ser Ile Ser Ala Asn Ser Asp Thr Thr Val Gly Lys Leu Ile Ala Gln
            85                  90                  95

Ala Met Glu Lys Val Gly Lys Glu Gly Val Ile Thr Val Glu Glu Gly
            100                 105                 110

Ser Gly Phe Glu Asp Ala Leu Asp Val Val Glu Gly Met Gln Phe Asp
        115                 120                 125

Arg Gly Tyr Ile Ser Pro Tyr Phe Ala Asn Lys Gln Asp Thr Leu Thr
    130                 135                 140

Ala Glu Leu Glu Asn Pro Phe Ile Leu Leu Val Asp Lys Lys Ile Ser
145                 150                 155                 160

Asn Ile Arg Glu Leu Ile Ser Val Leu Glu Ala Val Ala Lys Thr Gly
                165                 170                 175

Lys Pro Leu Leu Ile Ile Ala Glu Asp Val Glu Gly Glu Ala Leu Ala
            180                 185                 190

Thr Leu Val Val Asn Asn Met Arg Gly Ile Ile Lys Val Cys Ala Val
        195                 200                 205

Lys Ala Pro Gly Phe Gly Asp Arg Arg Lys Ala Met Leu Gln Asp Ile
    210                 215                 220

Ala Ile Leu Thr Gly Ala Thr Val Ile Ser Glu Glu Val Gly Met Ser
225                 230                 235                 240

Leu Glu Gln Ala Thr Leu Gln Asp Leu Gly Thr Ala His Lys Ile Thr
                245                 250                 255

Val Ser Lys Glu Asn Thr Val Ile Val Asp Gly Ala Gly Asp Ala Ala
            260                 265                 270

Ala Ile Ala Glu Arg Val Gln Gln Ile Arg Ala Gln Ile Glu Glu Ser
        275                 280                 285

Thr Ser Glu Tyr Asp Arg Glu Lys Leu Gln Glu Arg Val Ala Lys Leu
    290                 295                 300

Ala Gly Gly Val Ala Val Ile Lys Ile Gly Ala Ala Thr Glu Val Glu
305                 310                 315                 320

Met Lys Glu Lys Lys Asp Arg Val Asp Asp Ala Leu His Ala Thr Arg
                325                 330                 335

Ala Ala Val Glu Glu Gly Val Val Ala Gly Gly Gly Val Ala Leu Val
```

```
            340                 345                 350
Arg Ala Val Asn Ala Leu Glu Gly Leu Lys Gly Ala Asn Glu Asp Gln
            355                 360                 365

Thr Ala Gly Ile Asn Ile Leu Arg Arg Ala Ile Glu Ala Pro Leu Arg
        370                 375                 380

Gln Ile Val Ala Asn Ala Gly Asp Glu Pro Ser Val Val Ile Asn Ala
385                 390                 395                 400

Val Lys Asn Gly Glu Gly Asn Phe Gly Tyr Asn Ala Ala Thr Gly Glu
                405                 410                 415

Tyr Gly Asp Met Leu Glu Met Gly Ile Leu Asp Pro Ala Lys Val Thr
            420                 425                 430

Arg Ser Ala Leu Glu His Ala Ala Ser Val Ala Gly Leu Met Leu Thr
        435                 440                 445

Thr Glu Cys Met Ile Thr Asp Ile Pro Glu Asp Lys Pro Ala Ala Pro
    450                 455                 460

Asp Met Gly Gly Met Gly Gly Met Gly Gly Met Met
465                 470                 475

<210> SEQ ID NO 49
<211> LENGTH: 472
<212> TYPE: PRT
<213> ORGANISM: Acinetobacter baumannii

<400> SEQUENCE: 49

Met Ser Ala Phe Phe Gln Pro Gly Asn Tyr Phe Glu Ala Gly Ile Ser
1               5                   10                  15

Val Leu Asp Pro Asp Val Ala Gly Lys Glu Ala Gly Ser Ser Ala Thr
            20                  25                  30

Arg Arg Asp Ile Gly Asp Met Ala Asn Asp Tyr Tyr Phe Pro Ser Ala
        35                  40                  45

Ala Leu Lys Leu Gln Ile Asn Asp Gln Phe Ser Phe Gly Leu Leu Tyr
    50                  55                  60

Asp Gln Pro Phe Gly Ala Asp Ala Glu Tyr Ser Gly Asn Asn Val Phe
65                  70                  75                  80

Val Ser Asn Pro Gly Ser Asp Thr Ile Leu Ser Gln Lys Ala Leu Gly
                85                  90                  95

Asp Leu Ala Thr Ser Ser Ile Gln Lys Leu Val Gln Ala Ser Gly Ser
            100                 105                 110

Ala Phe Thr Pro Ala Leu Ile Glu Val Thr Lys Val Thr Gly Gly Asp
        115                 120                 125

Pro Thr Lys Pro Thr Gln Thr Glu Ile Leu Gly Ala Leu Gln Gln Val
    130                 135                 140

Ala Ala Gly Gly Asn Thr Thr Val Gly Ala Gly Leu Thr Ala Leu Gln
145                 150                 155                 160

Lys Thr Gln Ala Ala Ile Asn Ala Ala Asn Asn Tyr Leu Gly Thr Gly
                165                 170                 175

Gly Thr Lys Val Lys Val Asp Thr Gln Asn Leu Ser Phe Val Phe Gly
            180                 185                 190

Tyr Gln Pro Thr Lys Asn Phe Asn Phe Tyr Ala Gly Pro Val Leu Gln
        195                 200                 205

Thr Val Lys Gly Asn Val Ser Leu Arg Gly Gln Ala Tyr Ser Leu Tyr
    210                 215                 220

Asn Gly Tyr Asp Ala Asn Ile Lys Glu Thr Thr Gly Ala Gly Trp Leu
225                 230                 235                 240
```

```
Ala Gly Ala Ala Tyr Gln Ile Pro Glu Ile Ala Leu Arg Ala Ser Val
                245                 250                 255

Thr Tyr Arg Ser Glu Ile Asp His Lys Val Asn Ile Asp Glu Asn Leu
    260                 265                 270

Ser Ile Leu Asn Phe Pro Gly Leu Thr Ser Val Leu Ala Gly Leu Asp
            275                 280                 285

Val Pro Ala Ser Lys Leu Gln Ala Ile Asn Ser Ser Gly Lys Thr Thr
290                 295                 300

Ile Thr Thr Pro Gln Ser Val Asn Leu Asp Phe Gln Thr Gly Ile Met
305                 310                 315                 320

Ala Asp Thr Val Ala Phe Ala Asn Val Arg Trp Val Asn Trp Lys Asp
                325                 330                 335

Phe Ser Ile Gln Pro Tyr Lys Phe Gly Lys Val Ser Glu Ala Val Gly
                340                 345                 350

Gly Leu Ile Gly Arg Pro Asn Gly Phe Asn Leu Val Glu Tyr Ser Asp
            355                 360                 365

Asp Gln Trp Ser Val Asn Ala Gly Val Gly Arg Lys Leu Asn Asp Lys
370                 375                 380

Trp Ala Gly Asn Val Ser Val Gly Trp Asp Ser Gly Ala Gly Asn Pro
385                 390                 395                 400

Val Thr Thr Leu Gly Pro Thr Glu Gly Tyr Trp Asn Val Gly Leu Gly
                405                 410                 415

Val Gln Tyr Ser Pro Thr Pro Gln Thr Phe Ile Ala Gly Gly Val Lys
                420                 425                 430

Tyr Phe Trp Leu Gly Asp Ala Lys Ala Gln Thr Gly Ala Gln Ala Gly
            435                 440                 445

Ser Asp Glu Tyr Val Ala Asp Phe Ser Asp Asn Asn Ala Ile Ala Tyr
450                 455                 460

Gly Leu Lys Leu Gly Tyr Lys Phe
465                 470

<210> SEQ ID NO 50
<211> LENGTH: 216
<212> TYPE: PRT
<213> ORGANISM: Acinetobacter baumannii

<400> SEQUENCE: 50

Met Val Phe Ala Gln Asp Asp Asn Ala Leu His Tyr Asn Ile Val Asn
1               5                   10                  15

Val Gln Ala Glu Ala Ser Arg Gln Val Ser Asn Asp Glu Met His Ala
                20                  25                  30

Thr Leu Tyr Ile Glu Lys Ser Asn Lys Gln Pro Ala Glu Leu Ser Asn
            35                  40                  45

Gln Ile Asn Gln Leu Met Asn Gln Ala Leu Ala Thr Ser Arg Lys Tyr
        50                  55                  60

Pro Gln Val Lys Val Glu Thr Gly Ala Gln Ser Thr Tyr Pro Ile Tyr
65                  70                  75                  80

Asp Asn Asp Ser Asn Lys Leu Lys Glu Trp Arg Gly Arg Ala Glu Ile
                85                  90                  95

Arg Leu Glu Ser Lys Asp Phe Lys Ala Ala Ser Gln Leu Ile Asn Glu
            100                 105                 110

Leu Gln Gln Ser Phe Gln Thr Gln Ser Ile Asn Phe Ser Val Ser Asp
        115                 120                 125

Glu Gln Arg Lys Lys Val Glu Asn Glu Leu Met Val Glu Ala Ser Lys
    130                 135                 140
```

```
Asn Phe Gln Gln Arg Ala Gln Met Leu Thr Gln Ala Trp Asn Lys Ser
145                 150                 155                 160

Gln Tyr Ser Leu Val Thr Leu Asn Leu Asn Thr Asn Asn Tyr Phe Pro
            165                 170                 175

Gln Pro Val Met Arg Ala Ser Leu Ala Lys Phe Ala Ala Glu Ala
        180                 185                 190

Ala Pro Ala Gln Asp Met Ala Ala Gly Glu Ser Lys Ile Thr Val Asn
        195                 200                 205

Ala Asn Gly Ser Ile Gln Phe Lys
        210                 215
```

<210> SEQ ID NO 51
<211> LENGTH: 366
<212> TYPE: PRT
<213> ORGANISM: Acinetobacter baumannii

<400> SEQUENCE: 51

```
Met Lys Tyr Cys Gln Phe Phe Ser Val Leu Ala Leu Ser Leu Ser Ala
1               5                   10                  15

Ala Ser Cys Ala Val Thr Ser Gly Leu Gln Thr Tyr Asp Ile Pro Ser
            20                  25                  30

Glu Gly Val Tyr Lys Thr Asp Leu Gly Thr Thr Val Asn Val Val Lys
        35                  40                  45

Ile Ser Gln Glu Thr Leu Pro Ala Ile Gln Pro Ala Gln Ile Asp Tyr
50                  55                  60

Gln Arg Asp Tyr Ala Ser Leu Phe Lys Asn Gln Gln Ser Ile Tyr Arg
65                  70                  75                  80

Leu Ser Pro Gly Asp Val Leu Ser Ile Gln Leu Trp Ala Tyr Pro Glu
                85                  90                  95

Ile Thr Pro Pro Val Asn Asn Ile Ser Asn Glu Gln Ser Ile Gln Ala
            100                 105                 110

Asn Gly Tyr Pro Ile Asp Gln Ser Gly Tyr Ile Gln Phe Pro Leu Val
        115                 120                 125

Gly Arg Tyr Lys Ala Ala Gly Lys Thr Leu Ala Gln Val Asn Arg Glu
130                 135                 140

Leu His Ser Gln Leu Ala Arg Phe Leu Lys Asn Pro Asp Val Val Val
145                 150                 155                 160

Arg Val Val Ser Tyr Glu Gly Gln Arg Phe Ser Val Gln Gly Ser Val
                165                 170                 175

Thr Lys Gly Gly Gln Phe Tyr Leu Ser Asp Gln Pro Val Ser Ile Tyr
            180                 185                 190

Thr Ala Leu Gly Met Ala Gly Gly Val Thr Thr Thr Gly Asp Asn Thr
        195                 200                 205

Tyr Ile Gln Leu Ile Arg Asn Gly Arg Thr Tyr Asn Leu Asn Thr Ile
210                 215                 220

Asp Leu Glu Lys Ala Gly Tyr Ser Leu His Lys Leu Leu Val Gln Pro
225                 230                 235                 240

Asn Asp Thr Ile Tyr Val Ser Thr Arg Glu Asn Gln Lys Ile Tyr Val
                245                 250                 255

Met Gly Glu Ser Gly Lys Asn Gln Ala Leu Pro Met Arg Asp Gln Gly
            260                 265                 270

Met Thr Leu Ser Asp Ala Leu Gly Glu Ser Leu Gly Ile Asn Pro Asn
        275                 280                 285

Ser Ala Ser Ala Ser Arg Ile Tyr Val Val Arg Thr Asn Pro Asn Asp
```

```
                290                 295                 300
Arg Thr Thr Glu Ile Tyr His Leu Asn Leu Met Ser Leu Gly Asp Phe
305                 310                 315                 320

Gly Leu Ala Asn Gln Phe Arg Leu Arg Ser Asn Asp Ile Val Tyr Ile
                325                 330                 335

Asp Ala Thr Gly Leu Thr Arg Trp Gln Arg Val Val Asn Gln Ile Ile
                340                 345                 350

Pro Phe Ser Asn Ala Leu Tyr Asn Ile Asp Arg Leu Gly Gln
                355                 360                 365
```

<210> SEQ ID NO 52
<211> LENGTH: 208
<212> TYPE: PRT
<213> ORGANISM: Acinetobacter baumannii

<400> SEQUENCE: 52

```
Met Leu Asp Arg His Val Leu Arg Pro Val Ala Val Glu Tyr Arg Glu
1               5                   10                  15

Lys Thr Pro Glu Asp Val Arg Gly Ser Tyr Arg Gln Phe Arg Lys Asn
                20                  25                  30

Leu Gly Glu Pro Trp Asn Ala Val Asn Gln Leu Ile Gln Gly Arg Pro
            35                  40                  45

Gly Arg Ala Ala Lys Thr Leu Gly Arg Phe Thr Ile Asn Thr Leu Thr
50                  55                  60

Thr Leu Gly Leu Ala Asp Pro Ala Ser Arg Leu Gly Leu Pro Pro Glu
65                  70                  75                  80

Glu Glu Ser Phe Gly Val Thr Leu Gly Tyr Tyr Gly Val Pro Ser Gly
                85                  90                  95

Pro Phe Leu Met Leu Pro Phe Phe Gly Pro Ser Thr Leu Arg Asp Gly
                100                 105                 110

Val Gly Leu Ala Val Asp Ala Gln Ala Arg Pro Gln Lys Tyr Ile Met
            115                 120                 125

Asp Asp Gln Asp Gly Leu Tyr Trp Ser Thr Asn Leu Leu Gln Ala Val
130                 135                 140

Asp Thr Arg Ala Gln Tyr Leu Asp Leu Asp Gln Thr Ile Gln Gly Asp
145                 150                 155                 160

Gln Tyr Ala Met Ile Arg Asp Leu Tyr Leu Gln Arg Lys Ala Phe Gln
                165                 170                 175

Ile Ala Glu Lys Lys Gly Asp Ser Ala Asp Val Ser Phe Ile Asp Asp
                180                 185                 190

Asp Glu Ser Glu Asp Val Pro Glu Asp Asn Thr Asp Lys Thr Glu Lys
            195                 200                 205
```

<210> SEQ ID NO 53
<211> LENGTH: 326
<212> TYPE: PRT
<213> ORGANISM: Acinetobacter baumannii

<400> SEQUENCE: 53

```
Met Val Leu Leu Asn Ser Lys Gly Pro Val Gly Gln Gly Gln Ser Asp
1               5                   10                  15

Leu Met Met Thr Ala Ile Tyr Leu Met Leu Leu Val Val Ile Pro Ser
                20                  25                  30

Ile Ile Met Ala Leu Trp Phe Gly Trp Lys Tyr Arg Ala Ser Asn Lys
            35                  40                  45

Asp Ala Asp Tyr Lys Pro Thr Trp Ala His Ser Thr Ala Ile Glu Val
```

```
            50                  55                  60
Val Val Trp Gly Ile Pro Val Ile Ile Gly Ile Leu Ala Trp Leu
 65                  70                  75                  80

Thr Trp Trp Gly Ser His Lys Tyr Asp Pro Tyr Arg Pro Leu Glu Ser
                 85                  90                  95

Asp Lys Ala Pro Leu Thr Ile Gln Val Ile Ala Glu Gln Phe Lys Trp
                100                 105                 110

Ile Phe Ile Tyr Pro Glu Gln Asn Ile Ala Thr Val Asn Glu Val Arg
                115                 120                 125

Phe Pro Glu Lys Thr Pro Leu Ser Phe Lys Ile Thr Ser Asn Phe Thr
                130                 135                 140

Met Asn Ser Phe Phe Ile Pro Gln Leu Gly Gly Gln Ile Tyr Ala Met
145                 150                 155                 160

Ala Gly Met Gln Thr His Leu His Leu Leu Ala Asn Glu Thr Gly Val
                165                 170                 175

Tyr Arg Gly Phe Ser Ser Asn Tyr Ser Gly Tyr Gly Phe Ser Gln Met
                180                 185                 190

Arg Phe Lys Ala His Ser Val Thr Glu Gln Gln Phe Asn Glu Trp Val
                195                 200                 205

Ala Ala Val Lys Ala Gly Asn Gly Thr Thr Ile Asn Pro Glu Ala Val
                210                 215                 220

Gln Lys Thr Thr Leu Asp Gln Ala Glu Leu Ala Thr Leu Arg Asp Gly
225                 230                 235                 240

Asp Arg Ser Lys His Gln Ile Glu His Leu Val Asn Arg Ala Lys Ala
                245                 250                 255

Ala Gly Asp Gln Glu Ala Leu Ala Lys Ala Glu Ala Met Lys Pro Phe
                260                 265                 270

Pro Thr Lys Pro His Pro Val Thr Tyr Tyr Ser Ser Val Glu Pro Lys
                275                 280                 285

Leu Phe Glu Thr Ile Ile Asn His Tyr Met Ser Asn Tyr His Gly Ala
                290                 295                 300

Asp His Ser Ala Ala His Thr Ala Ala Glu Thr His Val Ala Ala Glu
305                 310                 315                 320

His Ala Ala Gln Gly Glu
                325

<210> SEQ ID NO 54
<211> LENGTH: 207
<212> TYPE: PRT
<213> ORGANISM: Acinetobacter baumannii

<400> SEQUENCE: 54

Met Ala Arg Tyr Ile Gly Pro Lys Cys Lys Leu Ser Arg Arg Glu Gly
 1               5                  10                  15

Thr Asp Leu Gln Leu Lys Ser Gly Val Lys Pro Phe Asp Val Lys Thr
                20                  25                  30

Lys Lys His Ala Lys Ala Pro Gly Gln His Gly Gln Ala Arg Gly Lys
                35                  40                  45

Gln Ser Glu Tyr Ser Leu Gln Leu Arg Glu Lys Gln Lys Val Arg Arg
                50                  55                  60

Met Tyr Gly Val Leu Glu Arg Gln Phe Ser Asn Tyr Tyr Lys Glu Ala
 65                  70                  75                  80

Ala Arg Val Lys Gly Ala Thr Gly Glu Asn Leu Leu Lys Leu Leu Glu
                85                  90                  95
```

```
Ser Arg Leu Asp Asn Val Val Tyr Arg Met Gly Phe Gly Ser Thr Arg
            100                 105                 110

Ala Glu Ala Arg Gln Leu Val Ser His Arg Ser Ile Thr Leu Asn Gly
        115                 120                 125

Arg Arg Val Asn Ile Ala Ser Ile Gln Val Lys Ala Gly Asp Val Ile
    130                 135                 140

Ala Val His Glu Gly Ala Lys Gln Gln Leu Arg Ile Lys Asn Ala Ile
145                 150                 155                 160

Glu Leu Ala Ala Gln Arg Gly Ile Pro Ala Trp Met Asp Val Asp His
                165                 170                 175

Ser Lys Leu Glu Gly Thr Phe Lys Ala Ala Pro Asp Arg Ser Asp Leu
            180                 185                 190

Pro Ala Glu Ile Asn Glu Ser Leu Ile Val Glu Leu Tyr Ser Lys
        195                 200                 205

<210> SEQ ID NO 55
<211> LENGTH: 355
<212> TYPE: PRT
<213> ORGANISM: Acinetobacter baumannii

<400> SEQUENCE: 55

Met Ala His Ala Glu Val Asn Ser Ser Thr Gln Gln Val Asn Gly
1               5                   10                  15

Leu Ser Ser Gly Ala Gln Ala Glu Glu Asn Lys Asp Glu Asn Leu Leu
            20                  25                  30

Asp Gln Ile Pro Arg Trp Ile Asp Ala Thr Pro Thr Ile Phe Pro Glu
        35                  40                  45

Gln Ser Asn Glu Pro Ile Val Pro Pro Thr Glu Gln Thr Glu Asp Gln
    50                  55                  60

Thr Trp Phe Asp Arg Lys Gln Lys Lys Ile Arg Asn Trp Ala Asp Arg
65                  70                  75                  80

Thr Ser Gly Lys Ile Asp Asn Trp Phe Gly Glu Val Asp Pro Gln Lys
                85                  90                  95

Pro Ala Ser Ala Thr Ile Arg Val Met Ile Asp Asn Tyr Trp Asn Glu
            100                 105                 110

Tyr Asp Asn Tyr Glu Ile Lys Pro Arg Ile Arg Gly Lys Ile Lys Leu
        115                 120                 125

Pro Thr Leu Glu Lys Arg Leu Ser Val Val Phe Gly Asp Asp Ser Leu
    130                 135                 140

Asp Asp Glu Phe Asn Asn Ser Pro Ala Asn Ile Asn Gln Asn Pro Asn
145                 150                 155                 160

Gln Asp Pro Asn Lys Lys Leu Asp Gly Lys Arg Thr Arg Asp Asp Asn
                165                 170                 175

Ser Ser Ile Ala Leu Arg Trp Ser Asn Phe Ser Lys Lys Leu Pro Phe
            180                 185                 190

Glu Thr Asp Ala Asp Leu Gly Ile Arg Ser Gly Asp Asp Ile Tyr Val
        195                 200                 205

Arg Leu Lys Ala Ser Arg Asp Trp Gln Leu Arg Asn Asp Phe Lys Phe
    210                 215                 220

Tyr Ala Glu Gln Ile Tyr Arg Tyr Gly Ile Asp Ser Glu Asn Tyr Leu
225                 230                 235                 240

Arg Thr Asn Leu Glu Leu Thr His Ala Arg Pro Asn Gln Pro Ile Leu
                245                 250                 255

Ser Asn Gln Phe Ser Leu Thr Tyr Ala Asp Asp Gln Asp Asp Leu
            260                 265                 270
```

```
Thr Trp Glu Asn Arg Leu Phe Arg Glu His Ser Phe Ala Asn Asn
        275                 280                 285

Arg Phe Asn Tyr Gly Ile Tyr Thr Gly Gly Tyr Tyr Asn Asp Asn Asp
    290                 295                 300

Leu Arg Leu Asn Ser Trp Gly Pro Phe Ser Trp Arg Gln Pro Val
305                 310                 315                 320

Leu Arg Glu Trp Phe Phe Val Gln Gly Asp Leu Asn Tyr Phe Asn Asp
                325                 330                 335

His Arg Glu Asp Arg Asn His Tyr Val Ser Thr Phe Leu Arg Leu Glu
            340                 345                 350

Ala Leu Phe
        355

<210> SEQ ID NO 56
<211> LENGTH: 108
<212> TYPE: PRT
<213> ORGANISM: Acinetobacter baumannii

<400> SEQUENCE: 56

Met Ser Thr Leu Leu Val Ala Cys Asn Lys His Glu Asn Lys Thr Glu
1               5                   10                  15

Thr Thr Ser Asp Ala Ser Thr Pro Val Gln Thr Ala Gln Ser Asn Asn
            20                  25                  30

Asn Glu Ala Val Asp Thr Ala His Thr Ala Glu Asn Ser Leu Asp Trp
        35                  40                  45

Asp Gly Lys Tyr Lys Gly Thr Leu Pro Cys Ala Asp Cys Glu Gly Ile
    50                  55                  60

Lys Thr Glu Leu Glu Leu Lys Asp Asp Lys Thr Tyr Glu Leu Thr Glu
65                  70                  75                  80

Thr Tyr Leu Gly Lys Gly Asp Ala Asn Pro Phe Glu Pro Met Val Ser
                85                  90                  95

Leu Leu Ser Ile Lys Thr Ile Leu Leu Leu Pro
            100                 105

<210> SEQ ID NO 57
<211> LENGTH: 635
<212> TYPE: PRT
<213> ORGANISM: Acinetobacter baumannii

<400> SEQUENCE: 57

Met Arg Gly Phe Gly Arg Ser Thr Phe Gly Val Arg Gly Ile Arg
1               5                   10                  15

Leu Tyr Val Asp Gly Ile Pro Ala Thr Met Pro Asp Gly Gln Gly Gln
            20                  25                  30

Thr Ser Asn Ile Asp Leu Ser Ser Leu Asp His Val Glu Val Leu Thr
        35                  40                  45

Gly Pro Phe Ser Ser Leu Tyr Gly Asn Ser Ser Gly Gly Thr Ile Leu
    50                  55                  60

Thr Ser Thr Lys Glu Gly Gln Gly Lys Asp Ser Ile Glu Leu Ser Tyr
65                  70                  75                  80

Ser Gly Gly Ser His Asp Lys Ser Arg Ala Gly Leu Val Leu Gln Gly
                85                  90                  95

Gly Ala Lys Gly Ala Asn Glu Pro Ser Tyr Ile Ile Ser Ser Ser Tyr
            100                 105                 110

Phe Asp Thr Asp Gly Tyr Arg Glu His Ser Gly Ala Glu Lys Val Leu
        115                 120                 125
```

```
Asn Asn Ala Lys Leu Ser Trp Asn Leu Asp Asp Gly Ser Lys Ile Asn
            130                 135                 140

Trp Val Thr Asn Tyr Val Lys Ile His Ala Asp Asp Pro Met Gly Leu
145                 150                 155                 160

Glu Arg Lys Asp Trp Gln Ala Asn Pro Lys Gln Ile Ala Pro Tyr Val
                165                 170                 175

Lys Lys Trp Gly Phe Asn Ala Arg Lys Asp Ile Glu Gln Thr Gln Thr
            180                 185                 190

Gly Ile Thr Trp Phe Lys Pro Ile Asn Asp Gln His Glu Leu Tyr Ala
            195                 200                 205

Met Ala Tyr Leu Gly Asn Arg Gln Val Thr Gln Tyr Gln Ser Ile Pro
210                 215                 220

Gln Gly Gln Val Val Glu Asn Gly Lys Pro Val Tyr Thr Gly Gln
225                 230                 235                 240

Lys Ser Pro Lys His Ala Gly Gly Val Ile Asp Phe Glu Arg Asn Tyr
                245                 250                 255

Tyr Gly Ala Asp Phe Arg Trp Thr Gly Lys Glu Leu Leu Pro Asn Thr
                260                 265                 270

Thr Val Ser Ile Gly Val Ala Phe Asp Ala Met Asp Glu Glu Arg Lys
            275                 280                 285

Gly Phe Glu Asn Phe Asn Ala Asp Gly Ile Tyr Gly Val Lys Gly Asn
290                 295                 300

Leu Arg Arg Asp Glu Asp Asn Thr Leu Trp Asn Ile Asp Pro Tyr Leu
305                 310                 315                 320

Gln Ala Ser Trp Gln Phe Leu Pro Thr Trp Arg Leu Asp Thr Gly Val
                325                 330                 335

Arg Tyr Ser Asn Val His Tyr Lys Ser Lys Asp His Phe Thr Ser Gly
            340                 345                 350

Pro Asp Glu Tyr Gly Thr Val Asn Gly Asp Asp Ser Gly Lys Thr Asp
            355                 360                 365

Tyr Glu Lys Val Leu Pro Ser Ala Leu Ser Trp Gln Ile Leu Pro
370                 375                 380

Glu Leu Met Ala Tyr Val Ser Tyr Ala Lys Gly Phe Glu Thr Pro Thr
385                 390                 395                 400

Phe Thr Glu Met Ala Tyr His Thr Asp Ile Ser Lys Ser Gly Phe Asn
                405                 410                 415

Phe Gly Leu Lys Pro Ser Thr Ser Asp Thr Tyr Glu Thr Gly Leu Lys
            420                 425                 430

Ser Gln Asn Leu Leu Gly Asp Phe Thr Leu Ala Val Phe Gln Thr Lys
            435                 440                 445

Thr Lys Asn Asp Ile Val Ser Ala Gly Asn Leu Gly Gly Arg Ser Thr
450                 455                 460

Phe Arg Asn Ala Asp Lys Thr Leu Arg Glu Gly Val Glu Phe Ala Trp
465                 470                 475                 480

Asn Lys Lys Leu Trp Arg Asp Leu Thr Ala Thr Ala Ser Tyr Thr Tyr
                485                 490                 495

Leu Asp Ala Thr Phe Asp Ala Asn Val Pro Glu Lys Leu Asp Gln Asp
            500                 505                 510

Asn Lys Val Leu Ala Ser Ala Ile Pro Thr Gly Asn Ala Ile Pro Gly
            515                 520                 525

Ile Ala Lys Asn Gln Ala Tyr Ala Ser Leu Ala Trp Gln Pro Ser His
530                 535                 540
```

```
Gly Leu Tyr Gly Gly Val Asp Val Gln Tyr Met Asp Lys Val Tyr Val
545                 550                 555                 560

Asn Asp Thr Asn Ser Asp Ala Ala Pro Ser Tyr Ser Val Thr Ser Ala
                565                 570                 575

Asn Val Gly Tyr Ala Trp Val Met Gly Asp Trp Lys Val Asn Ser Phe
                580                 585                 590

Ala Arg Val Asp Asn Leu Phe Asp Lys Lys Tyr Ala Gly Ser Val Ile
            595                 600                 605

Val Asn Asp Gly Asn Ser Arg Tyr Phe Glu Pro Ala Asp Gly Arg Asn
            610                 615                 620

Trp Ser Ala Gly Leu Arg Val Ile Lys Gln Phe
625                 630                 635

<210> SEQ ID NO 58
<211> LENGTH: 381
<212> TYPE: PRT
<213> ORGANISM: Acinetobacter baumannii

<400> SEQUENCE: 58

Met Thr Gly Ile Ser Ser Val Tyr Ala Gln Glu Gln Val Asp Pro Ala
1               5                   10                  15

Tyr Lys Pro Gly Asn Pro Ile Tyr Asp Lys Trp Asp Arg Phe Tyr Lys
                20                  25                  30

Ile Glu Gln Ser Gln Pro Gln Glu Ala Glu Lys Ile Leu Val Glu Leu
            35                  40                  45

Ser Lys Leu Thr Pro Thr Asp Ile Lys Val Trp Lys Ser Leu Thr Tyr
    50                  55                  60

Leu Gln Ile Arg Leu Glu Lys Arg Glu Glu Ala Leu Gln Ser Leu Arg
65                  70                  75                  80

Gln Ala Arg Asn Leu Ala Pro Gln Asp Asp Thr Leu Lys Leu Gln Glu
                85                  90                  95

Ala Tyr Leu Leu Asn Gln Gln Lys Lys Asp Arg Glu Ala Leu Val Leu
            100                 105                 110

Phe Lys Glu Leu Ser Ser Ser Asp Pro Glu Ile Ala Ala Lys Ala
            115                 120                 125

Thr Gln Ala Val Lys Asn Leu Ser Gly Gly Glu Val Lys Pro Tyr Phe
    130                 135                 140

Lys Asp Ile Tyr Phe Ala Pro Ser Tyr Glu Ser Arg Tyr Asp Asp Val
145                 150                 155                 160

Ile Phe Pro Leu Lys Met Arg Tyr Gly Lys Asn Ile Asp Asn Gly Arg
                165                 170                 175

Ala Gln Val Tyr Ala Phe Leu Asn Leu Asn Arg Asp Thr Gln Ser Gln
            180                 185                 190

Gly Gly Val Arg Pro Glu Ile Ile Asp Glu Asn Ala Ala Thr Leu Gly
            195                 200                 205

Leu Gly Ala Asn Tyr Gln Pro Trp Thr Ser Ile Pro Val Arg Ala Tyr
    210                 215                 220

Val Glu Val Gly Gly Ser Tyr Asp Leu Ile Asp Arg Asn Arg Lys Arg
225                 230                 235                 240

Phe Arg Glu Ser Val Val Gly Gly Val Thr Gly Tyr Gln Glu Trp Tyr
                245                 250                 255

Ser Gln Ser Asn Cys Asp His Ser Leu Cys Leu Asp Asn Tyr Phe Thr
            260                 265                 270

Asp Leu Tyr Gly Asn Val Ala Thr Tyr Ser Arg Glu Asp Tyr Asn Val
            275                 280                 285
```

Ile Gly Asp Leu Arg Leu Arg Thr Gly Leu Asn Leu Tyr Lys Gly Glu
    290                 295                 300

Ser Gly Thr Val Gln Ala Tyr Val Lys Leu His Gly Leu Ala Asp Ser
305                 310                 315                 320

Glu Asp Glu Tyr Tyr Asn Asn Leu Phe Glu Tyr Gly Pro Gly Ile Ser
                325                 330                 335

Trp Gln Pro Phe Asn Tyr Gln Pro Ile Lys Leu Arg Val Glu Arg Leu
            340                 345                 350

Tyr Gly Asn Tyr Phe Lys Asp Val Pro Val Asn Thr Lys Asp His Tyr
        355                 360                 365

Asn Asn Thr Arg Val Glu Leu Val Phe Tyr Lys Asp Phe
    370                 375                 380

<210> SEQ ID NO 59
<211> LENGTH: 212
<212> TYPE: PRT
<213> ORGANISM: Acinetobacter baumannii

<400> SEQUENCE: 59

Met Ala Ile Gly Leu Val Gly Arg Lys Cys Gly Met Thr Arg Ile Phe
1               5                   10                  15

Thr Asp Ala Gly Val Ser Val Pro Val Thr Val Ile Glu Val Asp Pro
            20                  25                  30

Asn Arg Ile Thr Gln Ile Lys Thr Leu Glu Thr Asp Gly Tyr Gln Ala
        35                  40                  45

Val Gln Val Thr Thr Gly Glu Arg Arg Glu Ser Arg Val Thr Asn Ala
    50                  55                  60

Gln Lys Gly His Phe Ala Lys Ala Gly Val Ala Ala Gly Arg Leu Val
65                  70                  75                  80

Lys Glu Phe Arg Val Thr Glu Ala Glu Leu Glu Gly Arg Glu Ile Gly
                85                  90                  95

Gly Thr Ile Gly Val Asp Leu Phe Thr Val Gly Gln Val Val Asp Val
            100                 105                 110

Thr Gly Gln Ser Lys Gly Lys Gly Phe Gln Gly Gly Val Lys Arg Trp
        115                 120                 125

Asn Phe Arg Thr Gln Asp Ala Thr His Gly Asn Ser Val Ser His Arg
    130                 135                 140

Val Leu Gly Ser Thr Gly Gln Asn Gln Thr Pro Gly Arg Val Phe Lys
145                 150                 155                 160

Gly Lys Lys Met Ala Gly His Leu Gly Asp Glu Arg Val Thr Val Gln
                165                 170                 175

Gly Leu Glu Ile Val Ser Ile Asp Ala Glu Arg Ser Val Leu Val Val
            180                 185                 190

Lys Gly Ala Ile Pro Gly Ala Thr Gly Gly Asp Val Ile Val Arg Pro
        195                 200                 205

Thr Ile Lys Ala
    210

<210> SEQ ID NO 60
<211> LENGTH: 424
<212> TYPE: PRT
<213> ORGANISM: Acinetobacter baumannii

<400> SEQUENCE: 60

Met Leu Lys Ala Gln Lys Leu Thr Leu Ala Val Leu Ile Ser Ala Ala
1               5                   10                  15

```
Ile Ile Ser Ser Ala Gln Ala Ser Glu Gln Ser Glu Ala Lys Gly Phe
            20                  25                  30

Val Glu Asp Ala Asn Gly Ser Ile Leu Phe Arg Thr Gly Tyr Ile Ser
        35                  40                  45

Arg Asp Lys Lys Asp Gly Arg Ala Asp Asn Ser Ser Phe Ala Gln Thr
    50                  55                  60

Ala Ile Val Asn Ile Asp Ser Gly Phe Thr Pro Gly Ile Val Gly Phe
65                  70                  75                  80

Gly Val Gly Val Val Gly Asp Gly Ser Phe Lys Ile Gly Glu Asn Lys
                85                  90                  95

Asn Ala Gly Asn Asn Met Ile Pro Gln His Asn Asp Gly Ser Ala Tyr
            100                 105                 110

Asp His Trp Ala Arg Gly Gly Ala Asn Val Lys Ala Arg Phe Ser Asn
        115                 120                 125

Thr Thr Val Arg Tyr Gly Thr Gln Val Leu Asp Leu Pro Val Leu Ala
    130                 135                 140

Ser Asn Thr Ala Arg Leu Val Pro Glu Tyr Phe Thr Gly Thr Leu Leu
145                 150                 155                 160

Thr Ser His Glu Ile Lys Asp Leu Glu Val Val Ala Gly Lys Phe Thr
                165                 170                 175

Lys Asn Gln Tyr Ser Asp Gln Ile Ala Thr Asp Gln Asn Gly Leu Asp
            180                 185                 190

Arg Ala Val Val Trp Gly Ala Lys Tyr Lys Phe Asp Asp Gln Ile Ser
        195                 200                 205

Gly Ser Tyr Tyr Gly Val Asp Val Lys Asp Lys Leu Asp Arg His Tyr
    210                 215                 220

Val Asn Val Asn Tyr Lys Gln Pro Leu Ala Asn Asp Ser Ser Leu Thr
225                 230                 235                 240

Tyr Asp Phe Ser Gly Tyr His Thr Lys Phe Asp Lys Gly Ala Asn Leu
                245                 250                 255

Ser Tyr Ala Thr Gly Pro Ala Asp Glu Asp Lys Thr Asn Asn Ile Trp
            260                 265                 270

Ala Ile Ser Gly Thr Tyr Ala Thr Gly Pro His Ser Val Met Leu Ala
        275                 280                 285

Tyr Gln Gln Asn Ser Gly Asn Ile Gly Tyr Asn Tyr Gly Val Asn Gln
    290                 295                 300

Asp Gly Gly Gln Ser Val Tyr Leu Pro Asn Ser Tyr Leu Ser Asp Phe
305                 310                 315                 320

Ile Gly Asn Asp Glu Lys Ser Ala Gln Ile Gln Tyr Ser Leu Asp Phe
                325                 330                 335

Gly Lys Leu Gly Val Leu Pro Gly Leu Asn Trp Thr Thr Ala Tyr Val
            340                 345                 350

Tyr Gly Trp Asp Ile Lys Thr Ser Asn Gly Ala Asp Asp Ser Asn Glu
        355                 360                 365

Ser Glu Phe Phe Asn Gln Val Lys Tyr Thr Val Gln Ser Gly Phe Ala
    370                 375                 380

Lys Gly Ser Ser Leu Arg Leu Arg Asn Ser Ile Tyr Arg Ala Asp Asn
385                 390                 395                 400

Ala Tyr Thr Thr Asp Tyr Met Pro Asp Thr Asn Glu Trp Arg Ile Phe
                405                 410                 415

Leu Asp Ile Pro Val Thr Leu Phe
            420
```

<210> SEQ ID NO 61
<211> LENGTH: 641
<212> TYPE: PRT
<213> ORGANISM: Acinetobacter baumannii

<400> SEQUENCE: 61

```
Met Gln Leu Lys Asp Val Pro Gln Ile Val Asn Val Pro Lys Gln
1               5                   10                  15

Val Leu Arg Glu Gln Thr Val Thr Ser Met Gln Gly Ala Leu Gln Asn
            20                  25                  30

Val Ala Gly Leu Ser Phe Ser Val Gly Asp Gly Gln Arg Asp Gln Val
        35                  40                  45

Met Ile Arg Gly Phe Ser Ala Ile Thr Asp Asn Tyr Val Asp Gly Ile
    50                  55                  60

Arg Asp Asp Ala Leu Tyr Phe Arg Asp Met Ser Asn Val Glu Arg Ile
65                  70                  75                  80

Glu Val Leu Lys Gly Pro Ala Ser Val Leu Tyr Gly Arg Gly Ser Ala
                85                  90                  95

Gly Gly Leu Val Asn Lys Ile Asn Lys Lys Pro Met Asp Gln Ser Leu
            100                 105                 110

Arg Glu Val Ser Leu Ile Gly Ser Thr Thr Gly Gln Arg Arg Ala Glu
        115                 120                 125

Val Asp Val Asn Glu Lys Val Ala Glu Asn Val Lys Val Arg Leu Thr
    130                 135                 140

Gly Ala Val Glu Asp Ser Asp Gly Tyr Arg Asp Gln Ala Phe Leu Lys
145                 150                 155                 160

Arg Gln Ala Val Ala Pro Ser Val Gln Trp Asp Ile Thr Asp Lys Thr
                165                 170                 175

Lys Leu Leu Leu Gln Ala Asp Tyr Leu His Asp Asn Arg Leu Ala Asp
            180                 185                 190

Gln Gly Phe Pro Thr Asp Pro Ile Thr Gly Lys Pro Val Lys Thr Asn
        195                 200                 205

Pro Lys Thr Phe Tyr Gly Ala Leu Asn Gly Lys Glu Val Gly Asp Val
    210                 215                 220

Asp Thr Glu Ile Ser Ser Gln Thr Ile Ser Leu Asp His Glu Phe Asn
225                 230                 235                 240

Asp Asn Phe Lys Tyr His Gly Ala Val Arg His Tyr Asn Tyr Ser Leu
                245                 250                 255

Asp Arg Gln Tyr Ser Val Asp Ser His Gln Lys Leu Pro Ala Asp Gln
            260                 265                 270

Ile Gln Leu Thr Gln Asn Lys Arg Leu Arg Asn Glu Asp Gly Val Tyr
        275                 280                 285

Val Gln Gln Glu Leu Ser Ala Val Phe Asn Thr Gly Phe Leu Lys His
    290                 295                 300

Ser Thr Leu Ile Gly Ala Glu Tyr Ser Lys Gln His Lys Asp Glu Leu
305                 310                 315                 320

Val Trp Ser Lys Ala Arg Gln Ile Thr Asn Ile Phe Asn Pro Gln Leu
                325                 330                 335

Glu Asn Trp Ala Pro Leu Asp Thr Asn Val Asp Ala Asp Thr Asn Asn
            340                 345                 350

Thr Asn Thr Phe Glu Asn Tyr Gly Val Tyr Leu Gln Asp Leu Met Thr
        355                 360                 365

Val Thr Asp Gln Leu Lys Val Leu Val Gly Leu Arg Tyr Asp Asn Leu
    370                 375                 380
```

Ser Gln Asp Arg Asp Asp Lys Thr Ser Lys Asn Val Asp Leu Asn Arg
385                 390                 395                 400

Thr Asp Asn Thr Tyr Ser Pro Arg Ile Gly Val Val Tyr Gln Pro Val
            405                 410                 415

Asn Asn Leu Ser Leu Tyr Thr Ser Tyr Asn Arg Ser Phe Gln Pro Leu
            420                 425                 430

Ala Asp Ser Phe Val Phe Tyr Lys Asn Ser Asp Asp Leu Arg Pro Thr
            435                 440                 445

Lys Thr Glu Asn Tyr Glu Ile Gly Ala Lys Trp Asp Val Asn Asp Gln
            450                 455                 460

Leu Asn Val Thr Leu Ala Leu Phe Glu Met Ser Gln Thr Asn Ile Gln
465                 470                 475                 480

Asn Lys Asp Pro Asn Asp Pro Lys Gly Leu Thr Ala Ile Leu Ala Gly
            485                 490                 495

Glu Gln Lys Thr Lys Gly Val Glu Ile Ser Leu Ala Gly Gln Leu Thr
            500                 505                 510

Asp Gln Leu Ser Val Leu Ala Gly Tyr Ser Tyr Met Asp Gly Lys Ile
            515                 520                 525

Glu Lys Ser Ala Ile Gly Phe Thr Gly Asn His Ser Ala Leu Thr Pro
            530                 535                 540

Asn Asn Thr Ala Asn Leu Trp Leu Lys Tyr Gln Ile Asn Asp His Trp
545                 550                 555                 560

Tyr Ala Ala Val Gly Gly Arg Gly Glu Ser Ser Arg Phe Ser Ala Pro
            565                 570                 575

Asp Asn Lys Asn Val Leu Pro Gly Tyr Ala Val Val Asn Ala Ala Leu
            580                 585                 590

Gly Tyr Gln Ser Glu Arg Tyr Asp Val Asn Leu Asn Leu Asn Asn Leu
            595                 600                 605

Phe Asp Arg Asp Tyr Phe Val Ser Gly His Ser Gly Ala Asn Asp Ser
            610                 615                 620

Asn Met Met Gly Asp Pro Leu Asn Ala Gln Val Ala Leu Arg Tyr Arg
625                 630                 635                 640

Phe

<210> SEQ ID NO 62
<211> LENGTH: 209
<212> TYPE: PRT
<213> ORGANISM: Acinetobacter baumannii

<400> SEQUENCE: 62

Met Glu Glu Ala Val Gln Val Leu Asn Ser Leu Pro Ala Ala Lys Phe
1               5                   10                  15

Lys Glu Ser Leu Asp Ile Ser Val Asn Leu Gly Val Asp Pro Arg Lys
            20                  25                  30

Ser Asp Gln Val Val Arg Gly Ala Thr Thr Leu Pro Ala Gly Thr Gly
            35                  40                  45

Lys Thr Val Arg Val Ala Val Phe Ala Gln Gly Ala Gln Ala Glu Ala
    50                  55                  60

Ala Lys Glu Ala Gly Ala Asp Val Val Gly Phe Asp Asp Leu Ala Glu
65                  70                  75                  80

Ser Ile Gln Gly Gly Asn Leu Asp Phe Asp Val Val Ile Ala Ala Pro
            85                  90                  95

Asp Ala Met Arg Val Val Gly Lys Leu Gly Thr Ile Leu Gly Pro Arg
            100                 105                 110

```
Gly Leu Met Pro Asn Pro Lys Val Gly Thr Val Thr Pro Asp Val Ala
        115                 120                 125

Gly Ala Val Lys Asn Ala Lys Ser Gly Gln Ala Arg Tyr Arg Val Asp
        130                 135                 140

Lys Ala Gly Ile Ile His Ala Ile Gly Gln Val Gly Phe Asp Ala
145                 150                 155                 160

Ala Ala Ile Arg Gln Asn Val Glu Thr Leu Val Ala Asp Leu Lys Lys
                165                 170                 175

Leu Lys Pro Ala Thr Ser Lys Gly Val Tyr Ile Lys Lys Ile Thr Leu
        180                 185                 190

Ser Ser Thr Met Gly Pro Gly Leu Thr Val Asp Val Asn Asn Val Ser
        195                 200                 205

Asn
```

<210> SEQ ID NO 63
<211> LENGTH: 147
<212> TYPE: PRT
<213> ORGANISM: Acinetobacter baumannii

<400> SEQUENCE: 63

```
Met Tyr Pro Ala Pro Thr Val Asp Gln Leu Ala Ile Asp His Ala Pro
1               5                   10                  15

Lys Phe Glu Asn Lys Arg Gly Asn Arg Phe Ala Leu Pro Arg Pro Glu
            20                  25                  30

Pro Leu Gln Thr Asp Thr Thr Ala Asp Ala Ser Ala Gln Thr Gly Ser
        35                  40                  45

Ala Leu Gly Arg Pro Gln Leu Val Thr Asp Gly Asn Lys Asn Pro Leu
    50                  55                  60

Leu Lys Ile Asp Gly Ser Thr Ala Glu Ile Trp Gln Tyr Thr Lys Ala
65                  70                  75                  80

Thr Leu Ser Thr Leu Asn Tyr Asn Val Ile Ala Gln Gly Asn Asn Gln
                85                  90                  95

Ala Thr Ile Lys Val Asn Asp Asn Thr Tyr Val Leu Lys Leu Thr Gly
            100                 105                 110

Val Gly Ser Ser His Ser Leu Ala Leu Phe Asn Pro Asp Asn Thr Phe
        115                 120                 125

Ala Ser Pro Asp Val Ala Ala Glu Val Leu Asn Gln Ile Tyr Gln Asn
    130                 135                 140

Trp Pro Ala
145
```

<210> SEQ ID NO 64
<211> LENGTH: 201
<212> TYPE: PRT
<213> ORGANISM: Acinetobacter baumannii

<400> SEQUENCE: 64

```
Met Lys Val Ser Gly Leu Val Gly Thr Asn Leu Ser Asp Gly Tyr Thr
1               5                   10                  15

Met Lys Ala Gln Phe Asp Asn Val Asn Gly Leu Lys Pro Arg Ala Lys
            20                  25                  30

Val Thr Met Ser Gly Val Thr Ile Gly Arg Val Asp Ser Ile Thr Leu
        35                  40                  45

Asp Pro Val Thr Arg Leu Ala Thr Val Thr Phe Asp Leu Asp Gly Lys
    50                  55                  60
```

```
Leu Thr Ser Phe Asn Ala Glu Gln Leu Lys Glu Val Gln Lys Asn Ala
 65                  70                  75                  80

Leu Asp Glu Leu Arg Tyr Ser Asp Tyr Thr Gln Ala Thr Pro Ala
                 85                  90                  95

Gln Gln Lys Thr Met Glu Gln Leu Ile Ser Asn Met Asn Ser Ile
            100                 105                 110

Thr Ser Ile Asp Glu Asp Ala Tyr Ile Met Val Ala Thr Asn Gly Leu
        115                 120                 125

Leu Gly Glu Lys Tyr Leu Lys Ile Val Pro Gly Gly Leu Asn Tyr
    130                 135                 140

Leu Lys Arg Gly Asp Thr Ile Ser Asn Thr Gln Gly Thr Met Asp Leu
145                 150                 155                 160

Glu Asp Leu Ile Ser Lys Phe Ile Thr Gly Gly Ala Gly Lys Val
                165                 170                 175

Ala Ala Gly Ser Ser Ala Glu Glu Lys Ala Pro Ala Ser Thr Asp
            180                 185                 190

Ser Ser Ala Gln Pro Ser Phe Val Glu
            195                 200
```

<210> SEQ ID NO 65
<211> LENGTH: 183
<212> TYPE: PRT
<213> ORGANISM: Acinetobacter baumannii

<400> SEQUENCE: 65

```
Met Gly Val Ser Ser Phe Thr Phe Ala Gly Asn Trp Gln Val Lys Phe
  1               5                  10                  15

Gly Gly Ser Val Ile Ala Pro Ser Glu Asp Thr Thr Ala Leu Gly
             20                  25                  30

Val Val Lys Ala Asp His Glu Tyr Ala Phe Thr Pro Ser Val Glu Tyr
             35                  40                  45

Phe Phe Gly Gln Ser Pro Phe Ser Ala Glu Leu Leu Leu Ala Thr Pro
     50                  55                  60

Val Asn His Asp Val Leu Leu Asp Gly Gln Lys Val Ala Arg Ile Lys
 65                  70                  75                  80

Gln Leu Pro Pro Thr Ile Thr Ala Lys Tyr His Phe Lys Asn Ser Thr
                 85                  90                  95

Arg Phe Thr Pro Tyr Ile Gly Ile Gly Ala Thr Ala Phe Ile Pro Trp
            100                 105                 110

Asp Glu Gln Gly Val Ala Asp Lys Val Lys Glu Asp Phe Gly Val Ala
            115                 120                 125

Gly Gln Ile Gly Phe Asn Phe Gln Pro Ala Asp Ala Lys Asn Trp Gly
        130                 135                 140

Val Phe Val Asp Val Arg Tyr Ala Asp Ile Ser Pro Glu Val Thr Leu
145                 150                 155                 160

Thr Asn Gly Ala Lys Phe Asp Leu Asp Ile Asn Pro Phe Val Tyr Thr
                165                 170                 175

Leu Gly Tyr Ser Tyr Lys Phe
            180
```

<210> SEQ ID NO 66
<211> LENGTH: 231
<212> TYPE: PRT
<213> ORGANISM: Acinetobacter baumannii

<400> SEQUENCE: 66

```
Met Met Lys Ile Leu Lys Leu Ser Phe Leu Ala Leu Gly Met Gly Leu
1               5                   10                  15

Ser Gly Phe Ala Gln Ala Asp Phe Ile Gly Val Lys Gly Asp Val Gly
            20                  25                  30

Tyr Trp Phe Tyr Asp Gly Lys Ala Asn Met Ser Ser Gln Ser Pro Glu
        35                  40                  45

Asp Gln Asp Leu Asp Arg Lys Gly Ser Ala Gln Leu Ser Leu Ala Phe
    50                  55                  60

Glu His Pro Ile Pro Phe Ile Pro Asn Ala Lys Ile Arg Tyr Val Asn
65                  70                  75                  80

Leu Asp Thr Gln Thr Lys Ser Glu Thr Leu Gly Gln Ala Asn Tyr Asn
                85                  90                  95

Val Asp Leu Asp His Ser Asp Phe Ile Leu Tyr Tyr Glu Leu Leu Asp
            100                 105                 110

Asn Ile Val Ser Val Asp Ala Gly Leu Gly Ala Thr Val Leu Asn Gly
            115                 120                 125

Asp Ile Thr Ala Tyr Thr Gly Lys Arg Val Asp Ile Asp Lys Thr Tyr
    130                 135                 140

Pro Ile Ala Tyr Leu Ser Gly Glu Val Lys Leu Pro Phe Thr Gly Leu
145                 150                 155                 160

Ser Ala Lys Gly Glu Ala Thr Tyr Thr Asn Phe Asp Ala Lys Ile
                165                 170                 175

Thr Asp Ala Leu Val Glu Ala Lys Tyr Lys Phe Ala Asp Asn Leu Leu
            180                 185                 190

Ile Asp Leu Gly Leu Thr Ala Gly Tyr Arg Ile Leu Asn Ile Asp Leu
            195                 200                 205

Asp Asp Tyr Asp Asn Asn Asp Leu Lys Phe Glu Phe Lys Gly Pro Tyr
    210                 215                 220

Val Gly Leu Glu Ala His Phe
225                 230

<210> SEQ ID NO 67
<211> LENGTH: 142
<212> TYPE: PRT
<213> ORGANISM: Acinetobacter baumannii

<400> SEQUENCE: 67

Met Asp Asp Leu Lys Glu Asn Val Lys Glu Lys Gln Thr Ala Gly Lys
1               5                   10                  15

Glu Ala Val Ala Asp Lys Val Asp Glu Leu Lys Thr Lys Ala Ala Asp
            20                  25                  30

Ala Lys Val Gln Gly Glu Lys Ala Leu Glu Asp Leu Lys Glu Asn Val
            35                  40                  45

Lys Glu Lys Gln Ala Ala Lys Glu Ala Val Glu Asp Lys Ala Ser
    50                  55                  60

Asp Leu Lys Gly Lys Leu Asp Asp Ala Gln His Ser Leu Gln Asp Lys
65                  70                  75                  80

Phe Asp His Leu Arg Thr Glu Ala Ala His Lys Leu Asp Asp Ala Lys
                85                  90                  95

Ala Lys Ala Ala Glu Leu Lys Glu Glu Ala Ala Thr Lys Phe Asp Glu
            100                 105                 110

Leu Lys Thr Gln Ala Thr Ala Lys Phe Asp Glu Leu Lys Lys Thr Ala
            115                 120                 125

Thr Glu Lys Leu Asn Lys Leu Lys Asn His Asp Ser Ala Glu
            130                 135                 140
```

<210> SEQ ID NO 68
<211> LENGTH: 344
<212> TYPE: PRT
<213> ORGANISM: Acinetobacter baumannii

<400> SEQUENCE: 68

Met Lys Ala Gln Val His Ala Gly Gly Arg Gly Lys Ala Gly Gly Val
1               5                   10                  15

Lys Val Ala Lys Ser Lys Glu Asp Val Ile Glu Phe Ala Asn Asn Ile
                20                  25                  30

Ile Gly Thr Arg Leu Val Thr Tyr Gln Thr Asp Ala Asn Gly Gln Pro
            35                  40                  45

Val Asn Ser Ile Ile Val Ala Glu Asp Val Tyr Pro Val Glu Arg Glu
        50                  55                  60

Leu Tyr Leu Gly Ala Val Val Asp Arg Ser Arg Arg Ile Thr Phe
65                  70                  75                  80

Met Ala Ser Thr Glu Gly Gly Val Glu Ile Lys Val Ala Glu Glu
                85                  90                  95

Thr Pro Glu Lys Ile Ile Lys Val Glu Val Asp Pro Leu Val Gly Leu
                100                 105                 110

Gln Pro Phe Gln Ala Arg Glu Val Ala Phe Ala Leu Gly Leu Lys Asp
            115                 120                 125

Lys Gln Ile Gly Gln Phe Val Lys Ile Met Thr Ala Ala Tyr Gln Ala
        130                 135                 140

Phe Val Glu Asn Asp Phe Ala Leu Phe Glu Ile Asn Pro Leu Ser Val
145                 150                 155                 160

Arg Glu Asn Gly Glu Ile Leu Cys Val Asp Ala Lys Val Gly Ile Asp
                165                 170                 175

Ser Asn Ala Leu Tyr Arg Leu Pro Lys Val Ala Ala Leu Arg Asp Lys
            180                 185                 190

Ser Gln Glu Asn Glu Arg Glu Leu Lys Ala Ser Glu Phe Asp Leu Asn
        195                 200                 205

Tyr Val Ala Leu Glu Gly Asn Ile Gly Cys Met Val Asn Gly Ala Gly
    210                 215                 220

Leu Ala Met Ala Thr Met Asp Ile Ile Lys Leu Tyr Gly Gly Gln Pro
225                 230                 235                 240

Ala Asn Phe Leu Asp Val Gly Gly Gly Ala Thr Lys Glu Arg Val Ile
                245                 250                 255

Glu Ala Phe Lys Ile Ile Leu Ala Asp Thr Ser Val Gln Gly Val Leu
            260                 265                 270

Ile Asn Ile Phe Gly Gly Ile Val Arg Cys Asp Met Ile Ala Glu Ala
        275                 280                 285

Ile Ile Ala Ala Val Gln Glu Val Asn Val Thr Val Pro Val Val Val
    290                 295                 300

Arg Leu Glu Gly Asn Asn Ala Glu Leu Gly Ala Lys Leu Leu Asp Glu
305                 310                 315                 320

Ser Gly Leu Lys Leu Ile Ser Ala Asn Gly Leu Ser Asp Ala Ala Glu
                325                 330                 335

Lys Val Val Ala Ala Val Lys Ala
            340

<210> SEQ ID NO 69
<211> LENGTH: 415
<212> TYPE: PRT

<213> ORGANISM: Acinetobacter baumannii

<400> SEQUENCE: 69

```
Met Met Ser Ala Lys Leu Trp Ala Pro Ala Leu Thr Ala Cys Ala Leu
1               5                   10                  15

Ala Thr Ser Ile Ala Leu Val Gly Cys Ser Lys Gly Ser Asp Glu Lys
            20                  25                  30

Gln Gln Ala Ala Ala Gln Lys Met Pro Pro Ala Glu Val Gly Val
        35                  40                  45

Ile Val Ala Gln Pro His Ser Val Glu Gln Ser Val Glu Leu Ser Gly
    50                  55                  60

Arg Thr Ser Ala Tyr Gln Ile Ser Glu Val Arg Pro Gln Thr Ser Gly
65                  70                  75                  80

Val Ile Leu Lys Arg Leu Phe Ala Glu Gly Ser Tyr Val Arg Glu Gly
                85                  90                  95

Gln Ala Leu Tyr Glu Leu Asp Ser Arg Thr Asn Arg Ala Thr Leu Glu
            100                 105                 110

Asn Ala Lys Ala Thr Leu Leu Gln Gln Gln Ala Asn Leu Ala Ser Leu
        115                 120                 125

Arg Thr Lys Leu Asn Arg Tyr Lys Gln Leu Val Ser Ser Asn Ala Val
    130                 135                 140

Ser Lys Gln Glu Tyr Asp Asp Leu Leu Gly Gln Val Asn Val Ala Glu
145                 150                 155                 160

Ala Gln Val Ser Ala Ala Lys Ala Gln Val Thr Asn Ala Asn Val Asp
                165                 170                 175

Leu Gly Tyr Ser Thr Ile Arg Ser Pro Ile Ser Gly Gln Ser Gly Arg
            180                 185                 190

Ser Ser Val Thr Ala Gly Ala Leu Val Thr Ala Asn Gln Thr Asp Pro
        195                 200                 205

Leu Val Thr Ile Gln Gln Leu Asp Pro Ile Tyr Val Asp Ile Asn Gln
    210                 215                 220

Ser Ser Ala Glu Leu Leu Arg Leu Arg Gln Gln Leu Ser Lys Gly Ser
225                 230                 235                 240

Leu Asn Asn Ser Asn Asn Thr Lys Val Lys Leu Lys Leu Glu Asp Gly
                245                 250                 255

Ser Thr Tyr Pro Ile Glu Gly Gln Leu Ala Phe Ser Asp Ala Ser Ala
            260                 265                 270

Asn Gln Asp Thr Gly Thr Ile Thr Leu Arg Ala Val Phe Ser Asn Pro
        275                 280                 285

Asn His Leu Leu Leu Pro Gly Met Tyr Thr Thr Ala Gln Ile Val Gln
    290                 295                 300

Gly Val Val Pro Asn Ala Tyr Leu Ile Pro Gln Ala Ala Ile Thr Arg
305                 310                 315                 320

Leu Pro Thr Gly Gln Ala Val Ala Met Leu Val Asn Ala Lys Gly Ala
                325                 330                 335

Val Glu Ser Arg Pro Val Glu Thr Ser Gly Val Gln Gly Gln Asn Trp
            340                 345                 350

Ile Val Thr Asn Gly Leu Lys Ala Gly Asp Lys Val Ile Val Asp Gly
        355                 360                 365

Val Ala Lys Val Lys Glu Gly Gln Glu Val Ser Ala Lys Pro Tyr Gln
    370                 375                 380

Ala Gln Pro Ala Asn Pro Gln Gly Ala Ala Pro Asn Ala Thr Lys Pro
385                 390                 395                 400
```

```
Ala Gln Ser Gly Lys Pro Gln Ala Glu Gln Lys Ala Ser Asn Ala
            405                 410                 415

<210> SEQ ID NO 70
<211> LENGTH: 656
<212> TYPE: PRT
<213> ORGANISM: Acinetobacter baumannii

<400> SEQUENCE: 70

Met Asp Ser Ser Ser Ala Thr Arg Ser Glu Ile Ala Leu Gln Asp
1               5                   10                  15

Thr Pro Gln Ser Val Ser Val Thr Gln Lys Val Ile Glu Asp Ile
                20                  25                  30

Gly Ala Thr Arg Leu Val Glu Ala Leu Asp Leu Ala Gly Gly Val Thr
                35                  40                  45

Arg Ala Asn Asn Phe Gly Gly Gln Gly Leu Thr Gly Phe Asn Val Arg
50                  55                  60

Gly Phe Thr Ser Gly Glu Phe Tyr Arg Asn Gly Phe Pro Ile Asn Arg
65                  70                  75                  80

Gly Tyr Pro Asn Ala Pro Asp Ser Asn Thr Ile Glu Arg Val Asp Val
                85                  90                  95

Leu Arg Gly Pro Ser Ser Leu Tyr Gly Arg Gly Asp Pro Gly Gly
                100                 105                 110

Thr Phe Asn Leu Ile Ser Lys Thr Pro Asn Ser Glu Gln Gln Thr Thr
                115                 120                 125

Leu Gly Ala Gln Leu Asn Ser Glu Gly Leu Tyr Arg Thr Thr Val Asp
                130                 135                 140

Thr Thr Gly Thr Ile Pro Asn Ala Glu Asn Ile Gly Tyr Arg Leu Asn
145                 150                 155                 160

Val Ile Ala Glu Gly Gly Asp Ser Tyr Arg Asp His Val Glu Ser Lys
                165                 170                 175

Arg Tyr Gly Ile Ala Pro Val Ile Gln Trp Gln Ala Thr Asp Ala Thr
                180                 185                 190

Lys Val Thr Phe Glu Ala Asp Ile Leu Arg Asn Gln His Pro Leu Asp
                195                 200                 205

Arg Gly His Thr Arg Tyr Pro Thr Gln Lys Ser Phe Asn Ser Ser Pro
                210                 215                 220

Glu Thr Tyr Leu Trp Glu Thr Gly Lys Tyr Tyr Asn Arg Leu Tyr Asn
225                 230                 235                 240

Asp Asn Asn Met Thr Gln Leu Arg Val Glu His Asp Leu Gly Asn Asp
                245                 250                 255

Trp Lys Leu Asn Ala Gly Val Gln Tyr Leu Asn Gly Lys Leu His Gly
                260                 265                 270

Tyr Ala Val Glu Ala Asn Gly Ile Gln Asn Asp Gly Glu Thr Leu Gly
                275                 280                 285

Arg Asn Tyr Asn Tyr Arg Glu Leu Lys Trp Gln Asp Thr Asp Ala Gln
                290                 295                 300

Ile Asn Leu Thr Gly Asn Phe Gln Leu Leu Gly Leu Ala His Thr Leu
305                 310                 315                 320

Val Thr Gly Leu Glu Tyr Glu Asn Tyr Asp Tyr Lys Ser Tyr Ile Ile
                325                 330                 335

Arg Ser Ser Glu Asp Ile Gly Ser Tyr Ser Ile Asn Ile Tyr Asn Pro
                340                 345                 350

Val Leu Gly Gln Pro Leu Pro Glu Leu Asn Thr Val Thr Thr His Asp
                355                 360                 365
```

```
Arg Glu Asn Leu Lys Thr Thr Ala Leu Phe Val Gln Asp Gln Leu Glu
        370                 375                 380

Leu Asn Glu Arg Leu Ser Ala Leu Leu Gly Leu Arg Phe Glu His Tyr
385                 390                 395                 400

Glu His Asp Tyr Gln Asp Leu Arg Pro Gly Lys Pro Asn Trp Asn Thr
                405                 410                 415

Ser His Asp Ala Phe Ile Pro Arg Leu Gly Leu Val Tyr Lys Ala Ser
                420                 425                 430

Asp Asp Leu Ser Leu Tyr Gly Asn Ala Ala Lys Ser Phe Lys Pro Asn
            435                 440                 445

Thr Gly Ala Ser His Ser Gly Glu Gly Phe Asp Pro Glu Glu Gly Met
450                 455                 460

Ala Tyr Glu Leu Gly Phe Lys Trp Leu Ala Leu Asn Asn Met Leu Ser
465                 470                 475                 480

Val Asp Ser Ala Ile Phe Tyr Ala Asn Lys Glu Asn Val Leu Thr Asn
                485                 490                 495

Asp Pro Leu Phe Pro Asn Tyr Lys Val Ala Ala Gly Glu Val Arg Ser
            500                 505                 510

Arg Gly Ile Glu Leu Asn Ile Ala Gly Gln Ile Thr Pro Ala Trp Lys
        515                 520                 525

Ile Ile Gly Gly Tyr Ala Tyr Thr Asp Ala Glu Val Thr Lys Asp Asn
530                 535                 540

Thr Leu Gln Lys Gly Thr Ala Leu Ala Asn Ile Pro Lys Asn Ser Phe
545                 550                 555                 560

Asn Leu Leu Asn Ile Tyr Glu Phe Gln Asp Gly Pro Leu Gln Gly Leu
                565                 570                 575

Gly Leu Gly Ile Asn Gln Lys Tyr Ile Asp Lys Arg Ala Gly Gln Thr
            580                 585                 590

Ala Asn Ser Thr Tyr Ile Met Lys Gly Tyr Ala Val Thr Asp Leu Val
        595                 600                 605

Ser Tyr Tyr Gln Ala Thr Pro Lys Leu Arg Leu Asn Leu Asp Val Lys
610                 615                 620

Asn Ile Phe Asp Lys Val Tyr Asp Glu Ser Ala Phe Asn Leu Tyr Ala
625                 630                 635                 640

Tyr Pro Gly Glu Ser Arg Thr Val Gln Leu Gly Met Ser Tyr Thr Phe
                645                 650                 655

<210> SEQ ID NO 71
<211> LENGTH: 177
<212> TYPE: PRT
<213> ORGANISM: Acinetobacter baumannii

<400> SEQUENCE: 71

Met Asp Arg Met Arg Gly Glu Asp Asp Tyr Lys Ser Thr Tyr Phe Glu
1                5                  10                  15

Leu Ser Pro Arg Leu Ser Leu Gly Glu Val Ser Gly Lys Lys Leu Thr
            20                  25                  30

Tyr Gly Pro Ile Lys Asp Val Leu Ile Ser Thr Thr Trp Glu Ser Asn
        35                  40                  45

Thr Gln Asn Gly Asn Asn Phe Asp Asn Phe Leu Tyr Gly Phe Ala Val
    50                  55                  60

Asp Leu Asp Ile Pro Tyr Phe Gln Tyr Ala Asn Leu Asn Phe Tyr Arg
65                  70                  75                  80

Ala Asn Asn Glu Lys Thr Asp Asp Asp Tyr Gln Met Thr Phe Val Tyr
```

```
                    85                  90                  95

Gly Ile Pro Phe Lys Ile Ala Ser Glu Asp Phe Leu Val Asp Gly Phe
                100                 105                 110

Leu Asp Trp Ser Thr Ala Glu Asp His Ala Ser Glu Leu Asn Trp
                115                 120                 125

Thr Thr Gln Trp Lys Trp Asn Val Gly Lys His Ile Ser Pro Asp Thr
    130                 135                 140

Arg Leu Tyr Leu Gly Ile Glu His Ser Val Trp Asn Asn Lys Phe Gly
145                 150                 155                 160

Ile Lys Gly Ala Asp Glu Asn Asn Val Ser Ala Leu Val Lys Tyr His
                165                 170                 175

Phe

<210> SEQ ID NO 72
<211> LENGTH: 581
<212> TYPE: PRT
<213> ORGANISM: Acinetobacter baumannii

<400> SEQUENCE: 72

Met Tyr Ala Asn Lys Asn Gln Lys Ser Glu Val Thr Tyr Ala Gly Tyr
1               5                   10                  15

Phe Leu Ser Glu Asn Gly Asn Asn Leu Lys Glu Leu Lys Ala
                20                  25                  30

Asp Ile Ser Ala Leu Phe Ile Pro Thr Gln Asp Asn Gln Ser Ile Arg
            35                  40                  45

Cys Lys Phe Pro Ala Arg Ser Gln Trp Leu Ile Gln Gln Leu Gly Ile
50                  55                  60

Gln Glu Asn Glu Leu Pro Gln Val Lys Cys Ser Glu Phe Glu Asn Trp
65                  70                  75                  80

Ile Gly Gln Ile Lys Pro Tyr Lys Ala Thr Leu Ile Tyr Ala Thr Asp
                85                  90                  95

Phe Met Gly Asn Pro Ser Ser Met Phe Gly His Thr Leu Leu Arg Leu
                100                 105                 110

Asp Pro Lys Asp Gln Gln Gln Leu Asn Leu Val Ser Tyr Ala Val Asn
            115                 120                 125

Tyr Ala Ala Thr Val Ala Gly Asn Asp Asn Trp Ser Tyr Ala Trp Lys
        130                 135                 140

Gly Leu Thr Gly Gln Tyr Pro Gly Glu Tyr Ser Leu Met Pro Tyr Tyr
145                 150                 155                 160

Arg Lys Val Lys Glu Tyr Gly Asp Phe Glu Ser Arg Asp Leu Trp Glu
                165                 170                 175

Tyr Glu Leu Asn Leu Ser Pro Glu Glu Thr Arg Phe Leu Val Ser His
            180                 185                 190

Ile Trp Glu Met Gln His Val Ser Phe Pro Tyr Tyr Phe Val Ser Asp
        195                 200                 205

Asn Cys Ala Tyr Arg Leu Leu Gly Leu Val Asp Leu Val Lys Pro Glu
    210                 215                 220

Ser His Leu Gln Glu Lys Phe Asn Tyr Ala Ser Ile Pro Met Glu Thr
225                 230                 235                 240

Ile Lys Ala Met Gln Gln Gln Gly Leu Thr Lys Ala Pro Val Tyr Arg
                245                 250                 255

Pro Ala Leu Glu Thr Gln Leu Leu Ala Gln Ala His Gln His Gly Ala
            260                 265                 270

Ser Leu Ala Lys Val Ala His Gln Leu Ala Met Lys Pro Ile Lys Glu
```

```
                275                 280                 285
Ser Ser Glu Thr Leu Lys Ser Phe Ser Pro Ser Asp Gln Ala Lys Ile
    290                 295                 300
Leu Glu Met Ala Tyr Asp Asp Leu Tyr Leu Gln Phe Ile Gly Arg Lys
305                 310                 315                 320
Val Glu Glu Ser Phe Ala Gln Pro Gln Leu Arg Gln Leu Leu Ala Leu
                325                 330                 335
Arg Ser Gln Ile Asp Leu Asp Lys Gln Arg Gln Glu Pro Lys Arg Pro
            340                 345                 350
Ser Thr Glu Pro Thr Gln Gly His Asn Ala Arg Asn Val Ser Leu Lys
        355                 360                 365
Leu Gly Glu Val Gln Gly Asp Lys Phe Ile Glu Ile Gly His Arg Gln
    370                 375                 380
Ala Tyr His Asp Leu Ile Asp Pro Gln Gly Gly Tyr Arg Ala Gly Thr
385                 390                 395                 400
Gln Leu Leu Phe Leu Asn Gly Asn Ala Gln Trp Arg Asp Asp His Leu
                405                 410                 415
Lys Leu Glu Arg Leu Asp Leu Leu Glu Val Asn Ser Tyr Asn Pro Ile
            420                 425                 430
Gln Pro Phe Lys Thr Pro Leu Thr Trp Gly Phe Asn Leu Gly Trp Arg
        435                 440                 445
Gln Glu Ala Val His Asp Gly Val Tyr Ser Asp Glu Lys Gln His Gly
    450                 455                 460
Val Ala Ser Phe Asn Ala Gln Val Gly Tyr Ser Leu Ala Asp Tyr Glu
465                 470                 475                 480
Arg Lys His Ile Cys Tyr Gly Gln Val Gln Thr Tyr Val Gln Ala Gly
                485                 490                 495
Ser Asn Leu Asp Lys Gly Trp Arg Val Gly Val Gly Pro Thr Leu Gly
            500                 505                 510
Cys Met Asn Gln Trp Leu Glu Lys Phe Asn Thr Val Val Gln Val Glu
        515                 520                 525
Leu Pro Tyr Trp Glu Asp Gln Asn Gln Trp Asn Leu Arg Leu Asn Thr
    530                 535                 540
Gln Trp Gln Tyr Ala Ile Asn Ser Asn Asn Ala Ile Arg Phe Asn Trp
545                 550                 555                 560
Asp Tyr Glu Lys Gln Asn His Leu Asp Trp Met Lys Ser Ser Leu Gly
                565                 570                 575
Tyr Val Trp Phe Phe
            580

<210> SEQ ID NO 73
<211> LENGTH: 205
<212> TYPE: PRT
<213> ORGANISM: Acinetobacter baumannii

<400> SEQUENCE: 73

Met Arg Gly Asn Asn Val Asn Leu Lys Thr Val Ser Gly Ser Ala Val
1               5                   10                  15
Glu Leu Ser Glu Val Ala Phe Gly Arg Glu Phe Asn Glu Ala Leu Val
            20                  25                  30
His Gln Val Val Thr Ala Tyr Leu Ala Gly Gly Arg Gln Gly Thr Arg
        35                  40                  45
Ala Gln Lys Ser Arg Ala Glu Val Ser Gly Gly Gly Lys Lys Pro Phe
    50                  55                  60
```

Arg Gln Lys Gly Thr Gly Arg Ala Arg Ala Gly Ile Arg Ser Pro
65                  70                  75                  80

Ile Trp Val Gly Gly Lys Thr Phe Ala Ala Arg Pro Gln Asp Trp
                85                  90                  95

Ser Gln Lys Val Asn Arg Lys Met Tyr Arg Gly Ala Met Gln Cys Ile
            100                 105                 110

Leu Ala Glu Leu Val Arg Gln Asp Arg Leu Val Leu Val Glu Glu Phe
            115                 120                 125

Ala Val Ala Ala Pro Lys Thr Lys Glu Leu Leu Ala Lys Leu Asn Asp
        130                 135                 140

Leu Asn Ala Ala Arg Ala Leu Ile Val Thr Asp Ala Val Asp Glu Asn
145                 150                 155                 160

Leu Tyr Leu Ala Ala Arg Asn Leu Pro His Val Asp Val Val Asp Ala
                165                 170                 175

Thr Ala Ile Asp Pro Val Ser Leu Ile Ala Phe Asp Lys Val Val Met
            180                 185                 190

Ser Val Ala Ala Lys Lys Ile Glu Val Glu Leu Gly
            195                 200                 205

<210> SEQ ID NO 74
<211> LENGTH: 152
<212> TYPE: PRT
<213> ORGANISM: Acinetobacter baumannii

<400> SEQUENCE: 74

Met Lys Gly Ser Lys Gly Thr Leu Ser Phe Asn Leu His Ala Leu Val
1               5                   10                  15

Glu Leu Lys Gln Glu Glu Gly Lys Leu Gln Leu Ala Pro Ala Lys Glu
                20                  25                  30

Ser Lys Asp Ala Trp Met Gln Ala Gly Thr Ala Arg Ala Val Leu Asn
            35                  40                  45

Asn Leu Val Lys Gly Val Ser Glu Gly Phe Glu Arg Lys Leu Gln Leu
        50                  55                  60

Val Gly Val Gly Tyr Lys Ala Ala Val Lys Gly Thr Val Val Asn Leu
65                  70                  75                  80

Asn Leu Gly Tyr Ser His Pro Ile Asp Tyr Ala Leu Pro Glu Gly Val
                85                  90                  95

Thr Ala Glu Thr Pro Thr Ala Thr Glu Ile Ile Leu Lys Ser Ala Asn
            100                 105                 110

Lys Gln Leu Leu Gly Gln Val Ala Ala Glu Ile Arg Ala Tyr Arg Ser
        115                 120                 125

Pro Glu Pro Tyr Lys Gly Lys Gly Val Arg Tyr Ser Asp Glu Val Ile
    130                 135                 140

Leu Arg Lys Glu Ala Lys Lys Lys
145                 150

<210> SEQ ID NO 75
<211> LENGTH: 221
<212> TYPE: PRT
<213> ORGANISM: Acinetobacter baumannii

<400> SEQUENCE: 75

Met Thr Asn Leu Thr Asp Tyr Val Val Leu Asn Thr Ser Val Ala Ser
1               5                   10                  15

Gly Glu Gln Asp Val Asn Ala Phe Gln Ser Phe Asn Tyr Leu Ala Ala
                20                  25                  30

Tyr Asn Ala Ser Asn Lys Ala Lys Val Ala Val Ala Thr Thr Tyr
            35                  40                  45

Leu Glu Pro Met Gly Ile Tyr Ala Asn Lys Val Lys Thr Val Asp Glu
 50                  55                  60

Phe Pro Gln Gly Ala Thr Ile Ala Ile Pro Asn Asp Thr Ala Asn Glu
 65                  70                  75                  80

Ala Arg Ala Leu Thr Leu Leu Gln Ser Ala Lys Leu Ile Lys Leu Lys
                 85                  90                  95

Pro Asp Phe Asp Pro Val Lys Gly Thr Thr Asn Asp Val Val Glu Asn
            100                 105                 110

Pro Lys Asn Leu Gln Leu Lys Pro Ile Gln Met Thr Thr Ala Val Arg
            115                 120                 125

Val Lys Asn Asp Val Asp Ala Ile Val Leu Gly Asn Thr Leu Ala Leu
130                 135                 140

Glu Gly Gly Leu Asn Val Met Lys Asp Ala Ile Phe Arg Glu Pro Ile
145                 150                 155                 160

Asp Gln Ser Thr Lys Leu Tyr Val Asn Leu Leu Gly Val Ala Glu Ala
                165                 170                 175

Asn Lys Asn Asp Pro Ile Tyr Thr Lys Leu Gly Glu Leu Tyr His Leu
            180                 185                 190

Pro Lys Val Gln Lys Phe Val Asn Glu Lys Phe Gly Gly Thr Lys Val
            195                 200                 205

Glu Val Asn Lys Pro Val Ser Glu Phe Ala Asp Ile Lys
210                 215                 220

<210> SEQ ID NO 76
<211> LENGTH: 99
<212> TYPE: PRT
<213> ORGANISM: Acinetobacter baumannii

<400> SEQUENCE: 76

Met Ala Thr Ala Val Arg Val Lys Asp Glu Val Asp Ala Ile Val Leu
 1                5                  10                  15

Gly Asn Thr Leu Ala Met Glu Gly Gly Leu Asn Val Leu Lys Asp Ser
                20                  25                  30

Ile Tyr Tyr Glu Pro Val Asp Gln Ser Thr Lys Leu Asn Val Asn Ile
            35                  40                  45

Leu Ala Thr Ala Glu Ser Arg Lys Asp Pro Val Leu Gln Lys Val
 50                  55                  60

Gly Gln Leu Tyr His Thr Glu Ala Val Lys Lys Tyr Val Glu Gln His
 65                  70                  75                  80

Phe Gly Gly Thr Lys Val Asp Val Asn Gln Pro Ile Ser Tyr Leu Thr
                85                  90                  95

Gln Ala Lys

<210> SEQ ID NO 77
<211> LENGTH: 169
<212> TYPE: PRT
<213> ORGANISM: Acinetobacter baumannii

<400> SEQUENCE: 77

Met Val Asn Glu Thr Met Lys His Gln Phe Lys Phe Asn Pro Leu Ala
 1                5                  10                  15

Thr Ala Ile Phe Thr Leu Leu Cys Ser Gly Ser Ile Gln Ser Ser Tyr
                20                  25                  30

Ala Glu Ser Ala Gly Val Val Ser Asn Ile Asp Asn Asn Gln Leu Lys

```
                35                  40                  45
Ala Ser Ile Lys Glu Ala Tyr Pro Gly Gln Glu Phe Phe Gln Gln Tyr
 50                  55                  60

Tyr Val Asp Lys Ser Ala Pro Glu Ala Gln Leu Arg Asn Asn Lys Tyr
 65                  70                  75                  80

Leu Ser Ser Ala Phe Cys Gln Gly Thr Trp Ile Thr Pro Ile Asn Pro
                 85                  90                  95

Glu Thr Lys Ala Leu Asp Ala Asp Lys Ala Thr Ser Val Val Thr Ala
                100                 105                 110

Asp Tyr Gly His Tyr Asn Pro Ala Gly Asp Ser Val Leu Glu Gly Asn
                115                 120                 125

Val Val Ile Asp Gln Glu Gly Arg Thr Val Arg Ala Asp Lys Val Thr
                130                 135                 140

Ile Asp Lys Thr Gln Thr Phe Ala His Ala Gln Gly Arg Val Gln Leu
145                 150                 155                 160

Ala Gln Gly Gly Leu Leu Ser Thr Lys
                165
```

<210> SEQ ID NO 78
<211> LENGTH: 236
<212> TYPE: PRT
<213> ORGANISM: Acinetobacter baumannii

<400> SEQUENCE: 78

```
Met Ser Arg Gly Thr Arg Thr Phe Glu Ile Tyr Arg Tyr Asp Pro Asp
 1               5                  10                  15

Lys Asp Lys Ala Pro Tyr Met Gln Thr Phe Lys Leu Glu Leu Thr Asp
                 20                  25                  30

Lys His Arg Met Leu Leu Asp Ala Leu Leu Ala Leu Lys Val Gln Asp
                 35                  40                  45

Glu Thr Leu Thr Phe Arg Arg Ser Cys Arg Glu Gly Ile Cys Gly Ser
 50                  55                  60

Asp Gly Val Asn Ile Asn Gly Lys Asn Gly Leu Ala Cys Leu Trp Asn
 65                  70                  75                  80

Leu Asn Asp Leu Pro Glu Lys Ile Val Ile Arg Pro Leu Pro Gly Leu
                 85                  90                  95

Pro Val Ile Lys Asp Leu Val Val Asp Met Asn Gln Phe Tyr Asp Gln
                100                 105                 110

Tyr Asp Lys Ile Gln Pro Phe Leu Ile Asn Asn Gln Pro Ala Pro Pro
                115                 120                 125

Lys Glu Arg Leu Gln Ser Pro Glu Glu Arg Glu His Leu Asn Gly Leu
                130                 135                 140

Tyr Glu Cys Ile Leu Cys Ala Cys Cys Ser Thr Ser Cys Pro Ser Phe
145                 150                 155                 160

Trp Trp Asn Pro Asp Lys Phe Leu Gly Pro Ser Ala Leu Leu Asn Ala
                165                 170                 175

Tyr Arg Phe Ile Ile Asp Ser Arg Asp Thr Ala Thr Gln Asp Arg Leu
                180                 185                 190

Ser Arg Leu Asp Asp Pro Phe Ser Leu Phe Arg Cys Lys Gly Ile Met
                195                 200                 205

Asn Cys Val Ser Val Cys Pro Lys Gly Leu Asn Pro Thr Lys Ala Ile
                210                 215                 220

Gly His Ile Arg Asn Met Leu Phe Asp Gln Ala Gly
225                 230                 235
```

<210> SEQ ID NO 79
<211> LENGTH: 300
<212> TYPE: PRT
<213> ORGANISM: Acinetobacter baumannii

<400> SEQUENCE: 79

Met Leu Gly Lys Asp Gln Pro Val Ile Leu Gln Leu Leu Glu Val Pro
1               5                   10                  15

Val Glu Lys Ala Gln Gln Ala Leu Lys Gly Val Met Met Glu Leu Asp
            20                  25                  30

Asp Cys Ala Phe Pro Leu Leu Ala Gly Met Ile Gly Thr Asp Asp Pro
        35                  40                  45

Lys Val Ala Phe Lys Asp Ala Asp Tyr Ala Leu Leu Val Gly Ser Arg
    50                  55                  60

Pro Arg Gly Pro Gly Met Glu Arg Ala Asp Leu Leu Lys Val Asn Gly
65                  70                  75                  80

Glu Ile Phe Ile Gly Gln Gly Gln Ala Leu Asn Glu Val Ala Ser Arg
                85                  90                  95

Asp Val Lys Val Leu Val Gly Asn Pro Ala Asn Thr Asn Ala Tyr
            100                 105                 110

Ile Ala Met Lys Ser Ala Pro Asp Leu Pro Ala Lys Asn Phe Thr Ala
        115                 120                 125

Met Leu Arg Leu Asp His Asn Arg Ala Leu Thr Gln Val Ala Gln Lys
    130                 135                 140

Ala Gly Val Ala Val Ala Asp Ile Glu Lys Leu Thr Val Trp Gly Asn
145                 150                 155                 160

His Ser Pro Thr Met Tyr Ala Asp Tyr Arg Phe Ala Thr Ala Asn Gly
                165                 170                 175

Glu Ser Leu Lys Asp Lys Ile Asn Asp Pro Ala Trp Asn Lys Asp Val
            180                 185                 190

Phe Leu Pro Thr Val Gly Lys Arg Gly Ala Ala Ile Ile Glu Ala Arg
        195                 200                 205

Gly Leu Ser Ser Ala Ala Ser Ala Ala Asn Ala Ala Ile Asp His Met
    210                 215                 220

Arg Asp Trp Ala Leu Gly Thr Asn Gly Lys Trp Val Thr Met Gly Val
225                 230                 235                 240

Pro Ser Asp Gly Ser Tyr Gly Ile Pro Glu Gly Val Met Phe Gly Phe
                245                 250                 255

Pro Val Thr Thr Glu Asn Gly Glu Tyr Lys Ile Val Gln Gly Leu Glu
            260                 265                 270

Ile Asp Glu Phe Ser Arg Glu Arg Ile Asn Phe Thr Leu Asn Glu Leu
        275                 280                 285

Glu Glu Glu Arg Ala Ala Ile Ala Asp Met Val Lys
    290                 295                 300

<210> SEQ ID NO 80
<211> LENGTH: 373
<212> TYPE: PRT
<213> ORGANISM: Acinetobacter baumannii

<400> SEQUENCE: 80

Met Gly Glu Pro Val Ser Arg Asp Glu Val Ile Cys Asp Ile Glu Thr
1               5                   10                  15

Asp Lys Val Val Leu Glu Val Val Ala Pro Ala Asp Gly Ser Leu Val
            20                  25                  30

```
Ala Ile Ile Lys Gly Glu Gly Asp Thr Val Leu Ser Asp Glu Val Ile
             35                  40                  45

Ala Gln Phe Glu Ala Gly Ala Gly Ala Ala Ala Pro Ala Ala
 50                  55                  60

Val Glu Gln Ala Val Gln Thr Gln Ala Gly Ala Ala Pro Val Val
 65                  70                  75                  80

Glu Arg Asn Glu Thr Val Ser Asp Gln Ala Pro Ala Val Arg Lys Ala
                 85                  90                  95

Leu Thr Glu Ser Gly Ile Ala Ala Ser Asp Val Gln Gly Thr Gly Arg
                100                 105                 110

Gly Gly Arg Ile Thr Lys Glu Asp Val Ala Asn His Gln Ala Lys Pro
            115                 120                 125

Ala Ala Asn Val Thr Pro Leu Ser Val Ala Val Gly Glu Arg Ile Glu
    130                 135                 140

Lys Arg Val Pro Met Thr Arg Leu Arg Lys Arg Val Ala Glu Arg Leu
145                 150                 155                 160

Leu Ala Ala Thr Gln Glu Thr Ala Met Leu Thr Thr Phe Asn Glu Val
                165                 170                 175

Asn Met Lys Pro Ile Met Glu Leu Arg Lys Gln Tyr Lys Asp Ala Phe
            180                 185                 190

Glu Lys Arg His Gly Ala Arg Leu Gly Phe Met Ser Phe Val Lys
        195                 200                 205

Ala Ala Thr Glu Ala Leu Lys Arg Tyr Pro Ala Val Asn Ala Ser Ile
    210                 215                 220

Asp Gly Asp Asp Ile Val Tyr His Gly Tyr Tyr Asp Ile Gly Val Ala
225                 230                 235                 240

Val Ser Ser Asp Arg Gly Leu Val Val Pro Val Leu Arg Asp Thr Asp
                245                 250                 255

Arg Met Ser Tyr Ala Glu Val Glu Ala Gly Ile Ala Ala Tyr Ala Ala
            260                 265                 270

Lys Ala Arg Asp Gly Lys Leu Ser Ile Glu Glu Met Thr Gly Gly Thr
    275                 280                 285

Phe Thr Ile Thr Asn Gly Gly Thr Phe Gly Ser Leu Leu Ser Thr Pro
290                 295                 300

Ile Leu Asn Gln Pro Gln Thr Gly Ile Leu Gly Met His Lys Ile Gln
305                 310                 315                 320

Glu Arg Pro Met Ala Val Asn Gly Gln Val Glu Ile Leu Pro Met Met
                325                 330                 335

Tyr Leu Ala Leu Ser Tyr Asp His Arg Met Ile Asp Gly Lys Glu Ala
            340                 345                 350

Val Gly Phe Leu Val Ala Ile Lys Glu Leu Leu Glu Glu Pro Ala Lys
    355                 360                 365

Leu Ile Leu Asp Leu
    370

<210> SEQ ID NO 81
<211> LENGTH: 468
<212> TYPE: PRT
<213> ORGANISM: Acinetobacter baumannii

<400> SEQUENCE: 81

Met Ser Phe Ser Met Thr Lys Leu Ser Ala Leu Leu Leu Thr Ser
1               5                   10                  15

Ser Leu Val Gly Cys Ala Ala Val Val Lys Thr Pro Tyr Gln Ala Pro
            20                  25                  30
```

```
Ala Val Gln Val Pro Gly Ser Phe Gln Tyr Asp Lys Ala Lys Ala Lys
            35                  40                  45

Thr Ala Ser Val Glu Gln Tyr Ser Asp Arg Trp Trp Thr Leu Phe Gly
 50                  55                  60

Asp Thr Gln Leu Asn Gln Leu Val Thr Asn Val Leu Glu Arg Asn Ser
 65                  70                  75                  80

Asp Leu Ala Val Ala Gly Ile Thr Leu Gln Gln Ala Arg Leu Gln Ala
                85                  90                  95

Asp Leu Thr Ala Asn Lys Gln Gly Leu Arg Thr Ser Ser Ser Val Ser
            100                 105                 110

Thr Gly His Ser Phe Asp Leu Asn Ser Gly Asp Ser Ala Lys Gly
            115                 120                 125

Leu Ser Met Ser Ala Gly Val Ser Tyr Glu Leu Asp Leu Phe Gly Lys
130                 135                 140

Leu Ala Arg Gln Thr Glu Ala Ser Lys Trp Glu Ala Leu Ala Thr Glu
145                 150                 155                 160

Gln Asp Leu Gln Ala Thr Gly Gln Ser Leu Ile Ala Thr Ala Lys
            165                 170                 175

Leu Tyr Trp Gln Leu Gly Tyr Leu Asn Glu Arg Tyr Ala Thr Ala Gln
            180                 185                 190

Gln Ser Leu Ala Thr Ser Gln Lys Leu Tyr Gln Leu Val Gln Thr Gln
            195                 200                 205

Tyr Lys Ala Gly Ala Val Ser Gly Leu Asp Leu Thr Gln Ala Glu Gln
            210                 215                 220

Ser Val Gln Ser Gln Lys Ala Ser Leu Ser Gln Ile Glu Gln Gln Leu
225                 230                 235                 240

Val Glu Thr Arg Thr Ala Ile Ala Val Leu Leu His Glu Pro Leu Gln
            245                 250                 255

Gln Leu Asn Ile Gln Glu Pro Gln Arg Leu Pro Arg Thr Ala Leu Pro
            260                 265                 270

Ala Ile Gly Ala Gly Leu Pro Ala Asp Ile Leu Ser Arg Arg Pro Asp
            275                 280                 285

Leu Gln Ala Ala Glu Leu Arg Leu Arg Lys Ala Leu Ala Thr Lys Asp
            290                 295                 300

Ala Thr Lys Ala Ser Tyr Tyr Pro Ser Ile Ser Leu Thr Ser Ser Leu
305                 310                 315                 320

Gly Ser Ser Ser Thr Ser Leu Thr Glu Leu Leu Arg Asn Pro Ala Leu
            325                 330                 335

Thr Leu Gly Ala Ser Leu Ser Leu Pro Phe Leu Gln Tyr Asn Asp Met
            340                 345                 350

Lys Lys Asp Ile Ala Ile Ser Asn Leu Asp Tyr Glu Lys Ala Ile Ile
            355                 360                 365

Gln Tyr Arg Gln Thr Leu Tyr Gln Ala Phe Ala Asp Val Glu Asn Ala
            370                 375                 380

Leu Ser Ser Arg Thr Glu Leu Asp Lys Gln Val Ala Leu Gln Glu Arg
385                 390                 395                 400

Asn Val Glu Leu Ala Glu Lys Thr Glu Arg Leu Thr Glu Val Arg Tyr
                    405                 410                 415

Arg Tyr Gly Ala Val Ala Leu Lys Thr Leu Leu Asp Ala Gln Gln Thr
            420                 425                 430

Thr Arg Thr Ala Arg Leu Ser Leu Val Glu Thr Lys Gln Ser Gln Tyr
            435                 440                 445
```

```
Asn Ala Tyr Val Thr Leu Met Gln Ala Leu Gly Gly Ser Pro Val Lys
    450                 455                 460

Glu Leu Pro Gln
465

<210> SEQ ID NO 82
<211> LENGTH: 358
<212> TYPE: PRT
<213> ORGANISM: Acinetobacter baumannii

<400> SEQUENCE: 82

Met Ala Tyr Ala Asp Thr Leu Ala Pro Val Lys Pro Ala Ser Val Asp
1               5                   10                  15

Ala Cys Val Ala Leu Ala Ser Asn Ala Asp Arg Leu Ala Cys Tyr Asp
                20                  25                  30

Ala Val Phe Lys Pro Ser Ala Leu Pro Val Val Gln Ala Ala Val Val
            35                  40                  45

Pro Glu Pro Val Lys Lys Ile Asp Lys Pro Val Gln Pro Glu Thr
        50                  55                  60

Phe Lys Glu Lys Val Val Asp Lys Val Ser Asn Ile Lys Val Ile Gly
65                  70                  75                  80

Lys Ala Pro Thr Leu Glu Pro Thr Thr Ser Leu Leu Asp Gln Arg Trp
                85                  90                  95

Glu Leu Ser Glu Lys Ser Lys Leu Gly Val Trp Asn Ile Arg Ala Tyr
            100                 105                 110

Gln Pro Val Tyr Leu Leu Pro Val Phe Trp Thr Ser Asp Lys Asn Glu
        115                 120                 125

Phe Pro Ser Ser Pro Asn Pro Asn Asn Thr Val Thr Glu Ala Gln Asn
130                 135                 140

Leu Lys Ser Thr Glu Ser Lys Phe Gln Ile Ser Leu Lys Thr Lys Ala
145                 150                 155                 160

Trp Glu Asn Ile Phe Gly Asn Asn Gly Asp Leu Trp Val Gly Tyr Thr
                165                 170                 175

Gln Ser Ser Arg Trp Gln Thr Phe Asn Ala Glu Glu Ser Arg Pro Phe
            180                 185                 190

Arg Glu Thr Asn Tyr Glu Pro Glu Ala Ser Leu Met Phe Arg Thr Asn
        195                 200                 205

Tyr Glu Leu Leu Gly Leu Asp Gly Arg Leu Leu Gly Val Thr Leu Asn
    210                 215                 220

His Gln Ser Asn Gly Arg Ser Asp Pro Leu Ser Arg Ser Trp Asn Arg
225                 230                 235                 240

Val Ile Phe Asn Val Gly Leu Glu Arg Gly Asn Phe Ala Leu Met Leu
                245                 250                 255

Arg Pro Trp Ile Arg Leu Glu Glu Asp Ser Lys Asp Asp Asn Asn Pro
            260                 265                 270

Asp Met Glu Asp Tyr Ile Gly Arg Gly Asp Leu Thr Ala Phe Tyr Lys
        275                 280                 285

Trp Lys Gln Asn Asp Phe Ser Leu Met Leu Arg His Ser Leu Lys Gly
    290                 295                 300

Gly Asp Asp Ser His Gly Ala Val Gln Phe Asp Trp Ala Phe Pro Ile
305                 310                 315                 320

Ser Gly Lys Leu Arg Gly His Phe Gln Leu Phe Asn Gly Tyr Gly Glu
                325                 330                 335

Ser Leu Ile Asp Tyr Asn His Arg Ala Thr Tyr Ala Gly Leu Gly Val
            340                 345                 350
```

Ser Leu Met Asn Trp Tyr
        355

<210> SEQ ID NO 83
<211> LENGTH: 108
<212> TYPE: PRT
<213> ORGANISM: Acinetobacter baumannii

<400> SEQUENCE: 83

Met Glu Gly Leu Ser Val Thr Tyr Asn Gly Ser Thr Asp Thr Ala Ile
1               5                   10                  15

Ile Lys Gly Gln Val Gln Ser Gln Ala Asp Lys Glu Lys Ile Ile Leu
            20                  25                  30

Ile Val Gly Asn Val Asp His Val Ala Gln Val Asp Asp Gln Met Thr
        35                  40                  45

Val Ala Thr Pro Glu Pro Glu Ser Lys Phe Tyr Thr Val Lys Ser Gly
    50                  55                  60

Asp Asn Leu Ser Lys Ile Ala Lys Glu Phe Tyr Gly Asp Ala Asn Gln
65                  70                  75                  80

Tyr Gln Lys Ile Phe Glu Ala Asn Lys Pro Met Leu Lys Asp Pro Asp
                85                  90                  95

Glu Ile Phe Pro Gly Gln Val Leu Arg Ile Pro Gln
            100                 105

<210> SEQ ID NO 84
<211> LENGTH: 291
<212> TYPE: PRT
<213> ORGANISM: Acinetobacter baumannii

<400> SEQUENCE: 84

Met Thr Ala Ile Thr Ala Ser Met Val Lys Glu Leu Arg Asp Arg Thr
1               5                   10                  15

Gly Leu Ala Met Met Glu Cys Lys Lys Ala Leu Thr Glu Ala Asn Gly
            20                  25                  30

Asp Ile Glu Leu Ala Ile Asp Asn Leu Arg Lys Ser Gly Gln Ala Lys
        35                  40                  45

Ala Ala Lys Lys Ala Gly Asn Ile Ala Ala Asp Gly Ala Ile Thr Ile
    50                  55                  60

Val Gln Asp Gly Asn Lys Ala Ile Leu Val Glu Val Asn Cys Gln Thr
65                  70                  75                  80

Asp Phe Val Ala Lys Asp Glu Asn Phe Ser Asn Phe Ala His Thr Val
                85                  90                  95

Ala Ala Ala Ala Leu Ala Ala Gly Glu Thr Asp Ala Ala Lys Ile Ala
            100                 105                 110

Glu Leu Lys Leu Ala Asp Gly Gln Ser Val Glu Ala Arg Ile Ala
        115                 120                 125

Leu Val Gln Lys Ile Gly Glu Asn Ile Gln Val Arg Arg Ala Lys Ile
    130                 135                 140

Val Glu Gly Glu Gln Leu Ala Ile Tyr Lys His Gly Leu Lys Ile Gly
145                 150                 155                 160

Val Val Val Ser Tyr Thr Gly Asp Ala Asp Thr Gly Lys Gly Ile Ala
                165                 170                 175

Met His Val Ala Ala Phe Asn Pro Val Ala Val Asn Ala Glu Ala Val
            180                 185                 190

Pro Ala Asp Leu Ile Ala Lys Glu Lys Glu Ile Ala Glu Ala Lys Ala
        195                 200                 205

Leu Glu Ser Gly Lys Pro Ala Asn Ile Val Glu Lys Met Val Thr Gly
            210                 215                 220

Ser Val Glu Lys Tyr Leu Asn Glu Val Ala Leu Asp Arg Gln Met Tyr
225                 230                 235                 240

Val Ile Asp Asn Glu Lys Lys Val Ala Asp Val Leu Lys Ala Thr Gly
                245                 250                 255

Thr Asn Val Ala Asn Phe Val Arg Phe Glu Val Gly Glu Gly Ile Glu
            260                 265                 270

Lys Lys Ala Glu Leu Ser Phe Ala Glu Glu Val Ala Ala Gln Ala
                275                 280                 285

Ala Ala Lys
        290

<210> SEQ ID NO 85
<211> LENGTH: 170
<212> TYPE: PRT
<213> ORGANISM: Acinetobacter baumannii

<400> SEQUENCE: 85

Met Thr Gly Cys Ala Ser Arg Lys Pro Ala Thr Thr Ala Thr Thr Gly
1               5                   10                  15

Thr Thr Asn Pro Ser Thr Val Asn Thr Thr Gly Leu Ser Glu Asp Ala
            20                  25                  30

Ala Leu Asn Ala Gln Asn Leu Ala Gly Ala Ser Ser Lys Gly Val Thr
        35                  40                  45

Glu Ala Asn Lys Ala Ala Leu Ala Lys Arg Val Val His Phe Asp Tyr
50                  55                  60

Asp Ser Ser Asp Leu Ser Thr Glu Asp Tyr Gln Thr Leu Gln Ala His
65                  70                  75                  80

Ala Gln Phe Leu Met Ala Asn Ala Asn Ser Lys Val Ala Leu Thr Gly
                85                  90                  95

His Thr Asp Glu Arg Gly Thr Arg Glu Tyr Asn Met Ala Leu Gly Glu
            100                 105                 110

Arg Arg Ala Lys Ala Val Gln Asn Tyr Leu Ile Thr Ser Gly Val Asn
        115                 120                 125

Pro Gln Gln Leu Glu Ala Val Ser Tyr Gly Lys Glu Ala Pro Val Asn
130                 135                 140

Pro Gly His Asp Glu Ser Ala Trp Lys Glu Asn Arg Arg Val Glu Ile
145                 150                 155                 160

Asn Tyr Glu Ala Val Pro Pro Leu Leu Lys
                165                 170

<210> SEQ ID NO 86
<211> LENGTH: 144
<212> TYPE: PRT
<213> ORGANISM: Acinetobacter baumannii

<400> SEQUENCE: 86

Met Lys Lys Ile Ile Phe Leu Gly Leu Ala Leu Val Ser Leu Thr Ala
1               5                   10                  15

Cys Ser Ser Val Gln His Lys Asp Ser Thr Pro Pro Lys Ile Gly Ser
            20                  25                  30

Pro Asn Pro Ala Ser Gln Tyr Cys Val Glu Gln Gly Gly Lys Leu Glu
        35                  40                  45

Ile Arg Asn Glu Ala Asn Gly Gln Val Gly Tyr Cys His Leu Pro Asn
50                  55                  60

```
Gly Gln Val Val Glu Glu Trp Lys Leu Phe Arg Asp Asn Gln Ala Asn
 65                  70                  75                  80

Cys Val Ser Glu Glu Ala Gln Lys Leu Val Gly Leu Ser Gly Leu Thr
                 85                  90                  95

Asp Asp Gln Ile Lys Gln Lys Thr Lys Ser Glu Ile Val Arg Lys Val
            100                 105                 110

Ala Pro Gly Gln Pro Met Thr Met Asp Tyr Arg Ser Asn Arg Val Thr
        115                 120                 125

Val Thr Ile Asp Pro Thr Ser Lys Lys Ile Thr Gln Ala Thr Cys Gly
    130                 135                 140
```

<210> SEQ ID NO 87
<211> LENGTH: 249
<212> TYPE: PRT
<213> ORGANISM: Acinetobacter baumannii

<400> SEQUENCE: 87

```
Met Lys Val Leu Arg Val Leu Val Thr Thr Thr Ala Leu Leu Ala Ala
  1               5                  10                  15

Gly Ala Ala Met Ala Asp Glu Ala Val Val His Asp Ser Tyr Ala Phe
                 20                  25                  30

Asp Lys Asn Gln Leu Ile Pro Val Gly Ala Arg Ala Glu Val Gly Thr
             35                  40                  45

Thr Gly Tyr Gly Gly Ala Leu Leu Trp Gln Ala Asn Pro Tyr Val Gly
 50                  55                  60

Leu Ala Leu Gly Tyr Asn Gly Gly Asp Ile Ser Trp Thr Asp Asp Val
 65                  70                  75                  80

Ser Val Asn Gly Thr Lys Tyr Asp Leu Asp Met Asp Asn Asn Asn Val
                 85                  90                  95

Tyr Leu Asn Ala Glu Ile Arg Pro Trp Gly Ala Ser Thr Asn Pro Trp
            100                 105                 110

Ala Gln Gly Leu Tyr Ile Ala Ala Gly Ala Ala Tyr Leu Asp Asn Asp
        115                 120                 125

Tyr Asp Leu Ala Lys Arg Ile Gly Asn Gly Asp Thr Leu Ser Ile Asp
    130                 135                 140

Gly Lys Asn Tyr Gln Gln Ala Val Pro Gly Gln Gly Gly Val Arg
145                 150                 155                 160

Gly Lys Met Ser Tyr Lys Asn Asp Ile Ala Pro Tyr Leu Gly Phe Gly
                165                 170                 175

Phe Ala Pro Lys Ile Ser Lys Asn Trp Gly Val Phe Gly Glu Val Gly
            180                 185                 190

Ala Tyr Tyr Thr Gly Asn Pro Lys Val Glu Leu Thr Gln Tyr Asn Leu
        195                 200                 205

Ala Pro Val Thr Gly Asn Pro Thr Ser Ala Gln Asp Ala Val Asp Lys
    210                 215                 220

Glu Ala Asn Glu Ile Arg Asn Asp Asn Lys Tyr Glu Trp Met Pro Val
225                 230                 235                 240

Gly Lys Val Gly Val Asn Phe Tyr Trp
                245
```

<210> SEQ ID NO 88
<211> LENGTH: 999
<212> TYPE: PRT
<213> ORGANISM: Acinetobacter baumannii

<400> SEQUENCE: 88

-continued

```
Met Arg Ala Val Glu Gly Asp Arg Leu Leu Ile Leu Lys His Gly Asp
1               5                   10                  15

Val Trp Lys Arg Met Ala Val Gly Phe Lys Met Asp Leu Asn His Trp
                20                  25                  30

Asp Pro Arg Ile Glu Ala Gln Arg Ser Trp Phe Ile Ser Arg Gln Pro
                35                  40                  45

Tyr Leu Asp Arg Leu Ser Ala Arg Ala Ser Arg Tyr Leu Tyr His Thr
                50                  55                  60

Val Lys Glu Ala Glu Arg Arg Gly Leu Pro Thr Glu Leu Ala Leu Leu
65                  70                  75                  80

Pro Val Ile Glu Ser Ser Tyr Asp Pro Ala Ala Thr Ser Ser Ala Ala
                85                  90                  95

Ala Ala Gly Leu Trp Gln Phe Ile Pro Ser Thr Gly Arg Ile Tyr Gly
                100                 105                 110

Leu Gln Gln Thr Gly Met Tyr Asp Gly Arg Arg Asp Val Val Glu Ser
                115                 120                 125

Thr Arg Ala Ala Tyr Glu Phe Leu Gly Ser Leu Tyr Asn Gln Phe Gly
130                 135                 140

Ser Trp Glu Leu Ala Leu Ala Ala Tyr Asn Ala Gly Pro Gly Arg Ile
145                 150                 155                 160

Gln Gln Ala Ile Asn Arg Asn Gln Ala Ala Gly Leu Pro Thr Asp Tyr
                165                 170                 175

Trp Ser Leu Lys Leu Pro Gln Glu Thr Met Asn Tyr Val Pro Arg Phe
                180                 185                 190

Leu Ala Val Ala Gln Ile Ile Lys Asn Pro Arg Ala Tyr Gly Val Ser
                195                 200                 205

Leu Pro Pro Ile Ala Asn Arg Pro His Phe Arg Glu Val Thr Leu Ser
                210                 215                 220

Ala Pro Leu Ser Leu Asn Glu Ile Ala Ser Val Thr Gly Leu Ser Arg
225                 230                 235                 240

Ala Glu Leu Tyr Ala Leu Asn Pro Gly Tyr Arg Gly Glu Thr Val Asp
                245                 250                 255

Pro Ala Ser Pro Met Arg Ile Leu Ile Pro Ala Asp Ile Ser Pro Ser
                260                 265                 270

Val Asp Asn Lys Leu Lys Gly Met Lys Ala Gly Gly Ser Ser Gly Trp
                275                 280                 285

Trp Ala Ser Val Thr Ser Pro Ser Lys Pro Thr Thr Thr Ser Thr
                290                 295                 300

Ser Val Thr Val Arg Thr Thr Pro Ser Thr Pro Ala Gln Pro Val Arg
305                 310                 315                 320

Pro Ser Thr Pro Ala Lys Thr Ser Ser Ser Val Thr Val Lys Thr
                325                 330                 335

Ala Thr Pro Arg Gly Ser Asp Ala Leu Ala Ala Phe Ala Ala Ser Ala
                340                 345                 350

Asp Val Pro Ser Ala Pro Arg Ile Pro Val Ala Val Thr Pro Ala Ala
                355                 360                 365

Asn Ile Lys Pro Val Arg Thr Glu Pro Pro Ile Ser Ala Thr Glu Arg
                370                 375                 380

Glu Lys Ile Leu Ala Ala Val Arg Ala Glu Gly Glu Lys Glu Thr Val
385                 390                 395                 400

Asp Gln Ala Leu Glu Pro Gln Ala Thr Gln Ala Glu Lys Asp Gln Val
                405                 410                 415
```

Val Ala Glu Leu Lys Ala Leu Ala Pro Gln Gly Thr Glu Ile Val Asp
            420                 425                 430

Pro Tyr Asp Gly Lys Ile Lys Leu Thr Ala Ile Gln Thr Ser Gln Ser
                435                 440                 445

Val Ala Glu Gln Gln Gly Lys Glu Val Ser Lys Gly Phe Ala Tyr Pro
            450                 455                 460

Lys Thr Leu Ala Glu Asp Ala Thr Leu Ala Asn Ser Glu Asp Ala Gln
465                 470                 475                 480

Arg Asn Lys Asp Lys Pro Tyr Ile Lys Thr Asp Thr Asp Val Val Val
                485                 490                 495

Val Gln Pro Lys Gly Lys Arg Ser Thr Tyr Thr Val Gln Pro Gly Asp
            500                 505                 510

Thr Leu Ala Val Ile Ala Met Lys Asn Gly Val Asn Trp Arg Asp Val
            515                 520                 525

Ala Lys Trp Asn Gln Ile Asp Pro Glu Lys Thr Leu Phe Val Gly Thr
            530                 535                 540

Ser Leu Tyr Leu Tyr Asp Ala Lys Pro Gln Glu Ala Glu Thr Thr Ala
545                 550                 555                 560

Lys Ser Ala Ala Lys Pro Asp Val Tyr Val Gln Ala Asn Asp Ser
                565                 570                 575

Leu Thr Gly Val Ala Asn Gln Phe Asn Leu Ser Val Lys Gln Leu Ala
            580                 585                 590

Glu Tyr Asn Asp Leu Ser Val Thr Asp Gly Leu Phe Val Gly Gln Lys
                595                 600                 605

Leu Gln Leu Lys Glu Pro Lys Gly Asn Arg Ala Ala Lys Val Glu Pro
            610                 615                 620

Lys Ala Ile Gln Ala Ser Thr Arg Arg Ile Ala Thr Lys Ser Tyr Thr
625                 630                 635                 640

Val Lys Arg Gly Glu Tyr Leu Lys Leu Ile Ala Asp Arg Tyr Ala Leu
                645                 650                 655

Ser Asn Gln Glu Leu Ala Asp Leu Thr Pro Gly Leu Thr Ala Gly Ser
            660                 665                 670

Asn Leu Ile Val Gly Gln Lys Ile Asn Val Pro Ala Lys Glu Ile Thr
            675                 680                 685

Val Asp Glu Val Asp Asp Ser Lys Ala Ser Gly Lys Tyr Glu Lys Leu
            690                 695                 700

Ala Ala Gly Pro Ser Tyr Lys Thr Glu Ser Tyr Lys Val Gln Arg Gly
705                 710                 715                 720

Asp Thr Leu Ser Ser Ile Ala Thr Lys Ser Lys Ile Ser Leu Ala Glu
                725                 730                 735

Leu Ala Glu Leu Asn Asn Leu Lys Ala Asn Ser His Val Gln Leu Gly
            740                 745                 750

Gln Thr Leu Lys Val Pro Ala Gly Ala Ser Val Pro Asp Gln Tyr Val
            755                 760                 765

Val Gln Ser Gly Asp Ser Leu Asn Ala Ile Ala Lys Tyr Asn Leu
            770                 775                 780

Gln Thr Ser Tyr Leu Ala Asp Leu Asn Gly Leu Ser Arg Thr Ala Gly
785                 790                 795                 800

Leu Arg Ala Gly Gln Arg Leu Lys Leu Thr Gly Glu Val Glu Thr Thr
                805                 810                 815

Ser Lys Val Ser Ala Lys Asn Thr Lys Glu Glu Thr Pro Glu Thr Tyr
            820                 825                 830

Thr Val Lys Ser Gly Asp Ser Leu Gly Asn Ile Ala Asn Arg Tyr His

```
                835                 840                 845
Leu Gln Leu Asp Tyr Leu Ala Ala Leu Asn Gly Leu Ser Arg Asn Ser
    850                 855                 860

Asn Val Arg Val Gly Gln Arg Leu Lys Leu Thr Gly Asp Leu Pro Thr
865                 870                 875                 880

Val Glu Thr Ala Lys Thr Asp Thr Ala Lys Ser Ser Pro Lys Ala Val
                885                 890                 895

Val Ala Gly Lys Asn Thr Glu Lys Tyr Thr Val Lys Ala Gly Glu Ser
            900                 905                 910

Leu Asn Ala Ile Ala Ser Arg Ala Gly Ile Ser Val Arg Glu Leu Ala
        915                 920                 925

Glu Met Asn Ala Leu Lys Ala Asn Ala Asn Leu Gln Arg Gly Gln Asn
    930                 935                 940

Ile Val Ile Pro Lys Thr Val Val Glu Tyr Lys Val Lys Arg Gly Asp
945                 950                 955                 960

Thr Leu Ile Gly Leu Ala Ser Lys Tyr Gly Leu Glu Thr Thr Leu Leu
                965                 970                 975

Ala Glu Leu Asn Asn Leu Thr Pro Ser Thr Gln Leu Arg Ile Gly Asp
            980                 985                 990

Ile Ile Lys Val Pro Asn Leu
        995

<210> SEQ ID NO 89
<211> LENGTH: 519
<212> TYPE: PRT
<213> ORGANISM: Acinetobacter baumannii

<400> SEQUENCE: 89

Met Arg Asn Ser Ala Met Gln Gln Leu Asn Pro Ser Glu Ile Ser Ala
1               5                   10                  15

Leu Ile Lys Gln Arg Ile Gly Asp Leu Asp Thr Ser Ala Thr Ala Lys
            20                  25                  30

Asn Glu Gly Thr Ile Val Met Val Ser Asp Gly Ile Val Arg Ile His
        35                  40                  45

Gly Leu Ala Asp Ala Met Tyr Gly Glu Met Ile Glu Phe Asp Gly Gly
    50                  55                  60

Leu Phe Gly Met Ala Leu Asn Leu Glu Gln Asp Ser Val Gly Ala Val
65                  70                  75                  80

Val Leu Gly Asn Tyr Leu Ser Leu Gln Glu Gly Gln Lys Ala Arg Cys
                85                  90                  95

Thr Gly Arg Val Leu Glu Val Pro Val Gly Pro Glu Leu Leu Gly Arg
            100                 105                 110

Val Val Asp Ala Leu Gly Asn Pro Ile Asp Gly Lys Gly Pro Ile Asp
        115                 120                 125

Ala Lys Leu Thr Asp Ala Val Glu Lys Val Ala Pro Gly Val Ile Trp
    130                 135                 140

Arg Gln Ser Val Asp Glu Pro Val Gln Thr Gly Tyr Lys Ser Val Asp
145                 150                 155                 160

Thr Met Ile Pro Val Gly Arg Gly Gln Arg Glu Leu Ile Ile Gly Asp
                165                 170                 175

Arg Gln Thr Gly Lys Thr Ala Met Ala Ile Asp Ala Ile Ile Ala Gln
            180                 185                 190

Lys His Ser Gly Ile Lys Cys Val Tyr Val Ala Ile Gly Gln Lys Gln
        195                 200                 205
```

```
Ser Thr Ile Ala Asn Val Val Arg Lys Leu Glu Glu Thr Gly Ala Met
    210                 215                 220
Ala Tyr Thr Thr Val Val Ala Ala Ala Ala Asp Pro Ala Ala Met
225                 230                 235                 240
Gln Tyr Leu Ala Pro Tyr Ser Gly Cys Thr Met Gly Glu Tyr Phe Arg
                245                 250                 255
Asp Arg Gly Glu Asp Ala Leu Ile Ile Tyr Asp Asp Leu Ser Lys Gln
                260                 265                 270
Ala Val Ala Tyr Arg Gln Ile Ser Leu Leu Leu Arg Arg Pro Pro Gly
            275                 280                 285
Arg Glu Ala Tyr Pro Gly Asp Val Phe Tyr Leu His Ser Arg Leu Leu
290                 295                 300
Glu Arg Ala Ser Arg Val Ser Ala Asp Tyr Val Glu Lys Phe Thr Asn
305                 310                 315                 320
Gly Ala Val Thr Gly Gln Thr Gly Ser Leu Thr Ala Leu Pro Ile Ile
                325                 330                 335
Glu Thr Gln Ala Gly Asp Val Ser Ala Phe Val Pro Thr Asn Val Ile
                340                 345                 350
Ser Ile Thr Asp Gly Gln Ile Phe Leu Glu Thr Ser Leu Phe Asn Ala
            355                 360                 365
Gly Ile Arg Pro Ala Val Asn Ala Gly Ile Ser Val Ser Arg Val Gly
370                 375                 380
Gly Ser Ala Gln Thr Lys Ile Ile Lys Lys Leu Ser Gly Gly Ile Arg
385                 390                 395                 400
Thr Ala Leu Ala Gln Tyr Arg Glu Leu Ala Ala Phe Ala Gln Phe Ala
                405                 410                 415
Ser Asp Leu Asp Glu Ala Thr Arg Lys Gln Leu Glu His Gly Gln Arg
                420                 425                 430
Val Thr Glu Leu Met Lys Gln Lys Gln Tyr Ala Pro Tyr Ser Ile Ala
            435                 440                 445
Asp Gln Ala Val Ser Val Tyr Ala Ser Asn Glu Gly Tyr Met Ala Asp
450                 455                 460
Val Glu Val Lys Lys Ile Val Asp Phe Asp Ala Ala Leu Ile Ser Tyr
465                 470                 475                 480
Phe Arg Ser Glu Tyr Ala Pro Leu Met Lys Gln Ile Asp Glu Thr Gly
                485                 490                 495
Asp Tyr Asn Lys Asp Ile Glu Ala Ala Ile Lys Ser Gly Ile Glu Ser
                500                 505                 510
Phe Lys Ala Thr Gln Thr Tyr
            515
```

<210> SEQ ID NO 90

<400> SEQUENCE: 90

000

<210> SEQ ID NO 91

<400> SEQUENCE: 91

000

<210> SEQ ID NO 92

<400> SEQUENCE: 92

```
<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 20
<212> TYPE: DNA
<213> ORGANISM: Artificial Sequence
<220> FEATURE:
<223> OTHER INFORMATION: primer forward

<400> SEQUENCE: 100
gctaattggt gaaggtagtc                                         20

<210> SEQ ID NO 101
<211> LENGTH: 20
<212> TYPE: DNA
<213> ORGANISM: Artificial Sequence
<220> FEATURE:
<223> OTHER INFORMATION: primer reverse

<400> SEQUENCE: 101
gacgaatcgt ttgaatctgc                                         20
```